(12) United States Patent
Amor-Gueret et al.

(10) Patent No.: US 11,209,421 B2
(45) Date of Patent: Dec. 28, 2021

(54) CYTIDINE DEAMINASE EXPRESSION LEVEL IN CANCER AS A NEW THERAPEUTIC TARGET

(71) Applicants: CENTRE NATIONAL DE LA RECHERCHE SCIENTIFIQUE, Paris (FR); INSTITUT CURIE, Paris (FR)

(72) Inventors: Mounira Amor-Gueret, L'Hay les Roses (FR); Hamza Mameri, Pantin (FR)

(73) Assignees: CENTRE NATIONAL DE LA RECHERCHE SCIENTIFIQUE, Paris (FR); INSTITUT CURIE, Paris (FR)

( * ) Notice: Subject to any disclaimer, the term of this patent is extended or adjusted under 35 U.S.C. 154(b) by 203 days.

(21) Appl. No.: 16/086,624

(22) PCT Filed: Mar. 31, 2017

(86) PCT No.: PCT/EP2017/057752
§ 371 (c)(1),
(2) Date: Sep. 20, 2018

(87) PCT Pub. No.: WO2017/167989
PCT Pub. Date: Oct. 5, 2017

(65) Prior Publication Data
US 2019/0293629 A1 Sep. 26, 2019

(30) Foreign Application Priority Data
Mar. 31, 2016 (EP) ..................................... 16305380

(51) Int. Cl.
*G01N 33/50* (2006.01)
*C12Q 1/6886* (2018.01)

(52) U.S. Cl.
CPC ....... *G01N 33/5011* (2013.01); *C12Q 1/6886* (2013.01); *G01N 33/5023* (2013.01); *G01N 2800/52* (2013.01)

(58) Field of Classification Search
None
See application file for complete search history.

(56) References Cited

U.S. PATENT DOCUMENTS 6,136,791 A * 10/2000 Nyce ....................... A61K 31/70
514/43

FOREIGN PATENT DOCUMENTS

| EP | 2348131 | * | 7/2011 |
| WO | WO 2010/093465 | | 8/2010 |

(Continued)

OTHER PUBLICATIONS

Mameri, H. e tal. "Cytidine Deaminase Deficiency Reveals New Therapeutic Opportunities against Cancer" Clinical Cancer Research, Apr. 15, 2017, published online Sep. 6, 2016, pp. 2116-2126, vol. 23, No. 8 (Year: 2016).*

(Continued)

*Primary Examiner* — Karl J Puttlitz
(74) *Attorney, Agent, or Firm* — Saliwanchik, Lloyd & Eisenschenk

(57) ABSTRACT

The present invention provides an in vitro method for selecting a patient affected with a tumor for a treatment with an antitumor compound, wherein the method comprises a step of measuring the expression level of CDA (Cytidine Deaminase) in a cancer sample from said patient. When the CDA expression level of a cancer sample is lower than the reference expression level, it is indicative that the patient is suitable for a treatment with an antitumor compound selected from the group consisting of the compounds of table 4, in particular aminoflavone. Alternatively, when the (Continued)

CDA expression level of a cancer sample is higher than the reference expression level, it is indicative that the patient is suitable for a treatment with an antitumor compound selected from the group consisting of the compounds of table 3, in particular dasatinib.

15 Claims, 27 Drawing Sheets

Specification includes a Sequence Listing.

(56) References Cited

FOREIGN PATENT DOCUMENTS

| WO | 2013003112 | * | 1/2013 |
|----|------------|---|--------|
| WO | WO 2013/003112 | | 1/2013 |

OTHER PUBLICATIONS

Amit, M. et al. "Macrophages increase the resistance of pancreatic adenocarcinoma cells to gemcitabine by upregulating cytidine deaminase" *OncoImmunology*, Dec. 2013, pp. e27231-1-e27231-3, vol. 2, No. 12.

Brennig, S. et al. "Chemoprotection of murine hematopoietic cells by combined gene transfer of cytidine deaminase (CDD) and multidrug resistance 1 gene (MDR1)" *Journal of Experimental & Clinical Cancer Research*, Dec. 12, 2015, pp. 1-12, vol. 34, No. 148.

Ebrahem, Q. et al. "High cytidine deaminase expression in the liver provides sanctuary for cancer cells from decitabine treatment effects" *Oncotarget*, Sep. 27, 2012, pp. 1137-1145, vol. 3, No. 10.

Hosokawa, M. et al. "Acquired resistance to decitabine and cross-resistance to gemcitabine during the long-term treatment of human HCT116 colorectal cancer cells with decitabine" *Oncology Letters*, 2015, pp. 761-767, vol. 10, No. 2.

Kawamura, K. et al. "Expression of activation-induced cytidine deaminase is associated with a poor prognosis of diffuse large B cell lymphoma patients treated with CHOP-based chemotherapy" *Journal of Cancer Research and Clinical Oncology*, 2016, pp. 27-36, vol. 142, No. 1.

Serdjebi, C. et al. "Role of cytidine deaminase in toxicity and efficacy of nucleosidic analogs" *Expert Opinion on Drug Metabolism & Toxicology*, Dec. 13, 2014, pp. 665-672, vol. 11, No. 5.

Ye, F-G. et al. "Cytidine Deaminase Axis Modulated by miR-484 Differentially Regulates Cell Proliferation and Chemoresistance in Breast Cancer" *Cancer Research*, Apr. 1, 2015, pp. 1504-1515, vol. 75, No. 7.

Written Opinion in International Application No. PCT/EP2017/057752, dated Jun. 26, 2017, pp. 1-9.

Mameri, H. et al. "Cytidine Deaminase Deficiency Reveals New Theraputic Opportunities against Cancer" *Clinical Cancer Research*, online Sep. 6, 2016, pp. 2116-2126, vol. 23, No. 8.

* cited by examiner

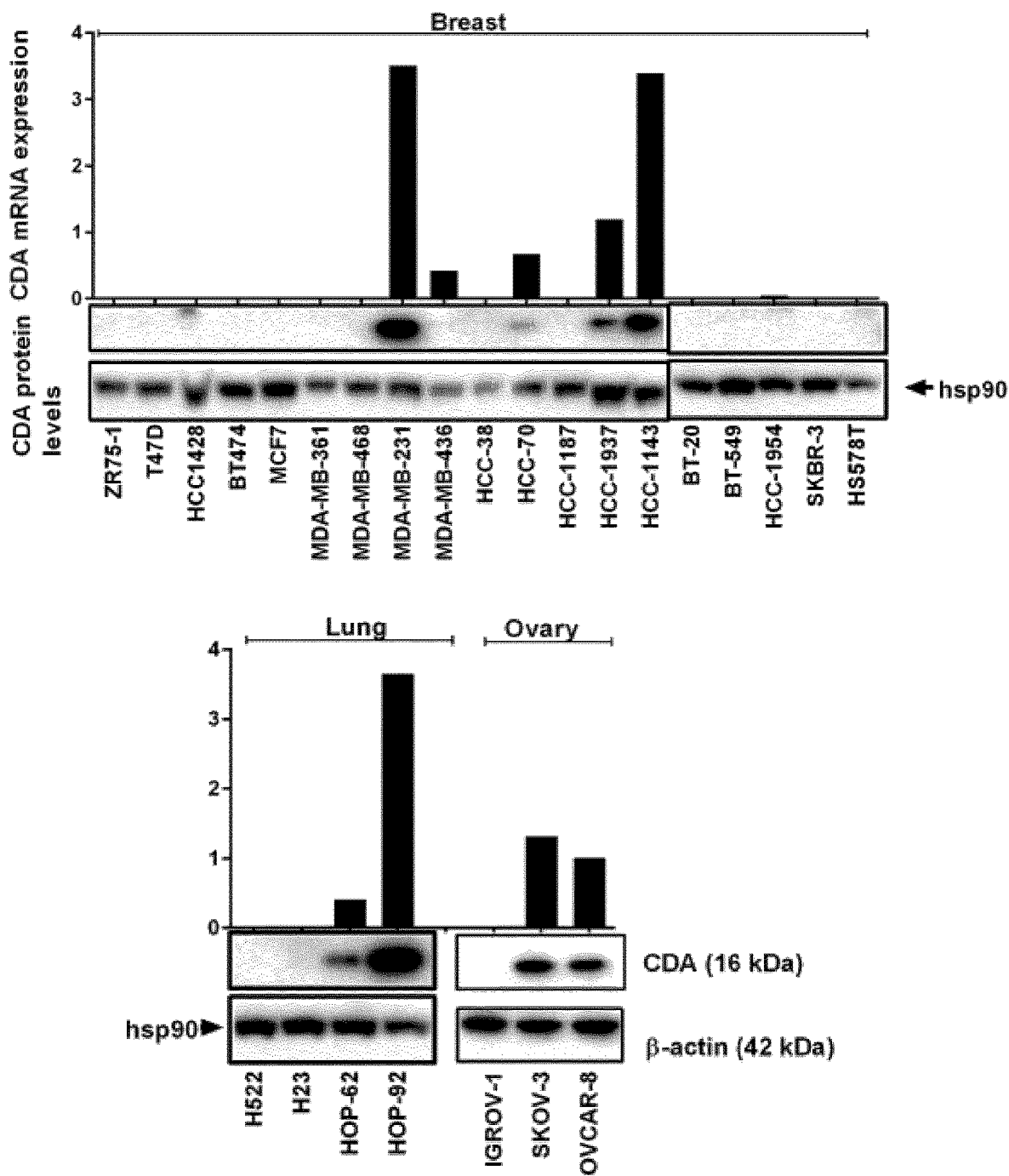
Figure 1 (following)

C
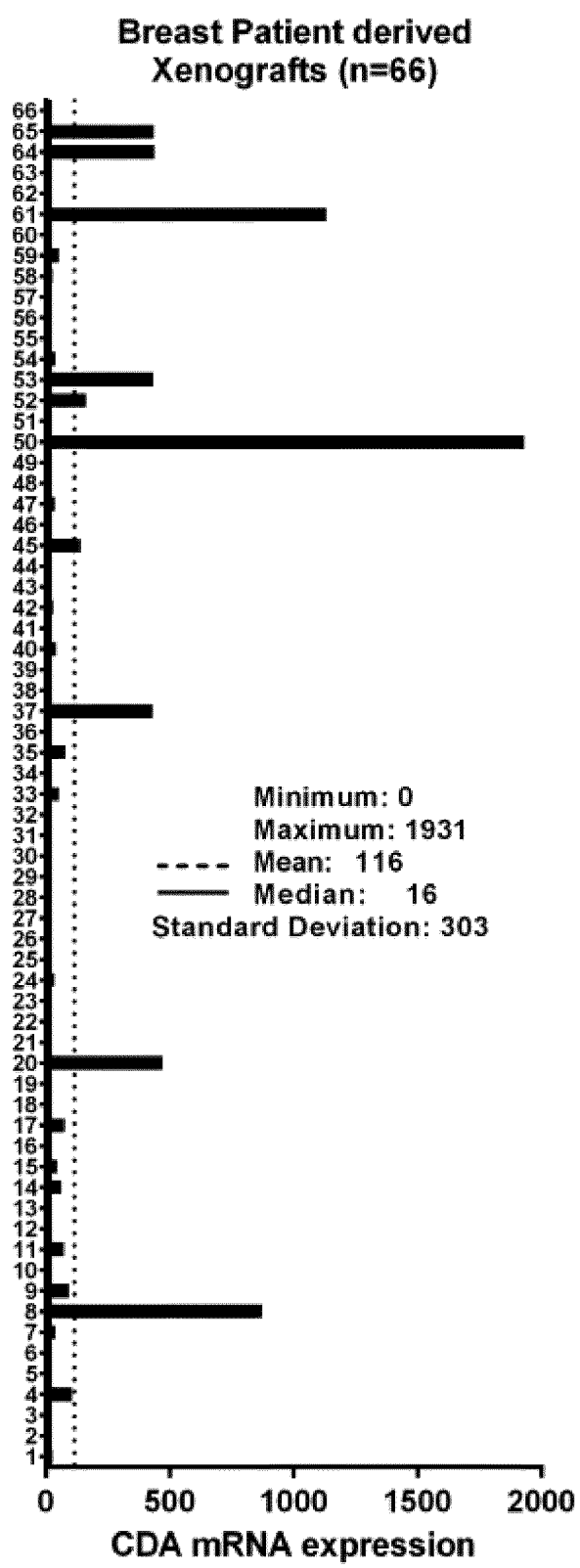
Figure 1 (following)

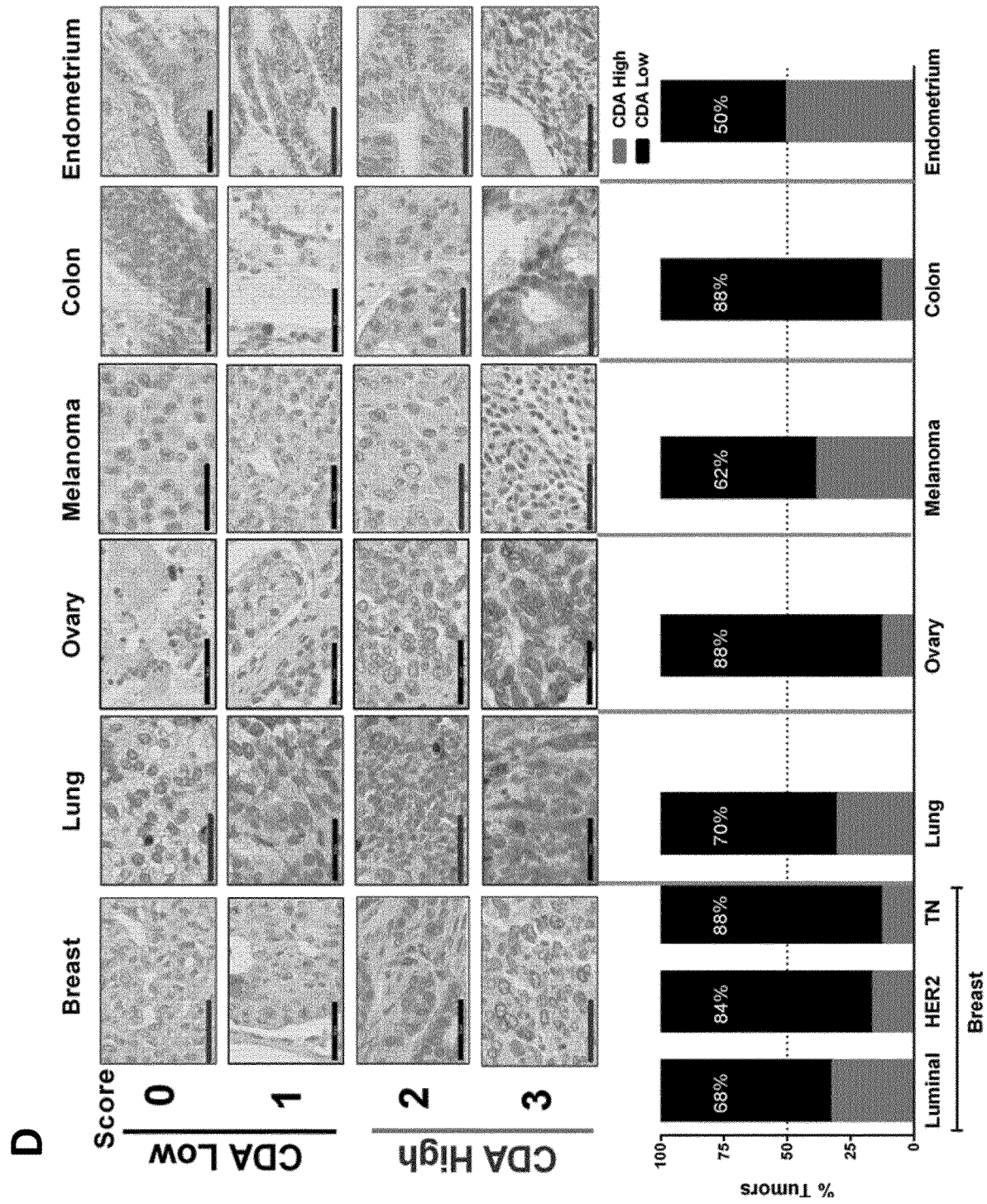
Figure 1 (following)

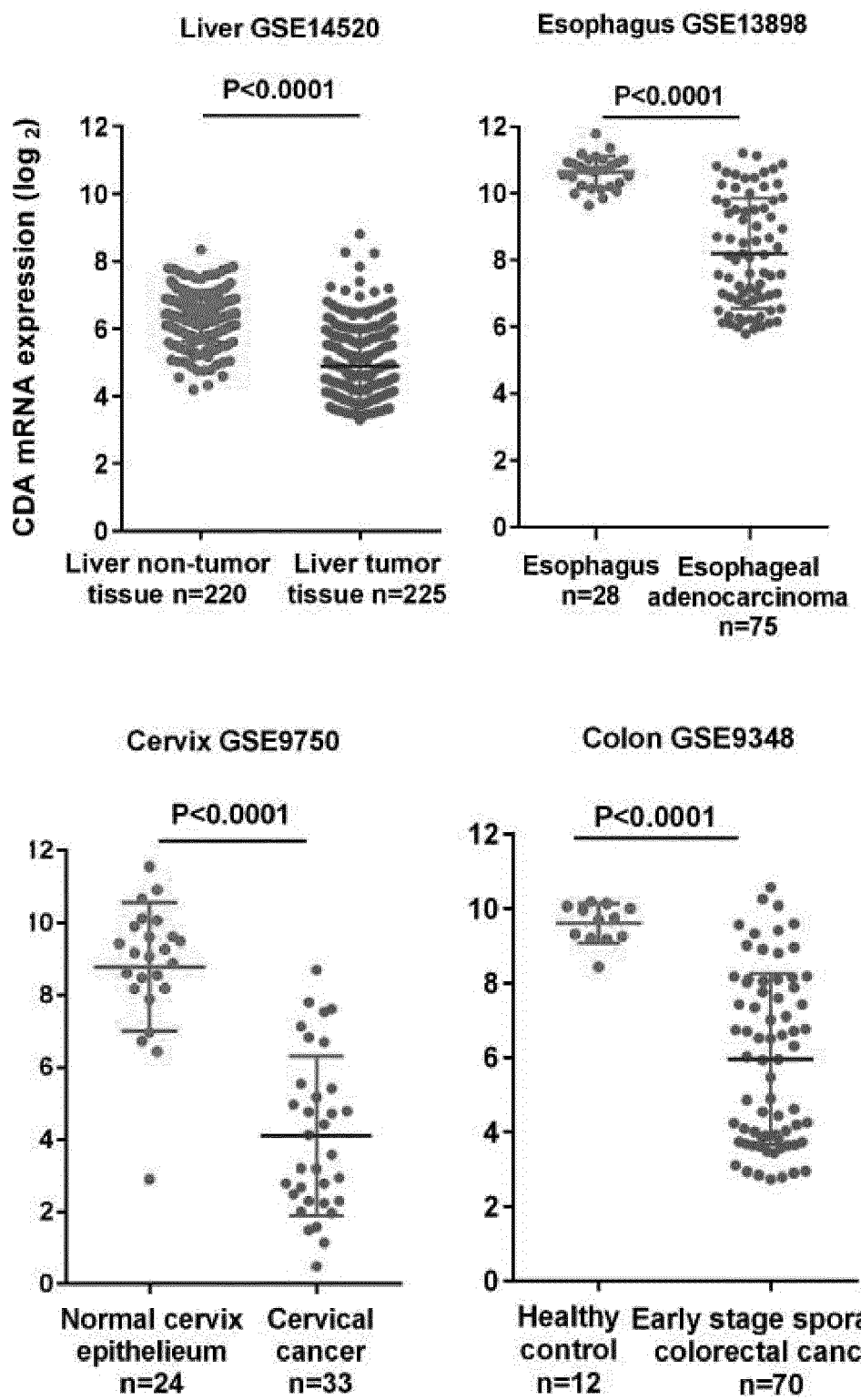
Figure 1 (following)

Figure 1 (following)

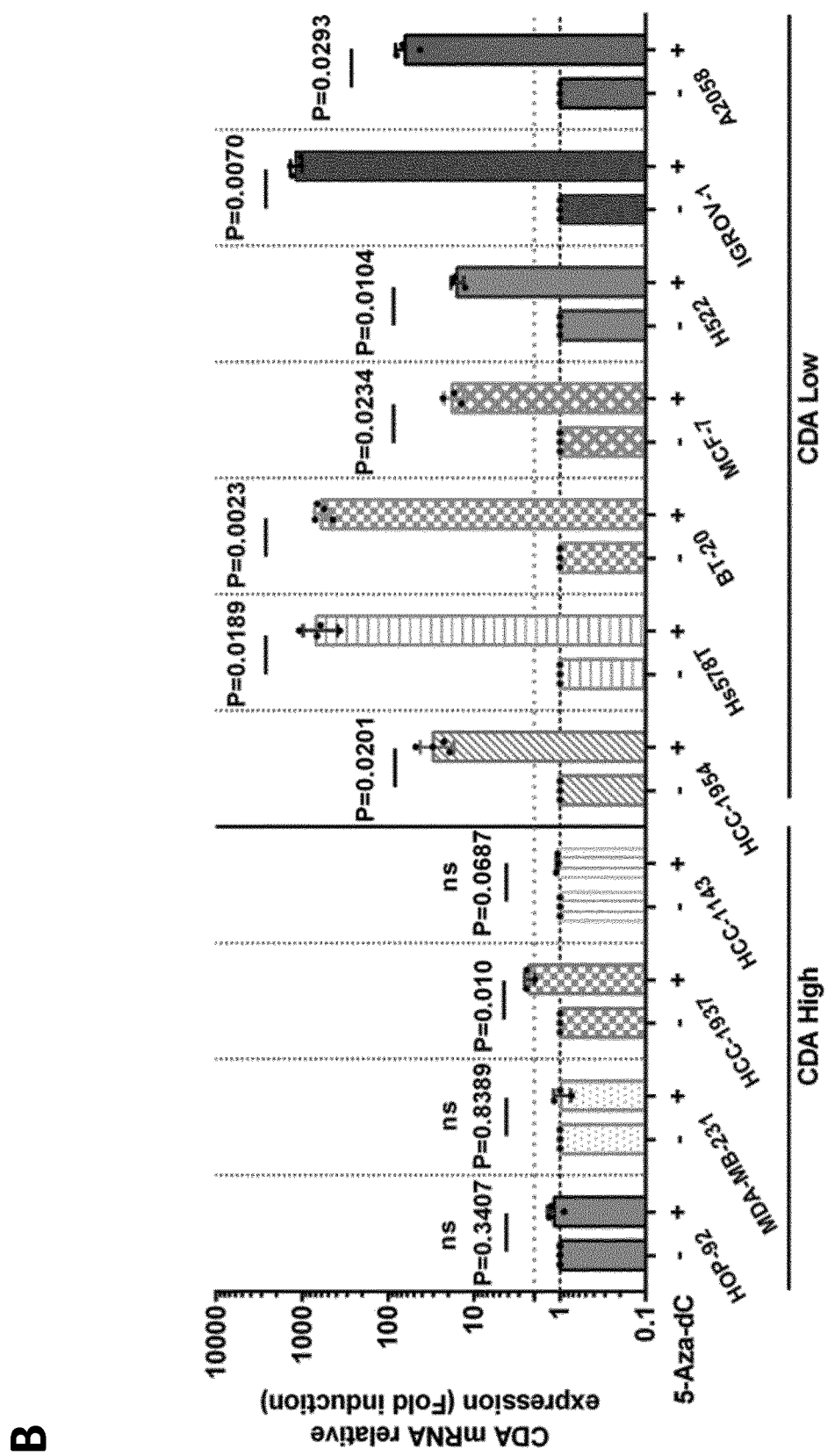
Figure 2 (following)

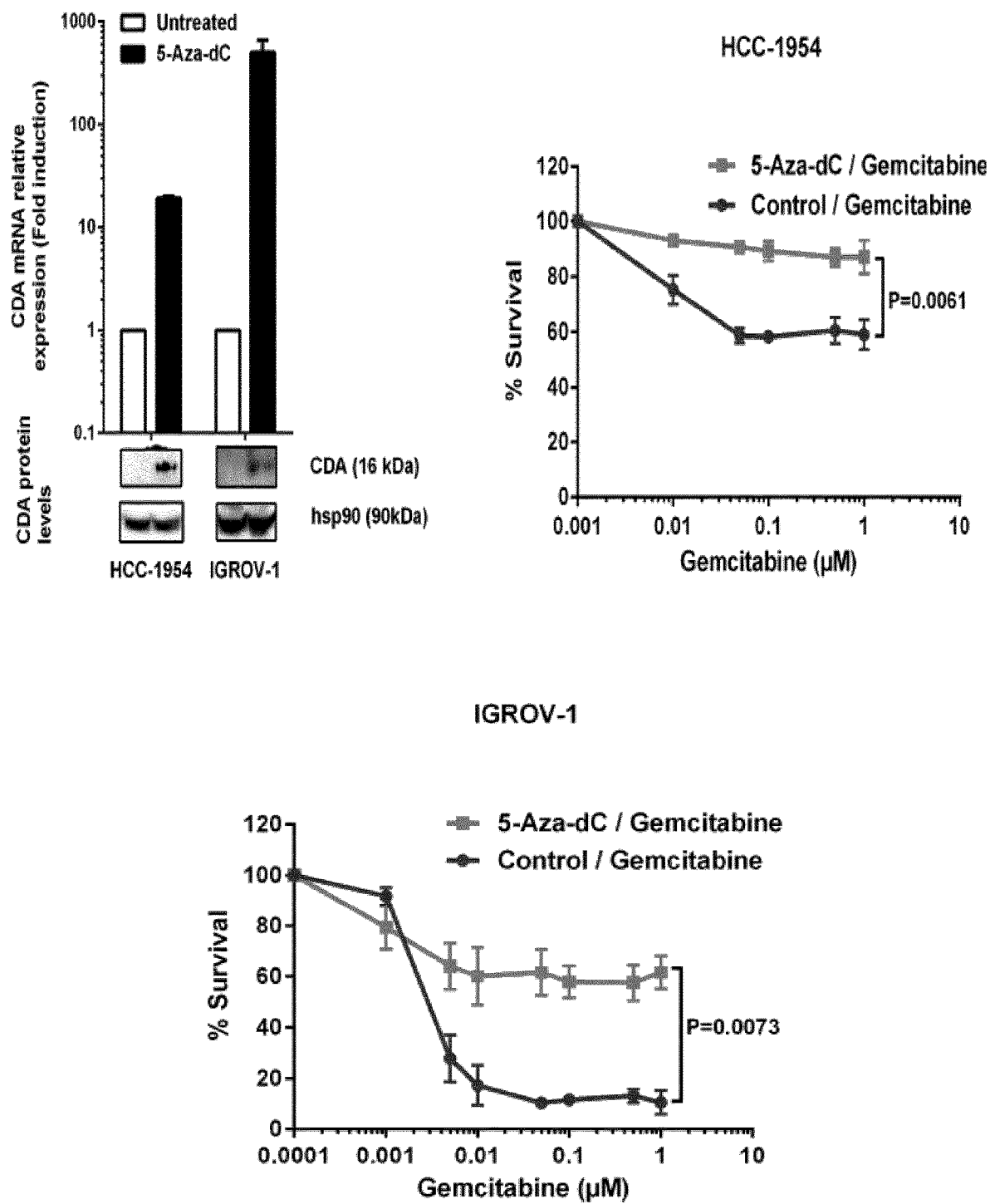
Figure 2 (following)

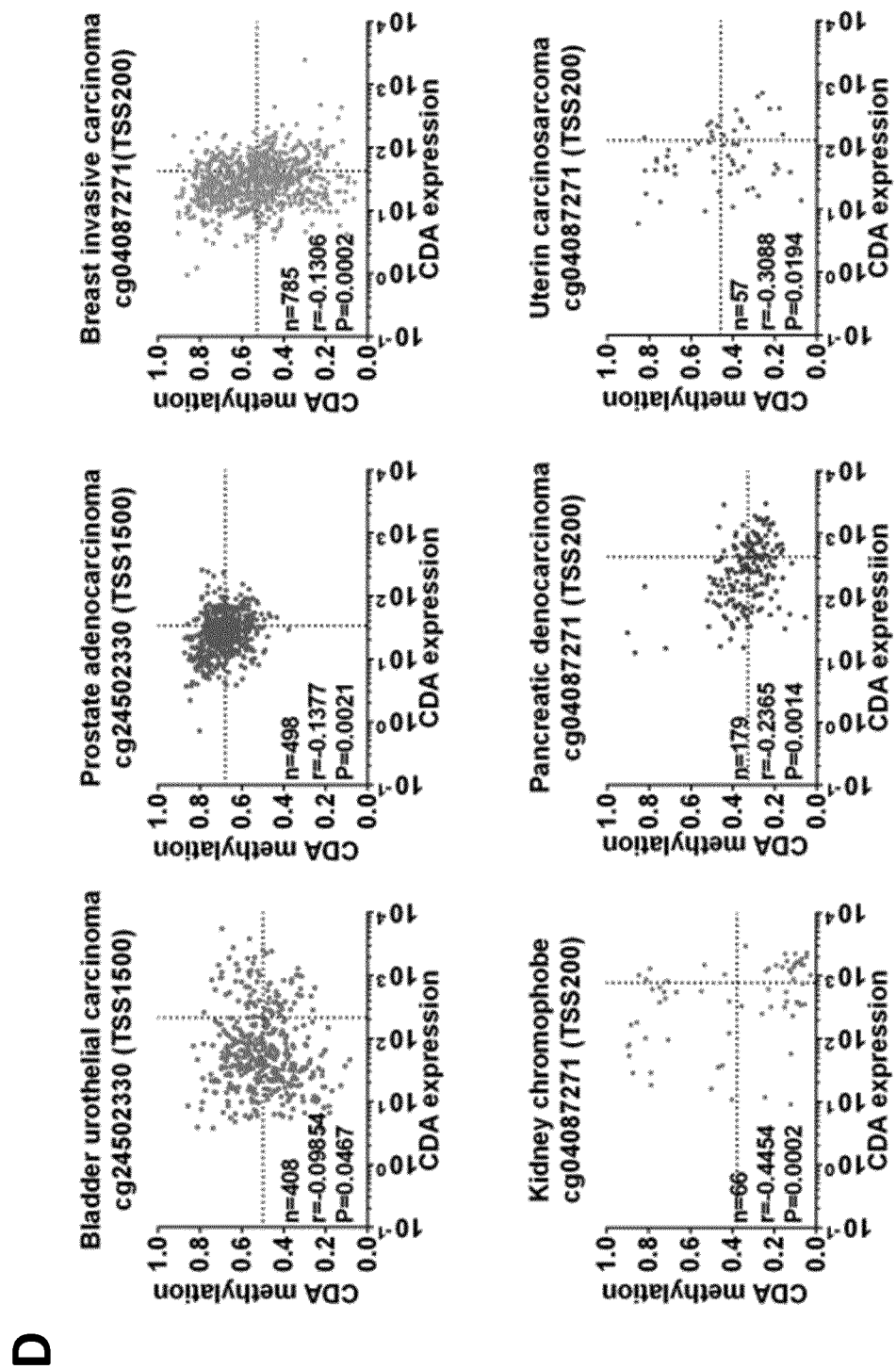
Figure 2 (following)

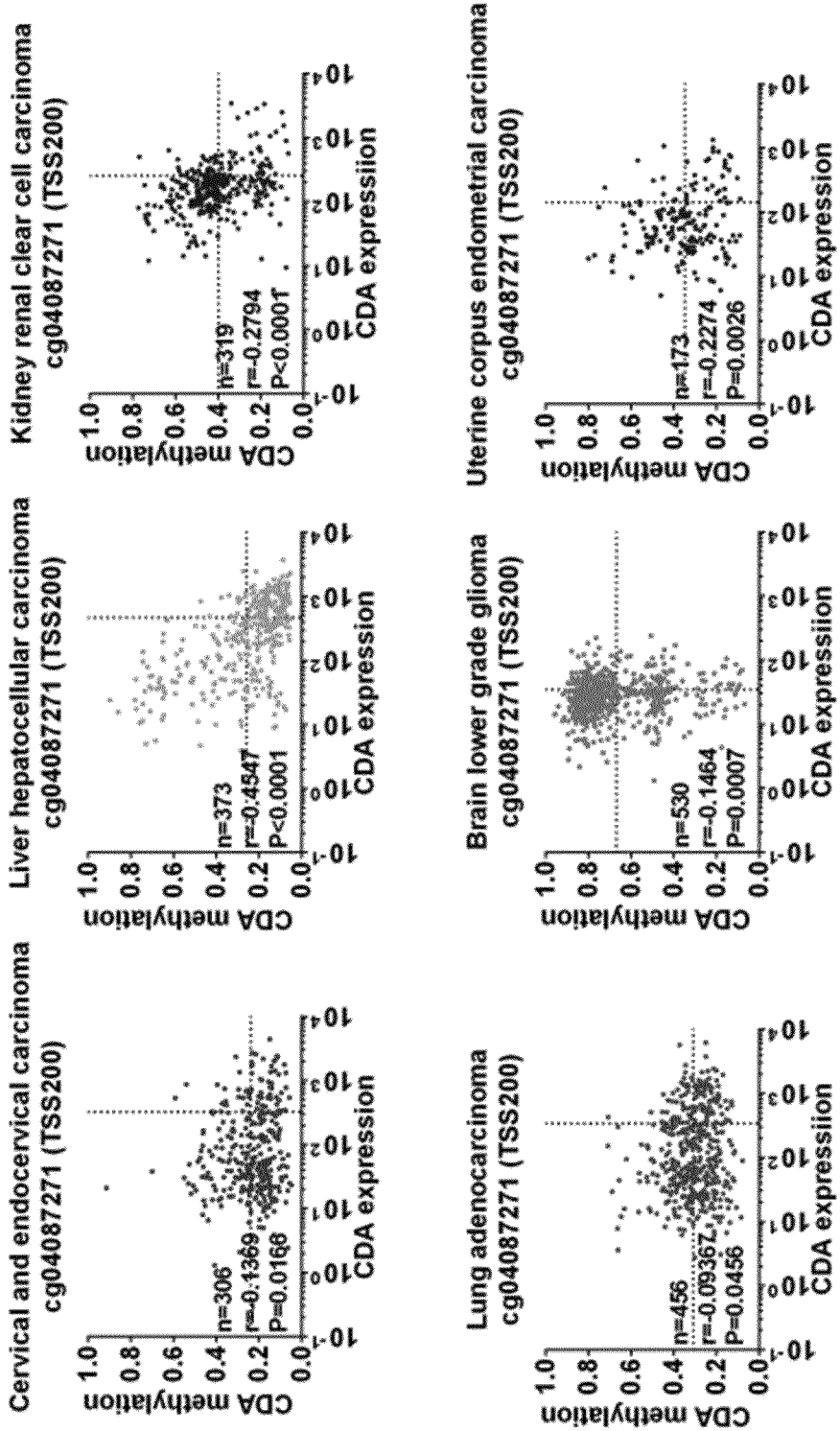
Figure 2 (following)

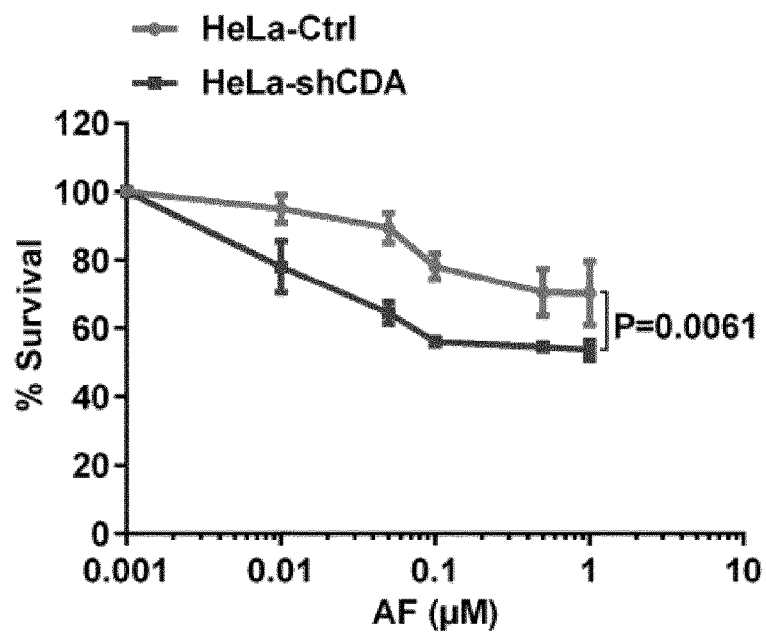
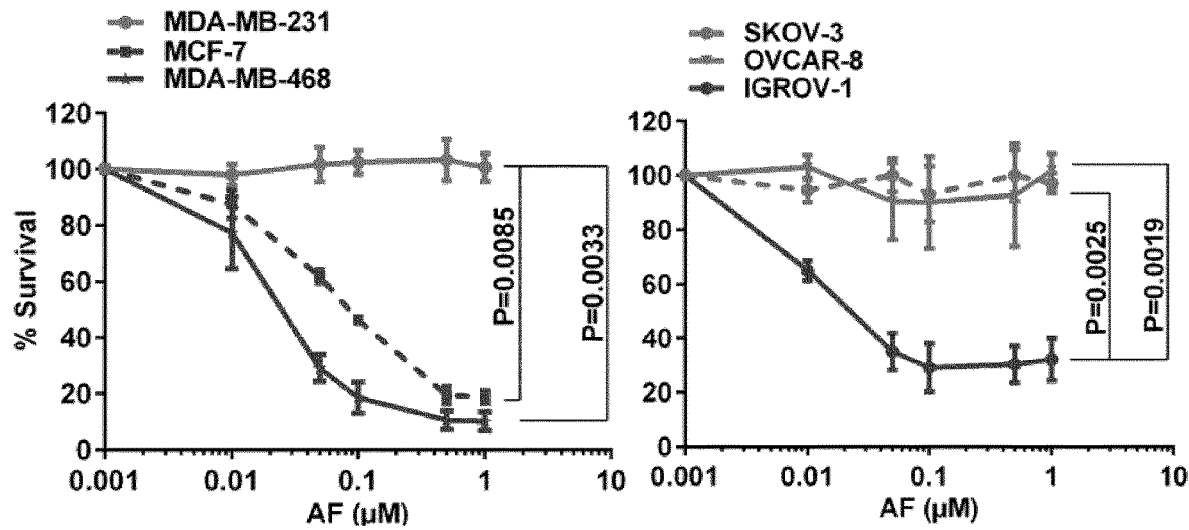
Figure 3 (following)

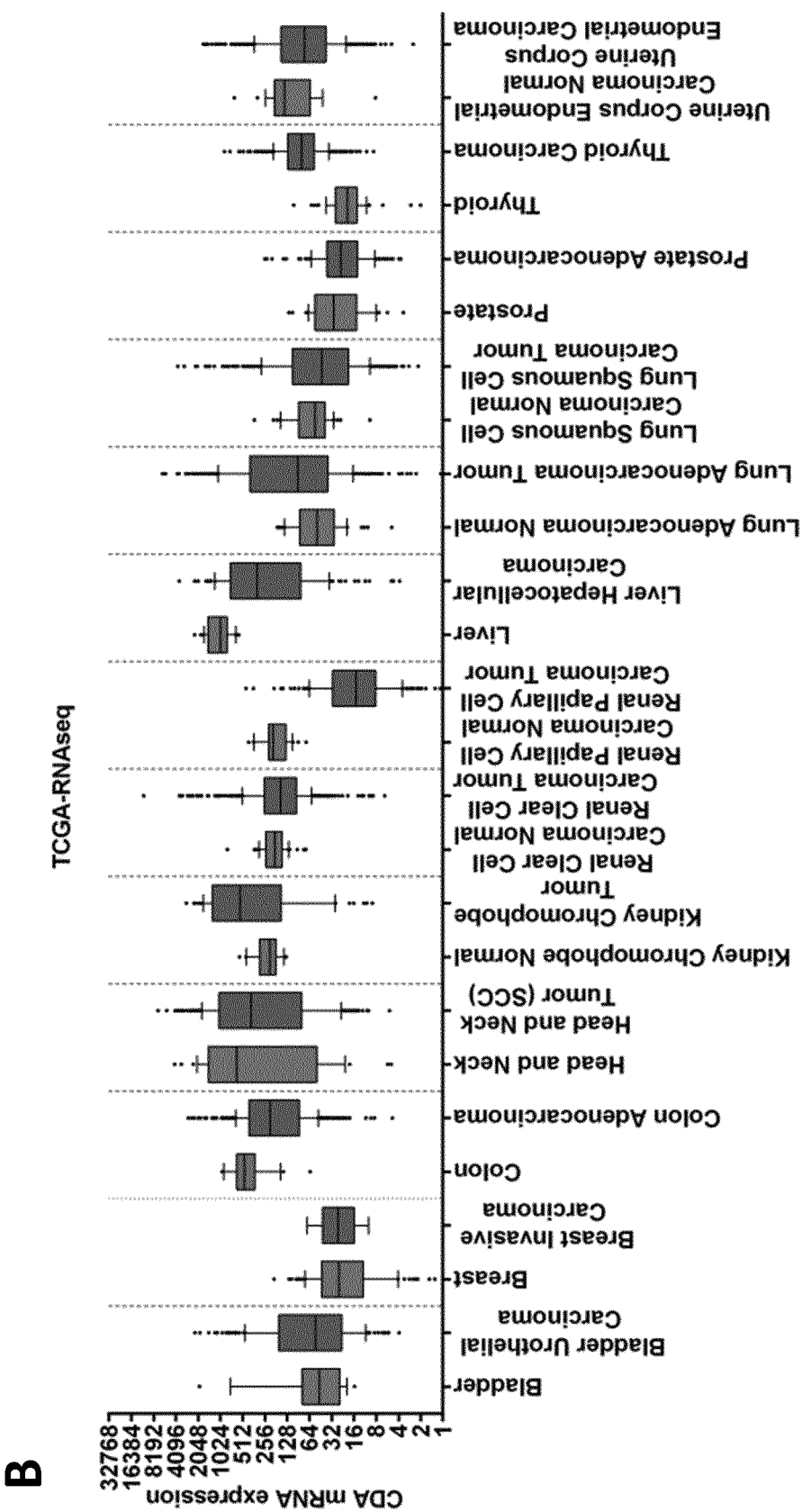
Figure 4 (following)

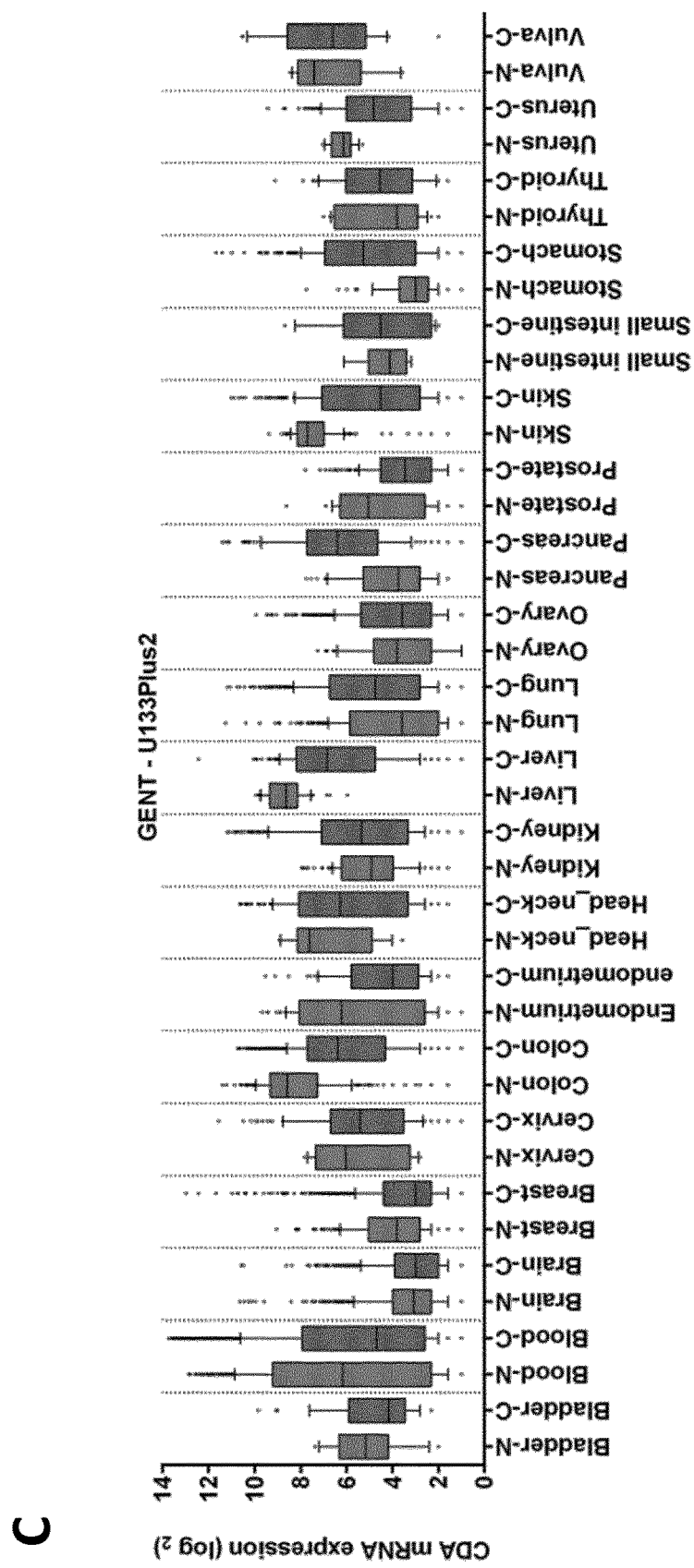
Figure 4 (following)

D
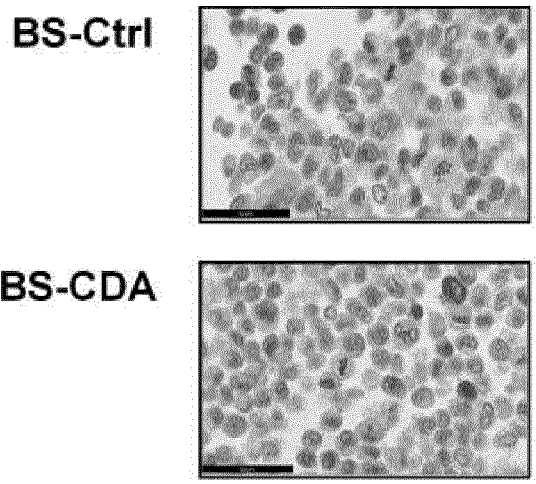
E
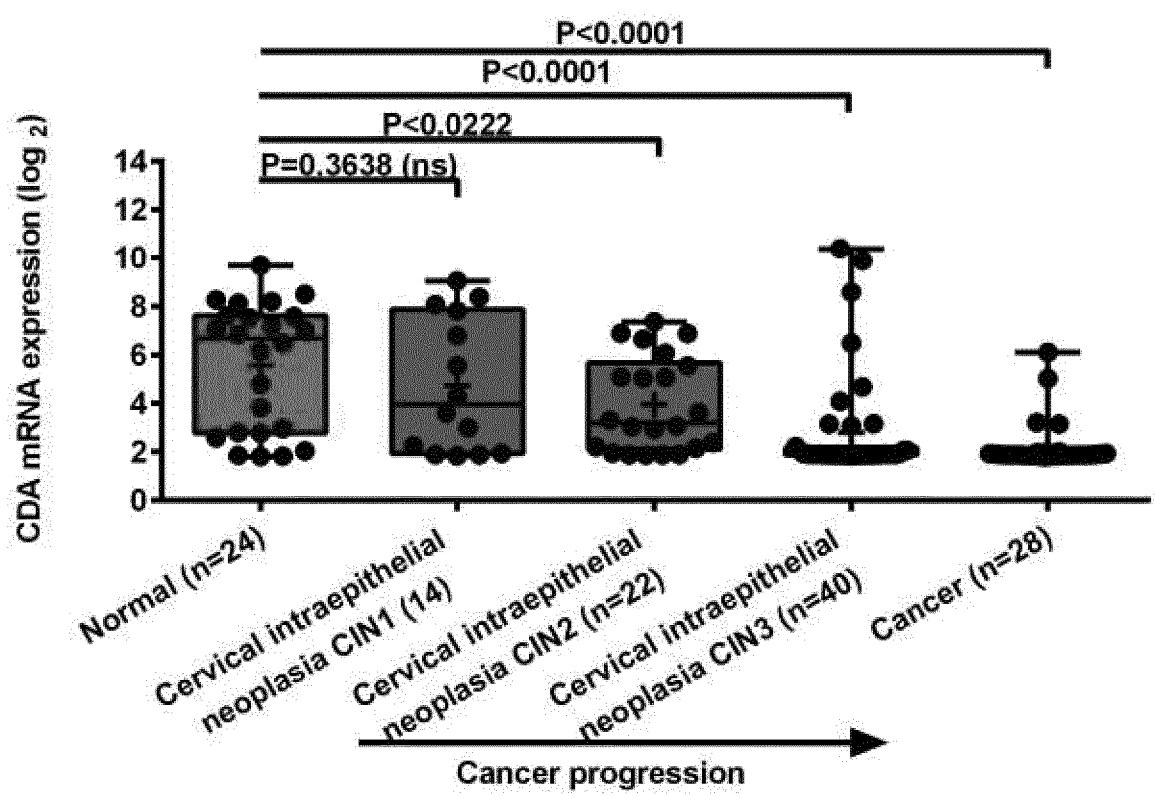
Figure 4 (following)

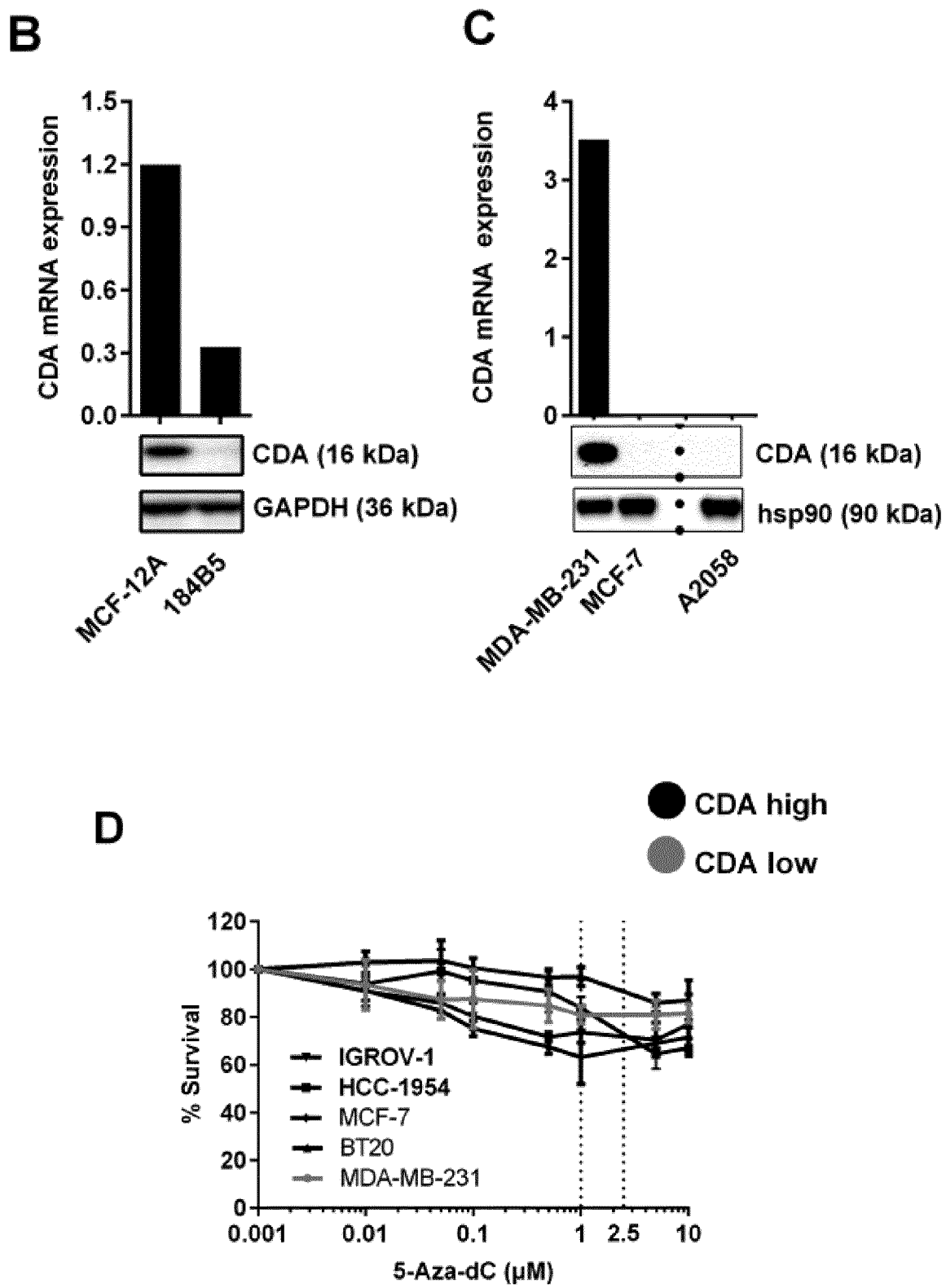
Figure 5 (following)

Figure 5 (following)

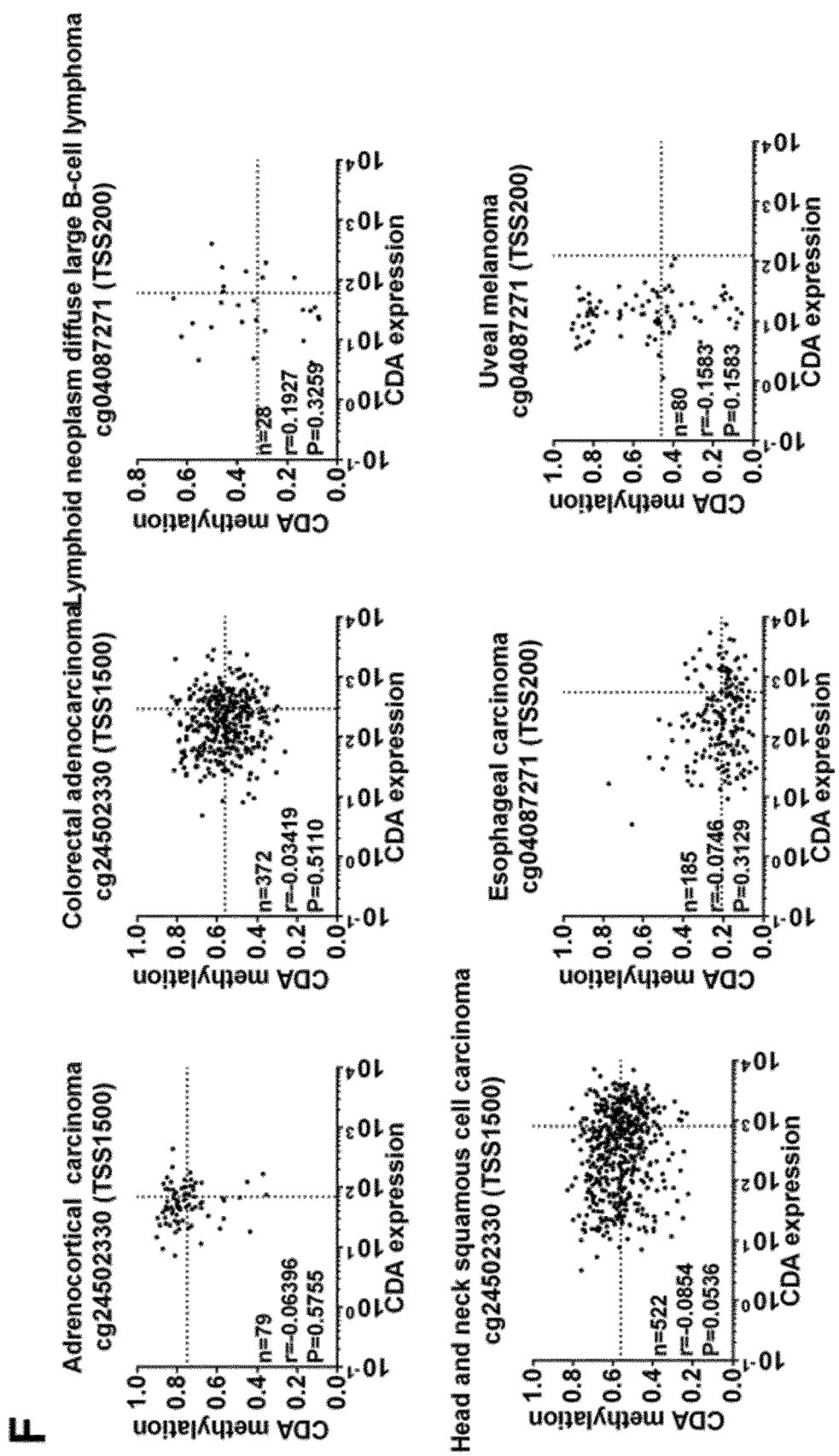
Figure 5 (following)

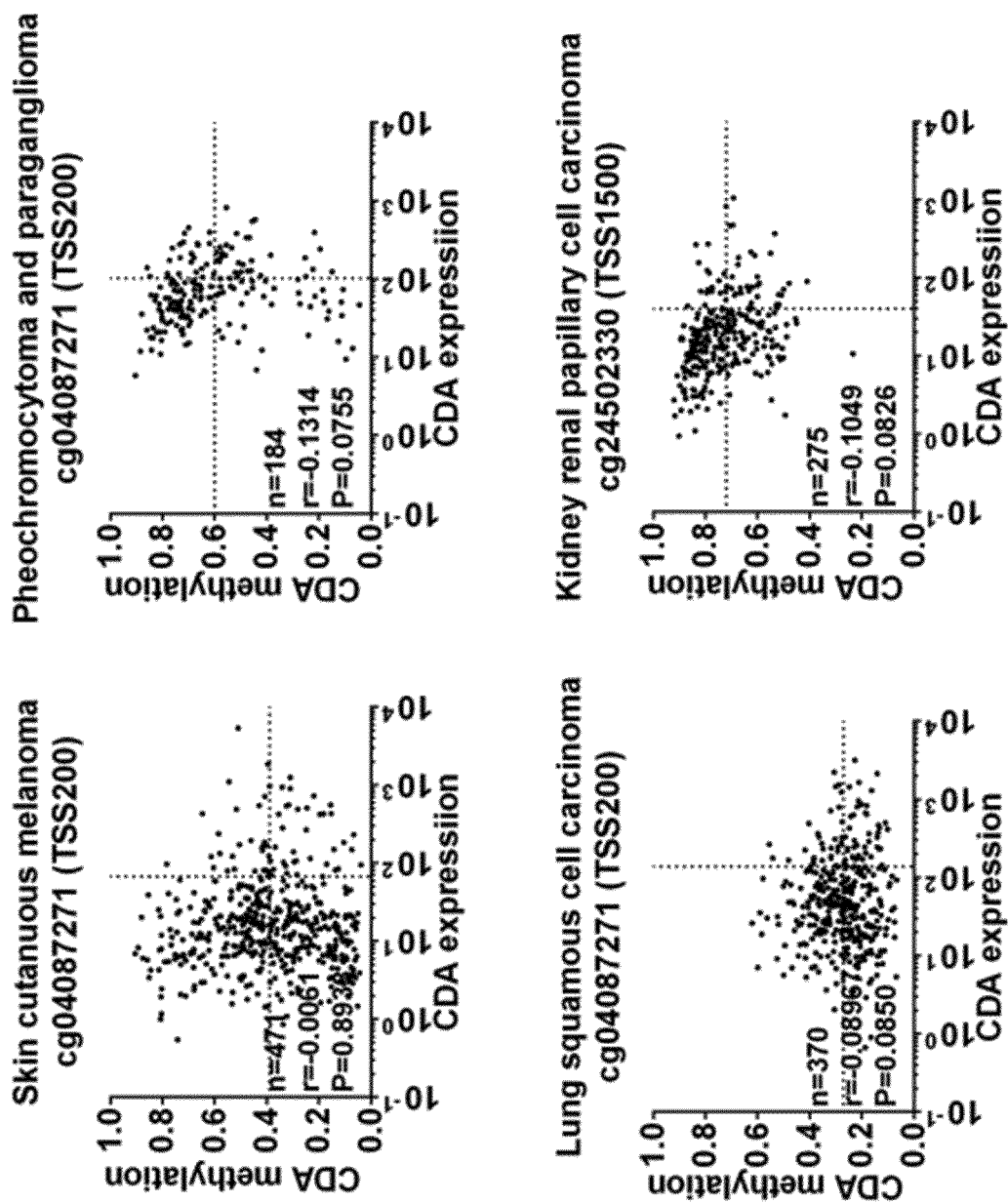
Figure 5 (following)

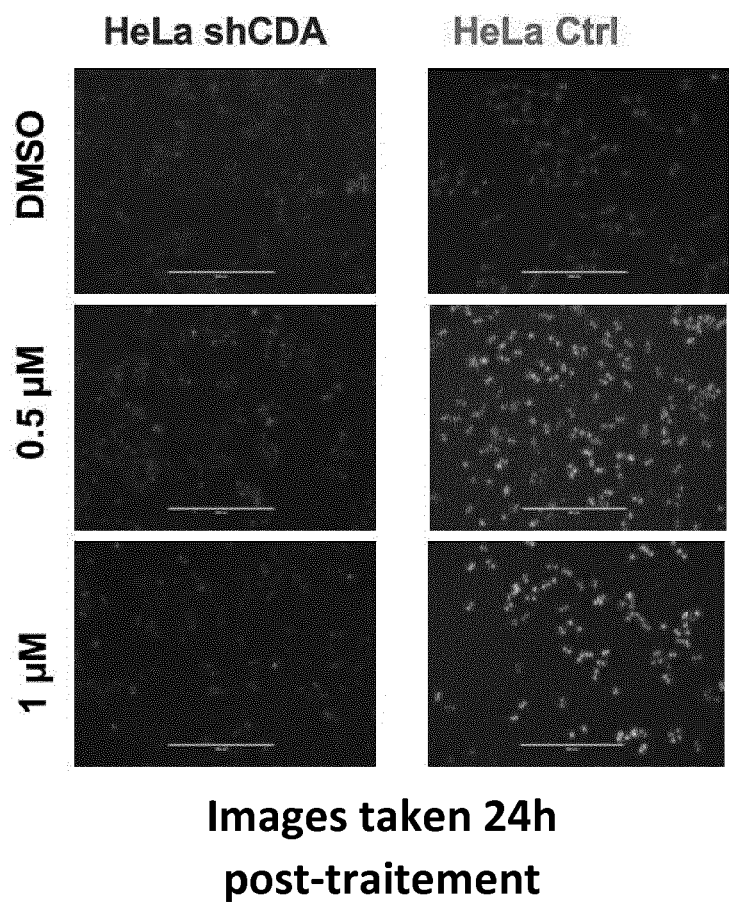
Images taken 24h post-traitement
Figure 7 (following)

Figure 9 (following)

A

B

CYTIDINE DEAMINASE EXPRESSION LEVEL IN CANCER AS A NEW THERAPEUTIC TARGET

CROSS-REFERENCE TO RELATED APPLICATION

This application is the U.S. national stage application of International Patent Application No. PCT/EP2017/057752, filed Mar. 31, 2017.

The Sequence Listing for this application is labeled "Seq-List.txt" which was created on Sep. 10, 2018 and is 4 KB. The entire content of the sequence listing is incorporated herein by reference in its entirety.

FIELD OF THE INVENTION

The present invention relates to the field of medicine, in particular of oncology. It concerns improvements in the treatment of cancer with high and low CDA (Cytidine Deaminase) expression level and the selection of patients for such treatments, kits and methods for screening compounds useful to improve treatment of cancer with high or low CDA expression level.

BACKGROUND OF THE INVENTION

Cancers as a group account for approximately 13% of all deaths each year with the most common being: lung cancer (1.4 million deaths), stomach cancer (740,000 deaths), liver cancer (700,000 deaths), colorectal cancer (610,000 deaths), and breast cancer (460,000 deaths). This makes cancer the leading cause of death in the developed world and the second leading cause of death in the developing world.

Despite major advances in the development of chemotherapy, many cancers continue to have a poor prognosis, due to the resistance of cancer cells to antineoplastic drugs through intrinsic or acquired mechanisms. Identification of the molecular mechanisms leading to resistance or sensitivity to a treatment is nowadays one of the main challenges in cancer therapy.

There is thus still a strong need to identify new markers allowing to predict the effectiveness of an antitumor compound on a given cancer and thereby to select the best treatment for the patient. The present invention seeks to meet these and other needs.

SUMMARY OF THE INVENTION

Cytidine deaminase (CDA) is an enzyme of the pyrimidine salvage pathway catalyzing the hydrolytic deamination of cytidine and deoxycytidine to uridine and deoxyuridine, respectively (Demontis S et al., Biochim Biophys Acta, 1998, 1443:323-33). CDA plays an important role in the sensitivity/resistance of cancer cells to treatment with cytidine analogs, and CDA overexpression has been reported to be a good marker for resistance to chemotherapy based on cytidine analogs (Neff T and Blau C A, Exp Hematol. 1996; 24:1340-6; Weizman N et al., Oncogene. 2014; 33:3812-9).

In this study, the inventors focused on CDA underexpression and CDA overexpression and identified new subgroups of cancers. Indeed, cancer expressing low level of CDA were susceptible to the specific toxic effects of a group of drugs such as aminoflavone (table 4) whereas cancer expressing high level of CDA were susceptible to the specific toxic effects of another group of drugs including dasatinib (table 3). Thus, CDA expression level can be used in cancer treatment as a new biomarker for selecting of the appropriate treatment.

Accordingly, in a first aspect, the present invention concerns an in vitro method for selecting a patient affected with a tumor for a treatment with an antitumor compound or for predicting the response of a patient affected with a tumor to a treatment with an antitumor compound, wherein the method comprises:

(a) measuring the expression level of CDA (Cytidine Deaminase) in a cancer sample from said patient, (b) comparing the CDA expression level of the cancer sample to a reference expression level, wherein a CDA expression level of the cancer sample lower than the reference expression level is predictive of the efficacy of a treatment with an antitumor compound selected from the group consisting of the compounds of table 4, and/or wherein a CDA expression level of the cancer sample higher than the reference expression level is predictive of the efficacy of a treatment with an antitumor compound selected from the group consisting of the compounds of table 3, (c) optionally, selecting patients with CDA expression level of their cancer sample lower than the reference expression level as suitable for a treatment with an antitumor compound selected from the group consisting of the compounds of table 4 and/or selecting patients with CDA expression level of their cancer sample higher than the reference expression level for a treatment with an antitumor compound selected from the group consisting of the compounds of table 3.

In a second aspect, the invention also concerns an antitumor compound selected from the group consisting of the compounds of table 4 for use in the treatment of a cancer in which CDA expression level is lower than a reference expression level.

In a third aspect, the invention also concerns an antitumor compound selected from the group consisting of the compounds of table 3 for use in the treatment of a cancer in which CDA expression level is higher than a reference expression level.

Preferably, the antitumor compound selected when CDA expression level is lower than the reference expression level is aminoflavone.

Preferably, the antitumor compound selected when CDA expression level is higher than the reference expression level is dasatinib.

Preferably, said cancer in which CDA expression level is lower than a reference expression level has a CDA expression level at least two times, preferably at least four times, less than the reference expression level, even more preferably said cancer do not express CDA.

Preferably, said cancer in which CDA expression level is higher than a reference expression level has a CDA expression level at least two times, preferably at least four times, even more preferably at least ten times, more than the reference expression level.

Preferably, the reference expression level is the expression level of CDA in a normal sample, preferably in a normal sample from the same tissue or a tissue counterpart, even more preferably in a normal sample from the same tissue or a tissue counterpart of the same patient.

The reference expression level can be the average of the expression level of CDA in normal samples from several patients.

Alternatively, the reference expression level is the expression level of CDA in a non-cancerous cell-line or the average of the CDA expression level of several non-cancerous cell-lines, preferably said cell-line(s) derivate(s) from the same tissue as the cancer sample.

The reference expression level may also be the average of the CDA expression levels of cancer samples from several patients, preferably cancer samples of the same tissue.

The expression level of CDA can be determined by measuring the quantity of CDA protein or CDA mRNA.

The tumor is a solid or a hematopoietic tumor, preferably a solid tumor.

Preferably, the cancer is selected from the group consisting of the prostate cancer, the lung cancer, the breast cancer, the gastric cancer, the kidney cancer, the ovarian cancer, the hepatocellular cancer, the osteosarcoma, the melanoma, the hypopharynx cancer, the esophageal cancer, the endometrial cancer, the cervical cancer, the pancreatic cancer, the liver cancer, the colon or colorectal cancer, the neuroendocrine tumors, the malignant tumor of the muscle, the adrenal cancer, the thyroid cancer, the uterine cancer, the skin cancer, the bladder cancer, the head and neck cancer, the lymphoma, and the leukemia.

The patient is an animal, preferably a mammal, even more preferably a human. Preferably, the patient is a new-born, a children or an adult, preferably an adult, even more preferably an adult of at least 50 years old.

In a fourth aspect, the invention also concerns an in vitro method for screening or identifying an antitumor compound suitable for treating a cancer in which CDA expression level is lower than a reference expression level comprising:

(a) providing a cancer cell in which CDA expression level is lower than a reference expression level, preferably a cancer cell which do not express CDA, (b) contacting said cancer cell with a test compound, (c) measuring the proliferation rate of said cancer cell, (d) comparing the proliferation rate of said cancer cell with a control condition wherein cells have not been contacted by the test compound, and (e) selecting the test compound which reduces the proliferation rate of said cancer cell in comparison with the control condition.

In a fifth aspect, the invention also concerns an in vitro method for screening or identifying an antitumor compound suitable for treating a cancer in which CDA expression level is higher than a reference expression level comprising:

(a) providing a cancer cell in which CDA expression level is higher than a reference expression level, preferably at least 4 times above, (b) contacting said cancer cell with a test compound, (c) measuring the proliferation rate of said cancer cell, (d) comparing the proliferation rate of said cancer cell with a control condition wherein cells have not been contacted by the test compound, and (e) selecting the test compound which reduces the proliferation rate of said cancer cell in comparison with the control condition.

Preferably, the reference expression level is the expression level of CDA in a non-cancerous cell or the average of the CDA expression level of several non-cancerous cells, preferably said cell(s) originate(s) from the same tissue as the cancer cell.

Alternatively, the reference expression level is the average of the CDA expression levels of cancer samples from several patients, preferably cancer samples of the same tissue as the cancer cell.

Preferably, the screening methods further comprises the selection of a test compound which do not reduce the proliferation rate of cells having a CDA expression level of about the reference expression level.

Preferably, the screening methods further comprise the selection of a test compound which do not reduce the proliferation rate of normal cells.

In a sixth aspect, the invention also concerns the use of the expression level of CDA as a marker for selecting a patient affected with a tumor for a treatment with an antitumor compound selected from the group consisting of the compounds of table 4 or with an antitumor compound selected from the group consisting of the compounds of table 3, or for predicting the efficacy of a treatment with an antitumor compound selected from the group consisting of the compounds of table 4 or with an antitumor compound selected from the group consisting of the compounds of table 3, wherein the CDA expression level of a cancer sample lower than the reference expression level being predictive of the efficacy of a treatment with an antitumor compound selected from the group consisting of the compounds of table 4, and wherein the CDA expression level of a cancer sample higher than the reference expression level being predictive of the efficacy of a treatment with an antitumor compound selected from the group consisting of the compounds of table 3.

In a seventh aspect, the invention also concerns the use of a kit for selecting a patient affected with a tumor for a treatment with an antitumor compound selected from the group consisting of the compounds of table 4 or with an antitumor compound selected from the group consisting of the compounds of table 3 and/or for predicting the efficacy of a treatment with an antitumor compound selected from the group consisting of the compounds of table 4 or with an antitumor compound selected from the group consisting of the compounds of table 3, and/or for screening or identifying an antitumor compound suitable for treating a cancer in which CDA expression level is lower than a reference expression level or an antitumor compound suitable for treating a cancer in which CDA expression level is higher than a reference expression level, wherein the kit comprises detection means selected from the group consisting of a pair of primers, a probe and an antibody specific to CDA, and a combination thereof, and, optionally, a leaflet providing guidelines to use such a kit.

DETAILED DESCRIPTION OF THE INVENTION

Figure 1:
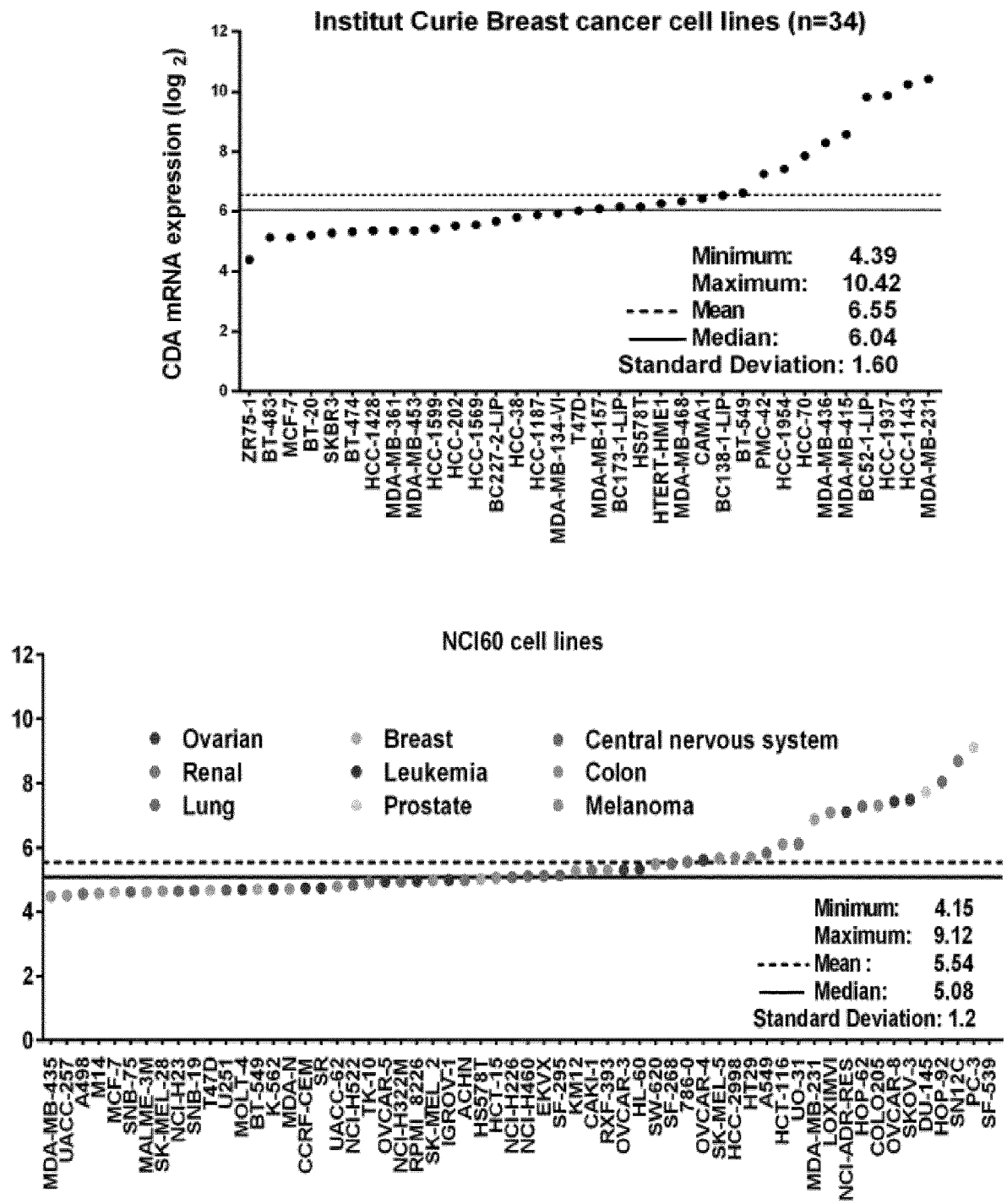
FIG. 1: CDA expression levels in cancer cell lines and tissues. A, Transcriptomic data sets in log 2 values for Curie Institute breast cancer cell lines (n=34) publicly available (see Materials and Methods section) (left panel) and from NCI 60 cancer cell lines data miner (33) (right panel). Mean and median values are shown as dashed and solid lines, respectively. B, Real-time RT-qPCR and western blot analysis of CDA expression in a set of 26 cell lines for three different cancers (breast, non-small lung and ovary) representative of the Curie Institute (left panel) and NCI60 (right panel) panels. Hsp90 and β-actin were used as loading controls for western blotting; TBP and GAPDH were used for RT-qPCR data normalization. Western blotting and RT-qPCR data were reproduced at least twice C, Real-time RT-qPCR quantification of CDA transcripts relative to TBP housekeeping gene transcripts in 66 breast-derived xenografts. D, IHC analysis of CDA expression in six different tumor tissues (n=50 per tissue). Representative images for each tissue (upper panels) and quantitative representations of CDA protein levels in each tissue (lower panels) are shown. The results are presented as percentages of tumors expressing low (black) and high (gray) levels of CDA on the basis of the scores obtained (Low: scores 0-1 and High: scores 2-3). For all images, the scale bar is 50 µm. The percentage of low-CDA cancer tissues is indicated in the black bars E, Scatter dot plot with mean±SD for transcriptomic data for CDA transcripts, comparing unmatched normal and tumor tissues for the liver (GSE14520), esophagus (GSE13898), cervix (GSE9750) and colon (GSE9348). The data were retrieved from the Nextbio (see Worldwide Web site: nextbio.com/b/nextbio.nb) and Oncomine (see Worldwide Website: oncomine.org) data sources and downloaded from GEO and presented as log 2 intensities. F, CDA transcript levels relative to TBP, as quantified by RT-qPCR in a mini-cohort of cancerous and non-cancerous colon tissues. Error bars indicate the SD. The P values calculated in unpaired two-tailed t-tests are considered statistically significant if <0.05.

The inventors have discovered that the CDA expression status of a cancer is of great importance for its treatment. Accordingly, they identified two new subgroups of cancers: CDA-deficient tumors and CDA-proficient tumors. Cancer expressing low level of CDA are susceptible to the specific toxic effects of a group of drugs as disclosed in table 4, such as aminoflavone, whereas cancer expressing high level of CDA are susceptible to the specific toxic effects of another group of drugs as disclosed in table 3, including dasatinib. Thus, CDA expression level can be used in cancer treatment as a new biomarker for selecting of the appropriate treatment.

Definitions

The term "cancer" or "tumor", as used herein, refers to the presence of cells possessing characteristics typical of cancer-causing cells, such as uncontrolled proliferation, and/or immortality, and/or metastatic potential, and/or rapid growth and/or proliferation rate, and/or certain characteristic morphological features. This term refers to any type of malignancy (primary or metastases) in any type of subject. It may refer to solid tumor as well as hematopoietic tumor.

The term "sample", as used herein, means any sample containing cells derived from a subject, preferably a sample which contains nucleic acids. Examples of such samples include fluids such as blood, plasma, saliva, urine and seminal fluid samples as well as biopsies, organs, tissues or cell samples. The sample may be treated prior to its use.

The term "cancer sample" refers to any sample containing tumoral cells derived from a patient, preferably a sample which contains nucleic acids. Preferably, the sample contains only tumoral cells.

The term "normal sample" refers to any sample which does not contain any tumoral cells. Preferably a normal sample is a healthy sample.

As used herein, the terms "subject", "individual" or "patient" are interchangeable and refer to an animal, preferably to a mammal, even more preferably to a human. However, the term "subject" can also refer to non-human animals, in particular mammals such as dogs, cats, horses, cows, pigs, sheep and non-human primates, among others.

As used herein, the term "marker" or "biomarker" refers to a measurable biological parameter that aid to predict the efficiency of a cancer treatment.

As used herein, the term "treatment", "treat" or "treating" refers to any act intended to ameliorate the health status of patients such as therapy, prevention, prophylaxis and retardation of the disease. In certain embodiments, such term refers to the amelioration or eradication of a disease or symptoms associated with a disease. In other embodiments, this term refers to minimizing the spread or worsening of the disease resulting from the administration of one or more therapeutic agents to a subject with such a disease.

The terms "quantity," "amount," and "level" are used interchangeably herein and may refer to an absolute quantification of a molecule in a sample, or to a relative quantification of a molecule in a sample, i.e., relative to another value such as relative to a reference value as taught herein.

As used herein, the terms "active principle", "active ingredient" "active pharmaceutical ingredient", "therapeutic agent", "antitumor compound", and "antitumor agent" are equivalent and refer to a component having a therapeutic effect.

As used herein, the term "therapeutic effect" refers to an effect induced by an active ingredient or by a pharmaceutical composition according to the invention, capable to prevent or to delay the appearance or the development of a cancer, or to cure or to attenuate the effects of a cancer.

As used herein, the term "effective amount" refers to a quantity of an active ingredient which prevents, removes or reduces the deleterious effects of the disease.

The methods of the invention, as disclosed below, may be in vivo, ex vivo or in vitro methods, preferably in vitro methods.

In a first aspect, the present invention concerns a method for selecting a patient affected with a tumor for a treatment with an antitumor compound or for predicting the response of a subject affected with a tumor to a treatment with an antitumor compound, wherein the method comprises:

(a) measuring the expression level of CDA (Cytidine Deaminase) in a cancer sample from said patient, (b) comparing the CDA expression level of the cancer sample to a reference expression level, wherein a CDA expression level of the cancer sample lower than the reference expression level is predictive of the efficacy of a treatment with an antitumor compound selected from the group consisting of the compounds of table 4, and/or wherein a CDA expression level of the cancer sample higher than the reference expression level is predictive of the efficacy of a treatment with an antitumor compound selected from the group consisting of the compounds of table 3, (c) optionally, selecting patients with CDA expression level of their cancer sample lower than the reference expression level as suitable for a treatment with an antitumor compound selected from the group consisting of the compounds of table 4 and/or selecting patients with CDA expression level of their cancer sample higher than the reference expression level as suitable for a treatment with an antitumor compound selected from the group consisting of the compounds of table 3.

Optionally, the method may further comprise a step of providing a cancer sample from said patient before the step (a).

Optionally, the method may further comprise a step of administering a therapeutically effective amount of a compound selected from the group consisting of the compounds of table 4 when patients have a CDA expression level of their cancer sample lower than the reference expression level and/or a therapeutically effective amount of a compound selected from the group consisting of the compounds of table 4 when patients have a CDA expression level of their cancer sample higher than the reference expression level.

In a particular aspect, the present invention also concerns a method for excluding a patient affected with a tumor for a treatment with an antitumor compound or for predicting that a subject affected with a tumor will not be responding to a treatment with an antitumor compound, wherein the method comprises:

(a) measuring the expression level of CDA (Cytidine Deaminase) in a cancer sample from said patient, (b) comparing the CDA expression level of the cancer sample to a reference expression level, wherein a CDA expression level of the cancer sample lower than the reference expression level is predictive of the inefficacy of a treatment with an antitumor compound selected from the group consisting of the compounds of table 3, and/or wherein a CDA expression level of the cancer sample higher than the reference expression level is predictive of the inefficacy of a treatment with an antitumor compound selected from the group consisting of the compounds of table 4, (c) optionally, excluding patients with CDA expression level of their cancer sample lower than the reference expression level for a treatment with an antitumor compound selected from the group consisting of the compounds of table 3 and/or excluding patients with CDA expression level of their cancer sample higher than the reference expression level for a treatment with an antitumor compound selected from the group consisting of the compounds of table 4.

Optionally, the method may further comprise a step of providing a cancer sample from said patient before the step (a).

In another particular aspect, the present invention also concerns a method for providing data useful for selecting a patient affected with a tumor for a treatment with an antitumor compound selected from the group consisting of the compounds of table 4 or with an antitumor compound selected from the group consisting of the compounds of table 3 or for determining whether a patient affected with a tumor is susceptible to benefit from a treatment with an antitumor compound selected from the group consisting of the compounds of table 4 or with an antitumor compound selected from the group consisting of the compounds of table 3, wherein the method comprises providing a cancer sample from said patient, determining the expression level of CDA in said sample, comparing the expression level of CDA to a reference expression level, wherein the under-expression of CDA is predictive that a treatment with an antitumor compound selected from the group consisting of the compounds of table 4 is indicated for said patient and optionally selecting patients with under-expression of CDA for a treatment with an antitumor compound selected from the group consisting of the compounds of table 4, and wherein the over-expression of CDA is predictive that a treatment with an antitumor compound selected from the group consisting of the compounds of table 3 is indicated for said patient and optionally selecting patients with over-expression of CDA for a treatment with an antitumor compound selected from the group consisting of the compounds of table 3.

In yet another particular aspect, the present invention also concerns a method for selecting a patient affected with a tumor for a treatment with an antitumor compound selected from the group consisting of the compounds of table 4 or for determining whether a patient affected with a tumor is susceptible to benefit from a treatment with an antitumor compound selected from the group consisting of the compounds of table 4, wherein the method comprises determining the expression level of CDA in a cancer sample from said patient, comparing the expression level of CDA to a reference expression level and optionally selecting patients with under-expression of CDA for a treatment with an antitumor compound selected from the group consisting of the compounds of table 4. Optionally, the method further comprises a previous step of providing a cancer sample from said patient.

In still another particular aspect, the present invention also concerns a method for selecting a patient affected with a tumor for a treatment with an antitumor compound selected from the group consisting of the compounds of table 3 or for determining whether a patient affected with a tumor is susceptible to benefit from a treatment with an antitumor compound selected from the group consisting of the compounds of table 3, wherein the method comprises determining the expression level of CDA in a cancer sample from said patient, comparing the expression level of CDA to a reference expression level and optionally selecting patients with over-expression of CDA for a treatment with an antitumor compound selected from the group consisting of the compounds of table 3. Optionally, the method further comprises a previous step of providing a cancer sample from said patient.

Cytidine Deaminase (CDA) Expression Level

The method of the invention comprise a first step of measuring the expression level of CDA in a cancer sample of a patient.

The terms "Cytidine deaminase", "Cytidine aminohydrolase", "Cytosine Nucleoside Deaminase", "Small Cytidine Deaminase", "CDD", "CDA", and "EC 3.5.4.5", as used herein, are equivalent and can be used one for the other. The term "Cytidine deaminase (CDA)" refers to the product of the CDA gene (Gene ID: 978, UniProtKB: P32320), it is an enzyme of the pyrimidine salvage pathway catalyzing the hydrolytic deamination of cytidine and deoxycytidine to uridine and deoxyuridine, respectively (Demontis S et al., Biochim Biophys Acta, 1998, 1443:323-33).

The expression level of CDA can be determined by a variety of techniques well known by the skilled person. In an embodiment, the expression level of CDA is determined by measuring the quantity of CDA protein or CDA mRNA.

In a particular embodiment, the expression level of CDA is determined by measuring the quantity of CDA protein. The quantity of CDA protein may be measured by any methods known by the skilled person. Usually, these methods comprise contacting the sample with a binding partner capable of selectively interacting with the CDA protein present in the sample. The binding partner is generally a polyclonal or monoclonal antibody, preferably monoclonal. Such an antibody can be produced through methods known to the man skilled in the art. This antibody includes in particular those produced by a hybridoma and those produced by genetic engineering using host cells transformed with a recombinant expression vector carrying a gene encoding the antibody. A hybridoma producing monoclonal antibodies can be obtained as following: CDA protein or immunogenic fragments thereof are used as antigen for immunisation according to conventional methods of immunisation. The resulting immunocytes are fused with known parent cells according to conventional cell fusion methods and the cells producing the antibodies are thus screened from fused cells by conventional screening methods. The invention concerns an antibody specific of human CDA or fragment thereof.

The quantity of CDA protein may be measured by semi-quantitative Western blots, enzyme-labeled and mediated immunoassays, such as ELISAs, biotin/avidin type assays, radioimmunoassay, immunoelectrophoresis or immunoprecipitation or by protein or antibody arrays. The protein expression level may be assessed by immunohistochemistry. The reactions generally include revealing labels such as fluorescent, chemiluminescent, radioactive, enzymatic labels or dye molecules, or other methods for detecting the formation of a complex between the antigen and the antibody or antibodies reacted therewith.

Preferably, the quantity of CDA protein is measured with a labeled binding partner, which is tetrahydrouridine (THU). Preferably, THU is radiolabeled. THU is used at a concentration comprised between about 0.001 mg/kg and about 100 mg/kg, preferably between about 0.1 mg/kg and about 10 mg/kg, even more preferably between about 0.1 mg/kg and about 2 mg/kg.

In the present document, the term «about» refers to a range of values of ±10% of the specified value. For example, «about 50» comprise values of ±10% of 50, i.e. values in the range between 45 and 55. Preferably, the term «about» refers to a range of values of ±5% of the specified value.

Accordingly, in a preferred embodiment, the present invention concerns a method for selecting a patient affected with a tumor for a treatment with an antitumor compound or for predicting the response of a subject affected with a tumor to a treatment with an antitumor compound, wherein the method comprises:

(a) measuring the expression level of CDA (Cytidine Deaminase) with THU, preferably a radiolabelled THU, in a cancer sample from said patient, (b) comparing the CDA expression level of the cancer sample to a reference expression level, wherein a CDA expression level of the cancer sample lower than the reference expression level is predictive of the efficacy of a treatment with an antitumor compound selected from the group consisting of the compounds of table 4, and/or wherein a CDA expression level of the cancer sample higher than the reference expression level is predictive of the efficacy of a treatment with an antitumor compound selected from the group consisting of the compounds of table 3, (c) optionally selecting patients with CDA expression level of their cancer sample lower than the reference expression level as suitable for a treatment with an antitumor compound selected from the group consisting of the compounds of table 4 and/or selecting patients with CDA expression level of their cancer sample higher than the reference expression level for a treatment with an antitumor compound selected from the group consisting of the compounds of table 3.

In another preferred embodiment, the invention also concerns a method for selecting a patient affected with a tumor for a treatment with an antitumor compound or for predicting the response of a subject affected with a tumor to a treatment with an antitumor compound, wherein the method comprises:

(a) measuring the expression level of CDA (Cytidine Deaminase) in a cancer sample from said patient by contacting said cancer sample with THU, preferably a radiolabelled THU, and detecting THU bound to CDA, (b) comparing the CDA expression level of the cancer sample to a reference expression level, wherein a CDA expression level of the cancer sample lower than the reference expression level is predictive of the efficacy of a treatment with an antitumor compound selected from the group consisting of the compounds of table 4, and/or wherein a CDA expression level of the cancer sample higher than the reference expression level is predictive of the efficacy of a treatment with an antitumor compound selected from the group consisting of the compounds of table 3, (c) optionally selecting patients with CDA expression level of their cancer sample lower than the reference expression level as suitable for a treatment with an antitumor compound selected from the group consisting of the compounds of table 4 and/or selecting patients with CDA expression level of their cancer sample higher than the reference expression level for a treatment with an antitumor compound selected from the group consisting of the compounds of table 3.

In another particular embodiment, the expression level of CDA is determined by measuring the quantity of CDA mRNA. Methods for determining the quantity of mRNA are well known in the art. mRNA can be detected by hybridization (e. g., Northern blot analysis) and/or amplification (e.g., RT-PCR). Preferably, mRNA is detected by quantitative or semi-quantitative RT-PCR. Real-time quantitative or semi-quantitative RT-PCR is particularly advantageous. Preferably, primer pairs were designed in order to overlap an intron. Other primers may be easily designed by the skilled person. Taqman probes specific of the CDA transcript may be used. Other methods of Amplification include ligase chain reaction (LCR), transcription-mediated amplification (TMA), strand displacement amplification (SDA) and nucleic acid sequence based amplification (NASBA).

In a preferred embodiment, the expression level of CDA is determined by measuring the quantity of CDA mRNA, preferably by quantitative or semi-quantitative RT-PCR or by real-time quantitative or semi-quantitative RT-PCR.

Comparison to a Reference Expression Level

The method of the invention comprise, in a second step, the comparison of the CDA expression level of the cancer sample to a reference expression level.

The reference expression level can be the CDA expression level in a normal sample or the average of the CDA expression levels of several normal samples.

In a particular embodiment, the reference expression level can be the expression level of CDA in a normal sample. Preferably, the normal sample is a sample from the same tissue as the cancer sample or a tissue counterpart, even more preferably the normal sample is a sample from the same tissue as the cancer sample or a tissue counterpart of the same patient. Accordingly, the method of the invention may further comprise a step of providing a normal sample from the patient prior to step (a).

In another particular embodiment, the reference expression level can be the average of the CDA expression levels of several normal samples, preferably from several patients. Preferably, these normal samples are samples from the same tissue as the cancer sample or a tissue counterpart.

Alternatively, the reference expression level is the expression level of CDA in a non-cancerous cell-line or the average of the CDA expression level of several non-cancerous cell-lines, preferably said cell-line(s) derivate(s) from the same tissue as the cancer sample.

Alternatively, the reference expression level may also be the average of the CDA expression levels of cancer samples from several patients, preferably cancer samples of the same tissue.

The expression level of CDA can be determined by measuring the quantity of CDA protein or CDA mRNA as described above.

Optionally, before to be compared with the reference expression level, the expression levels may be normalized using the expression level of an endogenous control gene having a stable expression in different cancer samples, such as RPLPO, RPL32, HPRT1, GAPDH, B2M, TBP and 18S genes.

CDA level expression is considered to be lower than the reference level or CDA is considered as under-expressed if the expression level of CDA in the tumor of the patient is, optionally after normalization, at least 5, 10, 20, 30, 40, 50, 60, 70, 80, 90, 95, 99% lower than the reference expression level.

Preferably, said cancer in which CDA expression level is lower than the reference expression level has a CDA expression level at least two times, preferably at least four times, more preferably at least six times, still preferably at least height time, less than the reference expression level, even more preferably said cancer do not express CDA.

CDA level expression is considered to be higher than the reference level or CDA is considered as over-expressed if the expression level of CDA in the tumor of the patient is, optionally after normalization, at least 5, 10, 20, 30, 40, 50, 60, 70, 80, 90, 100, 150, 200, 300, 400, 500, 600, 800, 1000% higher than the reference expression level.

Preferably, said cancer in which CDA expression level is higher than the reference expression level has a CDA expression level at least two times, preferably at least four times, more preferably at least six times, still preferably at least height time, yet preferably at least ten times, even more preferably at least twenty times higher than the reference expression level.

In a particular embodiment, the intensity of CDA expression level can be scored from 0 to 3. Scores of 0-1 are considered as low CDA expression level and scores of 2-3 are considered as high CDA expression level. This scoring can be based on immunohistochemistry analysis with a CDA specific antibody, as described, for example, in Baldeyron et al. (Mol Oncol, 2015, 9:1580-98) or in the Material and Method of example 1. A score of 0 corresponds to no staining, a score of 1 corresponds to a weak staining, a score of 2 corresponds to a moderate staining, and a score of 3 corresponds to an intense staining.

Antitumor Compounds

The method of the invention predict the efficiency of antitumor compounds according to the expression level of CDA in the cancer sample of a patient and thus allows to select patients for a treatment with these antitumor compounds.

A CDA expression level of the cancer sample higher than the reference expression level is predictive of the efficacy of a treatment with an antitumor compound selected from the group consisting of the compounds of table 3, derivatives and mixture thereof. Preferably, the antitumor compound is selected from the group consisting of the compounds of table 3 having the following NSC (National Safety Code) numbers: 1006486 (laurusin), 732192 (dipterocaprol (hydroxydammarenone-11)), 621867 (lestaurtinib), 259272 (ara-amp), 39367 (9-pentofuranosyl-6-(prop-2-en-1-ylsulfanyl)-9h-purine), 621864 (9-acetyl-9a-methoxy-1,2-dihydrocarbazol-3-one), 622155 (8,15-diisocyano-11(20)-amphilectene), 366140 (pyrazoloacridine), 341960 (psoralin, b-diethylamino-5-ethoxy-), 207111 (3(2h)-isothiazolone, (z)-2-butenedioate (2:1)), 120958 (furfuryladenosine), 312887 (fludarabine), 280594 (triciribine phosphate), 133115 (3-deazacytidine), 759877 (dasatinib), 102811 (formycin a), 726512 (phloeodictine A 1), 255523 (n6-benzyladenosine-5'-phosphate), 758896 (fluvastatin), 633781 (lovastatin), 699246 (1-(2-phenoxyethyl)-5-(3-methylphenylamino)uracil), 617595 (isoxazolyl-prodrug of distamycin (stallimycin)), derivatives and mixture thereof.

More preferably, the antitumor compound is selected from the group consisting of lestaurtinib, pyrazoloacridine, fludarabine, triciribine phosphate, dasatinib, derivatives and mixture thereof. Still preferably, the antitumor compound is selected from the group consisting of pyrazoloacridine, dasatinib, derivatives and mixture thereof. Alternatively, the antitumor compound is selected from the group consisting of the compounds of table 3 and is not a nucleotide analog, preferably the antitumor compound is selected from the group consisting of the compounds of table 3 having the following NSC numbers: 1006486 (laurusin), 732192 (dipterocaprol (hydroxydammarenone-11)), 621867 (lestaurtinib), 621864 (9-acetyl-9a-methoxy-1,2-dihydrocarbazol-3-one), 622155 (8,15-diisocyano-11(20)-amphilectene), 366140 (pyrazoloacridine), 341960 (psoralin, b-diethylamino-5-ethoxy-), 207111 (3(2h)-isothiazolone, (z)-2-butenedioate (2:1)), 759877 (dasatinib), 726512 (phloeodictine A 1), 758896 (fluvastatin), 633781 (lovastatin), 617595 (isoxazolyl-prodrug of distamycin (stallimycin)), derivatives and mixture thereof, more preferably, the antitumor compound is selected from the group consisting of lestaurtinib, pyrazoloacridine, dasatinib, derivatives and mixture thereof.

In a most preferred embodiment, the antitumor compound selected when CDA expression level is higher than the reference expression level is dasatinib.

A CDA expression level of the cancer sample lower than the reference expression level is predictive of the efficacy of a treatment with an antitumor compound selected from the group consisting of the compounds of table 4, derivatives and mixture thereof. Preferably, the antitumor compound is selected from the group consisting of the compounds of table 4 having the following NSC numbers: 733164 (5-hydroxyamino camptothecin), 341651 (senecioylchaparrin, 6-alpha-(b815099k220)), 737155 (borrelidin 3,11-bis-o-formyl ester), 638497 ((z) 4-acetoxy-3',4',5'-trimethoxystilbene), 124147 (harringtonine), 138780 (insariotoxin), 269756 (baccharinol), 5366 (noscapine), 710464 (AFP464, Aminoflavone), 66114 (physalin O), 328166 (8B-hydroxy-9B,10B-epoxyverrucarin A), 668382 (trihydroxy-azatoxin), 35676 (purpurogallin), 638492 ((z) 3,3',4,5-tetramethoxystilbene), 264880 (Dihydro-5-azacytidine), derivatives or mixture thereof.

In a most preferred embodiment, the antitumor compound selected when CDA expression level is lower than the reference expression level is aminoflavone.

Cancer

The method of the invention is aimed to select a patient affected with a tumor for a treatment.

The tumor can be a solid or a hematopoietic tumor. Preferably, the tumor is a solid tumor.

Preferably, the tumor is from a cancer selected from the group consisting of the prostate cancer, the lung cancer, the breast cancer, the gastric cancer, the kidney cancer, the ovarian cancer, the hepatocellular cancer, the osteosarcoma, the melanoma, the hypopharynx cancer, the esophageal cancer, the endometrial cancer, the cervical cancer, the pancreatic cancer, the liver cancer, the colon or colorectal cancer, the neuroendocrine tumors, the malignant tumor of the muscle, the adrenal cancer, the thyroid cancer, the uterine cancer, the skin cancer, the bladder cancer, the head and neck cancer, the lymphoma, and the leukemia.

More preferably, the tumor is from a cancer selected from the group consisting of the lung cancer, the breast cancer, the ovarian cancer, the melanoma, and the cervical cancer.

Even more preferably, the cancer is a breast cancer.

Patient, Regimen and Administration

The patient is an animal, preferably a mammal, even more preferably a human. However, the patient can also be a non-human animal, in particular mammals such as dogs, cats, horses, cows, pigs, sheep, donkeys, rabbits, ferrets, gerbils, hamsters, chinchillas, rats, mice, guinea pigs and non-human primates, among others, that are in need of treatment.

The human patient according to the invention may be a human at the prenatal stage, a new-born, a child, an infant, an adolescent or an adult, in particular an adult of at least 40 years old, preferably an adult of at least 50 years old, still more preferably an adult of at least 60 years old, even more preferably an adult of at least 70 years old.

Preferably, the patient has been diagnosed with a cancer.

In a particular embodiment, the patient has already received at least one line of treatment, preferably several lines of treatment.

The antitumor compound according to the invention can be administered by any conventional route of administration. The antitumor compound can be formulated for a topical, enteral, oral, parenteral, intranasal, intravenous, intramuscular, subcutaneous or intraocular administration and the like.

Preferably, the treatment with the antitumor compound start no longer than a month, preferably no longer than a week, after the determination of the CDA expression level.

The antitumor compound according to the invention may be administered as a single dose or in multiple doses.

Preferably, the treatment is administered regularly, preferably between every day and every month, more preferably between every day and every two weeks, even more preferably between every day and every week.

The duration of treatment with the antitumor compound according to the invention is preferably comprised between 1 day and 24 weeks, more preferably between 1 day and 10 weeks, even more preferably between 1 day and 4 weeks. In a particular embodiment, the treatment last as long as the cancer persists.

The amount of antitumor compound according to the invention to be administered has to be determined by standard procedure well known by those of ordinary skills in the art. Physiological data of the patient (e.g. age, size, weight, and physical general condition) and the routes of administration have to be taken into account to determine the appropriate dosage, so as a therapeutically effective amount will be administered to the patient.

In a particular embodiment, the dose of aminoflavone for each administration is comprised between about 1 $mg/m^2$ and 100 $mg/m^2$, preferably between about 10 $mg/m^2$ and about 50 $mg/m^2$, even more preferably between about 10 $mg/m^2$ and about 27 $mg/m^2$.

In another particular embodiment, the dose of dasatinib for each administration is comprised between about 1 mg and about 1000 mg, preferably between about 10 mg and about 250 mg, even more preferably between 20 mg and 180 mg. Preferably, one dose of dasatinib is administered daily.

CDA Regulating Agents

As used herein, the term "CDA regulating agent" refers to a compound able to modify the expression level and/or the activity of CDA. A CDA regulating agent according to the invention can be a CDA enhancing agent or a CDA repressing agent. As used herein, the term "CDA enhancing agent" refers to molecules that increase the expression level and/or the activity of CDA. As used herein, the term "CDA repressing agent", refers to molecules that decrease the expression level and/or the activity of CDA.

Preferably, CDA enhancing agents according to the invention are selected from the group consisting of vorinostat and DNA demethylating agents, preferably selected from the group consisting of 5-azacytidine (also known as azacitidine or 5-aza), 5-azadeoxycytidine (also known as decitabine or 5-aza-dC), procaine, and a mixture thereof. In a preferred embodiment, the CDA enhancing agent is vorinostat or 5-azadeoxycytidine, even more preferably the CDA enhancing agent is 5-azadeoxycytidine. Alternatively, the CDA enhancing agent is an expression vector allowing the expression of recombinant CDA in the target cells, in particular cancerous cells. Alternatively, the CDA enhancing agent is a molecule inhibiting the activity or the expression of the Estrogen Receptor 1 (ESR1). The molecule inhibiting the activity or expression of ESR1 can be an inhibitor of ESR1, such as the fulvestran, or an inhibitor of the expression of the ERS1 gene, such as a siRNA targeting the expression of the ESR1 gene.

Preferably, the CDA repressing agent is a cytidine deaminase inhibitor, preferably THU (tetrahydrouridine). Alternatively, the CDA repressing agent is a siRNA targeting the expression of CDA.

In a particular aspect, the invention relates to a method for selecting a patient affected with a tumor for a treatment with a combination of a CDA enhancing agent and an antitumor compound selected from the group consisting of the compounds of table 3, wherein the method comprises:

(a) measuring the expression level of CDA (Cytidine Deaminase) in a cancer sample from said patient, (b) comparing the CDA expression level of the cancer sample to a reference expression level, wherein a CDA expression level of the cancer sample lower or less than two times higher than the reference expression level is predictive of the efficacy of a treatment with a combination of a CDA enhancing agent, preferably a DNA demethylating agent, more preferably 5-azadeoxycytidine, and an antitumor compound selected from the group consisting of the compounds of table 3, preferably dasatinib.

(c) optionally, selecting patients with CDA expression level of their cancer sample lower or less than two times higher than the reference expression level as suitable for a treatment with a combination of a CDA enhancing agent, preferably a DNA demethylating agent, more preferably 5-azadeoxycytidine, and an antitumor compound selected from the group consisting of the compounds of table 3, preferably dasatinib.

In another particular aspect, the invention relates to a pharmaceutical composition comprising a CDA enhancing agent, preferably a DNA demethylating agent, more preferably 5-azadeoxycytidine, and an antitumor compound selected from the group consisting of the compounds of table 3, preferably dasatinib, for use in the treatment of a cancer, preferably a cancer having a low CDA expression level when compared to a reference expression level or a CDA expression level less than two times higher than the reference expression level.

In still another particular aspect, the invention also refers to a product or kit containing (a) a CDA enhancing agent, preferably a DNA demethylating agent, more preferably 5-azadeoxycytidine, and (b) an antitumor compound selected from the group consisting of compounds of table 3, preferably dasatinib, as a combined preparation for simultaneous, separate or sequential use, in particular in the treatment of cancer, preferably a cancer having a low CDA expression level when compared to a reference expression level or a CDA expression level less than two times higher than the reference expression level.

The dose of 5-azadeoxycytidine for each administration to a patient is comprised between about 0.1 mg/kg and about 50 mg/kg, preferably between about 1 mg/kg and about 20 mg/kg.

In another particular aspect, the invention relates to an in vitro method for selecting a patient affected with a tumor for a treatment with a combination of a CDA enhancing agent, preferably a DNA demethylating agent, and a nucleoside analog, wherein the method comprises:

(a) measuring the expression level of CDA (Cytidine Deaminase) in a cancer sample from said patient, (b) comparing the CDA expression level of the cancer sample to a reference expression level, wherein a CDA expression level of the cancer sample lower or less than two times higher than the reference expression level is predictive of the efficacy of a treatment with a combination of a CDA enhancing agent, preferably a DNA demethylating agent, more preferably 5-azadeoxycytidine, and a nucleoside analog, (c) optionally, selecting patients with CDA expression level of their cancer sample lower or less than two times higher than the reference expression level as suitable for a treatment with a combination of a CDA enhancing agent, preferably DNA demethylating agent, more preferably 5-azadeoxycytidine, and a nucleoside analog.

In still another particular aspect, the invention relates to a pharmaceutical composition comprising a CDA enhancing agent, preferably a DNA demethylating agent, more preferably 5-azadeoxycytidine, and a nucleoside analog, for use in the treatment of a cancer, preferably a cancer having a low CDA expression level when compared to a reference expression level or a CDA expression level less than two times higher than the reference expression level.

In yet another particular aspect, the invention also refers to a product or kit containing (a) a CDA enhancing agent, preferably a DNA demethylating agent, more preferably 5-azadeoxycytidine, and (b) a nucleoside analog, as a combined preparation for simultaneous, separate or sequential use, in particular in the treatment of cancer, preferably a cancer having a low CDA expression level when compared to a reference expression level or a CDA expression level less than two times higher than the reference expression level.

Preferably, the nucleoside analog is an oxidized and/or epigenetically modified cytidine nucleoside, more preferably the nucleoside agent is cytosine arabinoside, gemcitabine, or a combination thereof.

The dose of 5-azadeoxycytidine for each administration to a patient is comprised between 1 about 0.1 mg/kg and about 50 mg/kg, preferably between about 1 mg/kg and about 20 mg/kg.

In yet another particular aspect, the invention relates to an in vitro method for selecting a patient affected with a tumor for a treatment with a combination of a CDA enhancing agent, preferably a DNA demethylating agent, more preferably 5-azadeoxycytidine, an antitumor compound selected from the group consisting of the compounds of table 3, preferably dasatinib, and a nucleoside analog, wherein the method comprises:

(a) measuring the expression level of CDA (Cytidine Deaminase) in a cancer sample from said patient, (b) comparing the CDA expression level of the cancer sample to a reference expression level, wherein a CDA expression level of the cancer sample lower or less than two times higher than the reference expression level is predictive of the efficacy of a treatment with said combination, (c) optionally, selecting patients with CDA expression level of their cancer sample lower than the reference expression level as suitable for a treatment with said combination.

In another particular aspect, the invention relates to a pharmaceutical composition comprising a CDA enhancing agent, preferably a DNA demethylating agent, more preferably 5-azadeoxycytidine, an antitumor compound selected from the group consisting of the compounds of table 3, preferably dasatinib, and a nucleoside analog, for use in the treatment of a cancer, preferably a cancer having a low CDA expression level when compared to a reference expression level or a CDA expression level less than two times higher than the reference expression level.

In still another particular aspect, the invention also refers to a product or kit containing (a) a CDA enhancing agent, preferably a DNA demethylating agent, more preferably 5-azadeoxycytidine, (b) an antitumor compound selected from the group consisting of the compounds of table 3, preferably dasatinib, and (c) a nucleotide analog, as a combined preparation for simultaneous, separate or sequential use, in particular in the treatment of cancer, preferably a cancer having a low CDA expression level when compared to a reference expression level or a CDA expression level less than two times higher than the reference expression level.

Preferably, the nucleoside analog is an oxidized and/or epigenetically modified cytidine nucleoside, more preferably the nucleoside agent is cytosine arabinoside, gemcitabine, or a combination thereof.

The dose of 5-azadeoxycytidine for each administration to a patient is comprised between about 0.1 mg/kg and about 50 mg/kg, preferably between about 1 mg/kg and about 20 mg/kg.

In yet another particular aspect, the invention relates to a method for selecting a patient affected with a tumor for a treatment with a combination of a CDA repressing agent and an antitumor compound selected from the group consisting of the compounds of table 4, wherein the method comprises:

(a) measuring the expression level of CDA (Cytidine Deaminase) in a cancer sample from said patient, (b) comparing the CDA expression level of the cancer sample to a reference expression level, wherein a CDA expression level of the cancer sample higher or less than two times lower than the reference expression level is predictive of the efficacy of a treatment with a combination of a CDA repressing agent, preferably THU, and an antitumor compound selected from the group consisting of the compounds of table 4, preferably aminoflavone, (c) optionally, selecting patients with CDA expression level of their cancer sample higher or less than two times lower than the reference expression level as suitable for a treatment with a combination of a CDA repressing agent, preferably THU, and an antitumor compound selected from the group consisting of the compounds of table 4, preferably aminoflavone.

In another particular aspect, the invention relates to a pharmaceutical composition comprising a CDA repressing agent, preferably THU, and an antitumor compound selected from the group consisting of the compounds of table 4, preferably aminoflavone, for use in the treatment of a cancer, preferably a cancer having a high CDA expression level when compared to a reference expression level or a CDA expression level less than two times lower than the reference expression level.

In still another particular aspect, the invention also refers to a product or kit containing (a) a CDA repressing agent, preferably THU, and (b) an antitumor compound selected from the group consisting of the compounds of table 4, preferably aminoflavone, as a combined preparation for simultaneous, separate or sequential use, in particular in the treatment of cancer, preferably a cancer having a high CDA expression level when compared to a reference expression level or a CDA expression level less than two times lower than the reference expression level.

The dose of THU for each administration to a patient is comprised between about 0.1 mg/kg and 100 mg/kg, preferably between about 1 mg/kg and about 50 mg/kg, more preferably between 5 mg/kg and 20 mg/kg.

All the embodiments disclosed above are also contemplated in the products, treatment methods, screening methods, kits and uses below.

Use of an Antitumor Compound and Treatment Methods

In a particular aspect, the invention also concerns an antitumor compound selected from the group consisting of the compounds of table 4, preferably aminoflavone, for use in the treatment of a cancer in which CDA expression level is lower than a reference expression level.

The present invention also concerns the use of an antitumor compound selected from the group consisting of the compounds of table 4, preferably aminoflavone, for the manufacture of a medicament for treating a cancer in which CDA expression level is lower than a reference expression level.

The invention also relates to a method for treating a patient affected with a cancer in which CDA expression level is lower than a reference expression level, wherein the method comprises a step of administrating an antitumor compound selected from the group consisting of the compounds of table 4, preferably aminoflavone, to said patient.

In another aspect, the invention also relates to a combination of a repressing agent, preferably THU, and an antitumor compound selected from the group consisting of the compounds of table 4, preferably aminoflavone, for use in the treatment of a cancer in which CDA expression level is higher or less than two times lower than a reference expression level.

The present invention also concerns the use of a combination of a CDA repressing agent, preferably THU, and an antitumor compound selected from the group consisting of the compounds of table 4, preferably aminoflavone, for the manufacture of a medicament for treating a cancer in which CDA expression level is higher or less than two times lower than a reference expression level.

The invention also relates to a method for treating a patient affected with a cancer in which CDA expression level is higher or less than two times lower than a reference expression level, wherein the method comprises a step of administrating a combination of a repressing agent, preferably THU, and an antitumor compound selected from the group consisting of the compounds of table 4, preferably aminoflavone, to said patient.

In another aspect, the invention also concerns an antitumor compound selected from the group consisting of the compounds of table 3, preferably dasatinib, for use in the treatment of a cancer in which CDA expression level is higher than a reference expression level.

The present invention also concerns the use of an antitumor compound selected from the group consisting of the compounds of table 3, preferably dasatinib, for the manufacture of a medicament for treating a cancer in which CDA expression level is higher than a reference expression level.

The invention also relates to a method for treating a patient affected with a cancer in which CDA expression level is higher than a reference expression level, wherein the method comprises a step of administrating an antitumor compound selected from the group consisting of the compounds of table 3, preferably dasatinib, to said patient.

In yet another aspect, the invention also relates to a combination of a CDA enhancing agent, preferably a DNA demethylating agent, and an antitumor compound selected from the group consisting of the compounds of table 3, preferably dasatinib, for use in the treatment of a cancer in which CDA expression level is lower or less than two times higher than a reference expression level.

The present invention also concerns the use of a combination of a CDA enhancing agent, preferably a DNA demethylating agent, and an antitumor compound selected from the group consisting of the compounds of table 3, preferably dasatinib, for the manufacture of a medicament for treating a cancer in which CDA expression level is lower or less than two times higher than a reference expression level.

The invention also relates to a method for treating a patient affected with a cancer in which CDA expression level is lower or less than two times higher than a reference expression level, wherein the method comprises a step of administrating a combination of a CDA enhancing agent, preferably a DNA demethylating agent, and an antitumor compound selected from the group consisting of the compounds of table 3, preferably dasatinib, to said patient.

In still another aspect, the invention also relates to a combination of a CDA enhancing agent, preferably a DNA demethylating agent, and a nucleoside analog, for use in the treatment of a cancer in which CDA expression level is lower or less than two times higher than a reference expression level.

The present invention also concerns the use of a combination of a CDA enhancing agent, preferably a DNA demethylating agent, and a nucleoside analog, for the manufacture of a medicament for treating a cancer in which CDA expression level is lower or less than two times higher than a reference expression level.

The invention also relates to a method for treating a patient affected with a cancer in which CDA expression level is lower or less than two times higher than a reference expression level, wherein the method comprises a step of administrating a combination of a CDA enhancing agent, preferably a DNA demethylating agent, and a nucleoside analog to said patient.

In another aspect, the invention also relates to a combination of a CDA enhancing agent, preferably a DNA demethylating agent, an antitumor compound selected from the group consisting of the compounds of table 3, preferably dasatinib, and a nucleoside analog, for use in the treatment of a cancer in which CDA expression level is lower or less than two times higher than a reference expression level.

The present invention also concerns the use of a combination of a CDA enhancing agent, preferably a DNA demethylating agent, an antitumor compound selected from the group consisting of the compounds of table 3, preferably dasatinib, and a nucleoside analog, for the manufacture of a medicament for treating a cancer in which CDA expression level is lower or less than two times higher than a reference expression level.

The invention also relates to a method for treating a patient affected with a cancer in which CDA expression level is lower or less than two times higher than a reference expression level, wherein the method comprises a step of administrating a combination of a CDA enhancing agent, preferably a DNA demethylating agent, an antitumor compound selected from the group consisting of the compounds of table 3, preferably dasatinib, and a nucleoside analog to said patient.

Screening Methods

In another aspect, the invention also concerns a method for screening or identifying an antitumor compound suitable for treating a cancer in which the CDA expression level is lower than a reference expression level comprising:
 (a) providing a cancer cell in which CDA expression level is lower than a reference expression level, preferably a cancer cell which do not express CDA,
 (b) contacting said cancer cell with a test compound,
 (c) measuring the proliferation rate of said cancer cell,
 (d) comparing the proliferation rate of said cancer cell with a control condition wherein cells have not been contacted by the test compound, and
 (e) selecting the test compound which reduces the proliferation rate of said cancer cell in comparison with the control condition.

In yet another aspect, the invention also concerns a method for screening or identifying an antitumor compound suitable for treating a cancer in which CDA expression level is higher than a reference expression level comprising:
 (a) providing a cancer cell in which CDA expression level is higher than a reference expression level, preferably at least 4 times above,
 (b) contacting said cancer cell with a test compound,
 (c) measuring the proliferation rate of said cancer cell,
 (d) comparing the proliferation rate of said cancer cell with a control condition wherein cells have not been contacted by the test compound, and
 (e) selecting the test compound which reduces the proliferation rate of said cancer cell in comparison with the control condition.

Preferably, the reference expression level is the expression level of CDA in a non-cancerous cell or the average of the CDA expression level of several non-cancerous cells, preferably said cell(s) originate(s) from the same tissue as the cancer cell.

Alternatively, the reference expression level is the average of the CDA expression levels of cancer samples from several patients, preferably cancer samples of the same tissue as the cancer cell.

Preferably, the screening methods further comprises the selection of a test compound which do not reduce the proliferation rate of cells having a CDA expression level of about the reference expression level.

Preferably, the screening methods further comprises the selection of a test compound which do not reduce the proliferation rate of normal cells.

Use as a Marker

In another aspect, the invention also concerns the use of the expression level of CDA as a marker for selecting a patient affected with a tumor for a treatment with an antitumor compound selected from the group consisting of the compounds of table 4 or with an antitumor compound selected from the group consisting of the compounds of table 3, or for predicting the efficacy of a treatment with an antitumor compound selected from the group consisting of the compounds of table 4 or with an antitumor compound selected from the group consisting of the compounds of table 3, wherein the CDA expression level of a cancer sample lower than the reference expression level being predictive of the efficacy of a treatment with an antitumor compound selected from the group consisting of the compounds of table 4, and wherein the CDA expression level of a cancer sample higher than the reference expression level being predictive of the efficacy of a treatment with an antitumor compound selected from the group consisting of the compounds of table 3.

In yet another aspect, the invention also concerns the use of the expression level of CDA as a marker for selecting a patient affected with a tumor for a treatment with a combination of a CDA expression level increasing agent, preferably a DNA demethylating agent, an antitumor compound selected from the group consisting of the compounds of table 3, preferably dasatinib, and/or a nucleoside analog, or for predicting the efficacy of a treatment with a combination of a CDA expression level increasing agent, preferably a DNA demethylating agent, an antitumor compound selected from the group consisting of the compounds of table 3, preferably dasatinib, and/or a nucleoside analog, wherein the CDA expression level of a cancer sample lower or less than two times higher than the reference expression level being predictive of the efficacy of a treatment with a combination of CDA expression level increasing agent, preferably a DNA demethylating agent, an antitumor compound selected from the group consisting of the compounds of table 3, preferably dasatinib, and a nucleoside analog.

In still another aspect, the invention also concerns the use of the expression level of CDA as a marker for selecting a patient affected with a tumor for a treatment with a combination of a CDA expression level decreasing agent, preferably THU, and an antitumor compound selected from the group consisting of the compounds of table 4, preferably aminoflavone, or for predicting the efficacy of a treatment with a combination of a CDA expression level decreasing agent, preferably THU, an antitumor compound selected from the group consisting of the compounds of table 4, preferably aminoflavone, wherein the CDA expression level of a cancer sample higher or less than two times lower than the reference expression level being predictive of the efficacy of a treatment with a combination of CDA expression level increasing agent, preferably THU, and an antitumor compound selected from the group consisting of the compounds of table 4, preferably aminoflavone.

Kits

In another aspect, the invention also concerns the use of a kit for selecting a patient affected with a tumor for a treatment with an antitumor compound selected from the group consisting of the compounds of table 4 or with an antitumor compound selected from the group consisting of the compounds of table 3 and/or for predicting the efficacy of a treatment with an antitumor compound selected from the group consisting of the compounds of table 4 or with an antitumor compound selected from the group consisting of the compounds of table 3, and/or for screening or identifying an antitumor compound suitable for treating a cancer in which CDA expression level is lower than a reference expression level or an antitumor compound suitable for treating a cancer in which CDA expression level is higher than a reference expression level, wherein the kit comprises detection means selected from the group consisting of a pair of primers, a probe and an antibody specific to CDA or a radiolabelled THU, and a combination thereof, and, optionally, a leaflet providing guidelines to use such a kit.

All the references cited in this application, including scientific articles and summaries, published patent applications, granted patents or any other reference, are entirely incorporated herein by reference, which includes all the results, tables, figures and texts of theses references.

Although having different meanings, the terms "comprising", "having", "consisting in" and "containing" can be replaced one for the other in the entire application.

Further aspects and advantages of the present invention will be described in the following examples, which should be regarded as illustrative and not limiting.

EXAMPLES

Example 1

Materials and Methods

Cell Culture and Treatments

The inventors used 33 cancer cell lines in this study (cf. Table 5): 19 breast cancer cell lines from the Translational Research Department of the Curie Institute (ZR75-1, T47D, HCC-1428, BT-474, MCF-7, MDA-MB-361, MDA-MB-468, MDA-MB-231, MDA-MB-436, HCC-38, HCC-70, HCC-1187, HCC-1937, HCC-1143, BT-20, BT-549, HCC-1954, SKBR-3, HS578T) and two nonmalignant breast cell lines (MCF-12A and 184B5), four lung cancer cell lines (H522, H23, HOP-92, HOP-62), three ovarian cancer cell lines (IGROV-1 SKOV-3 and OVCAR-8) from the NCI, one melanoma cell line (A2058) from Dr. Stephan Vagner's laboratory (UMR3348 CNRS, Curie Institute), and two cervical cancer cell lines (HeLa-Ctrl and HeLa-shCDA) and two Bloom syndrome cell lines (BS-Ctrl and BS-CDA), previously described (cf. Reference 5).

All cells were routinely checked for the absence of mycoplasma and were maintained in the recommended media (cf. Table 5) before the extraction of DNA, RNA and proteins.

For evaluation of the induction of CDA expression, RNA was isolated from cell lines continuously treated with 1 or 2.5 µM of 5-Aza-2'-deoxycytidine (5-Aza-dC—Sigma Aldrich) for 96 hours.

Cell viability was carried out with 3-(4,5-dimethyl-2-thiazolyl)-2,5 diphenyl-2H-tetrazolium bromide (MTT-Life Technologies) in 96-well microplates. The functionality of CDA was assessed by plating HCC-1954 and IGROV-1 cells at densities of 2000 and 3000 cells/well, respectively, on the day before pretreatment and at a density of 800 cells/well for control conditions. Cells were then left untreated or subjected to pretreatment with 1 µM 5-Aza-dC for 96 h. The cells were washed twice with PBS buffer, placed in fresh medium and incubated for 72 hours in the presence of various concentrations of gemcitabine, from 0.001 to 1 µM (Sigma Aldrich). The data were normalized to corresponding controls, for each condition. Aminoflavone cytotoxicity was evaluated after 72 h of treatment, by plating MCF-7, MDA-MB-468, MDA-MB-231, SKOV-3, and OVCAR-8 cells at a density of 3000 cells/well and IGROV-1 cells at a density of 4000 cells/well. Aminoflavone (NSC 686288) was provided by Dr Yves Pommier (Developmental Therapeutics Branch—NCI).

DNA Sequencing, Quantitative PCR and Western Blotting

The 950 base pairs downstream from the translation initiation codon in the CDA promoter region and the four exons were amplified by PCR, with the Phusion Polymerase enzyme (Promega). The reaction was performed with 50 ng of genomic DNA isolated from 12 breast cancer and two normal-like cell lines. The specific primers used for amplification and nucleotide sequencing to base-pair resolution (Eurofins Genomics) are presented in Table 6.

The procedure for real-time PCR (RT-qPCR) was as described by Gemble et al. (cf. Reference 19). In brief, total RNA was extracted from PDX tissues and from cell lines with the RNeasy Mini Kit (Qiagen). Reverse transcription was performed on 1 µg of RNA with the GoScript enzyme (Promega). The cDNA obtained was used at a dilution of 1/10 for real-time PCR with the SYBER Green supermix reagent (Biorad) in a Biorad CFX96 machine. Each sample was run in triplicate. Relative expression was determined by the $2^{-\Delta\Delta Ct}$ method. GAPDH and TBP were used as internal controls. The specific primers used for RT-qPCR analysis are presented in Table 7.

For western blotting, cells were harvested by centrifugation and lysed in 8 M urea, 50 mM Tris-HCl, pH 7.5 and 150 mM β-mercaptoethanol buffer supplemented with protease inhibitor (ThermoScientific). They were then sonicated and heated. Protein concentration was estimated with the BCA kit (Pierce) and the equivalent of 20 µg or protein per cell lysate was run on a 4-12% Bis-Tris pre-cast gel (Life Technologies). The proteins were then transferred to PVDF membranes, which were probed with the appropriate antibody. Protein bands were visualized with a CCD camera (BioRad). Details of the primary and secondary antibodies used are provided in Table 8.

Immunohistochemistry

Immunohistochemistry was carried out as described by Baldeyron et al. (21). Briefly, paraffin-embedded tissue blocks obtained at the initial diagnosis were retrieved from the archives of the Biopathology Department of Curie Institute Hospital. Sections (3 µm thick) were cut with a microtome from the paraffin-embedded tissue blocks. Tissue sections were dewaxed and rehydrated through a series of xylene and ethanol washes. A primary anti-CDA antibody (Ab) was used (cf. Table 9). The sections were processed with a Dako machine for immunostaining. The specificity of the CDA Ab was confirmed by applying the same protocol to paraffin-embedded human tissue sections and cell block sections. The sections were rehydrated by incubation in PBS for 5 minutes and then incubated with anti-CDA antibody for 1 hour. Antibody binding was detected by incubation with a secondary antibody coupled to a peroxidase-conjugated polymer (Dako Envision +) after treatment with DAB solution (Dako K3468) for 5 minutes, and Mayer's hematoxylin for 1 minute. The sections were then mounted in resin. We evaluated CDA immunostaining on histological sections from 19 normal human tissues (20 samples per tissue) (FIG. 4D), and from 6 primary tumor tissues (50 samples per cancer type) (FIG. 1D). For each section we evaluated two immunohistological scores:

Intensity score: Score 0: no staining, Score 1+: weak staining, Score 2+: moderate staining, Score 3+: intense staining.

Frequency score: Score 0: no staining, Score 1+: 1%-33% stained cells, Score 2+: 34%-67% stained cells, Score 3+: 68%-100% stained cells.

Then we defined a final score (H score=frequency score× intensity score).

This H score was equal to 1 in normal colon tissue, and 1.5 in lung, breast, melanoma, ovary and endometrium normal tissues. It means that the expression of CDA in normal tissues is between $\geq 1$ and $<2$.

Thus, the cut-off of CDA expression in tumor tissues was defined as: CDA under-expression by H score between 0 and 1 (CDA low), and CDA overexpression by H score between 2 and 3 (CDA high). Thus, the data are presented as a combination of the percentage of CDA-positive cells and intensity scores. The analysis was carried out by two independent pathologists.

Breast Cancer Patient-Derived Xenografts

The PDX models used here were established as described by Marangoni et al. (cf. Reference 21). Briefly, breast cancer fragments were obtained from patients at the time of surgery, with the prior written informed consent of the patients. Fragments (30 to 60 mm³) were grafted subcutaneously into the interscapular fat pad of 8- to 12-week-old female Swiss nude mice, under avertin anesthesia. Mice were maintained in specific pathogen-free animal housing (Curie Institute) and received estrogen (17 mg/mL) in their drinking water. Xenografts appeared at the graft site two to eight months after grafting. They were subsequently transplanted from mouse to mouse and stored frozen in DMSO-fetal calf serum (FCS) solution or dry-frozen in liquid nitrogen for RNA isolation. The experimental protocol was performed in accordance with French regulations.

Sister Chromatid Exchange (SCE) Assay

This assay was performed as described by Gemble et al. (cf. Reference 19). In brief, cells were plated on glass slides in the presence of 10 µM 5-bromodeoxyuridine (BrdU) (Sigma Aldrich). After two divisions, colchicine (Sigma Aldrich) was added (0.1 µg/ml) and the cells were incubated for 1 h. Cells were then incubated in a hypotonic solution (1:5 (vol/vol) FCS-distilled water) and fixed with a 3:1 (vol/vol) mixture of methanol and acetic acid. They were then stained by incubation with 10 µg/ml Hoechst 33258 (Sigma Aldrich) in distilled water for 20 minutes. The slides were rinsed with 2×SSC (Euromedex) and exposed to ultraviolet light at a wavelength of 365 nm and a distance of 10 cm for 105 minutes. The slides were then rinsed in water, stained with 2% Giemsa (VWR) for 16 minutes, rinsed in water, dried and mounted in EUKITT (Sigma Aldrich). Metaphases were captured and chromosomes were visualized under a Leica DMRB microscope at a magnification of ×100. The number SCEs was evaluated per chromosome.

DNA Methylation Data

The inventors analyzed 482,422 CpGs in the NCI-60 cell lines with Illumina Infinium Human Methylation 450 Beadchips. The DNA methylation datasets are available under accession number GSE66872. The methylation values are presented from 0 to 1. The data were normalized and analyzed as described by Nagales et al. (cf. Reference 22).

The negative correlations between CDA promoter methylation and CDA expression on TCGA samples (see cancergenome.nih.gov) were generated through the Broad Institute FireBrowse portal (see firebrowse.org) (see reference 23) and the cBioPortal for Cancer Genomics database (see Worldwide Web site: cbioportal.org) see References 24 and 25), all the cBioPortal data (expression, mutation, copy number, significance analyses) being loaded directly from FireBrowse. The only promoter CpG site presenting a high significant negative correlation with CDA expression in both NCI-60 cell lines and TCGA samples was selected.

Transcriptomic Data

A collection of 40 human breast tumor cell lines (mostly from ATCC) was established in the Translational Research Department of the Curie Institute. Gene expression profiles were generated with the Affymetrix Exon array and Genosplice algorithms to summarize multiprobe measurements as single mRNA levels.

CDA expression levels were extracted from various transcriptomic datasets: breast tumor cell lines of the Curie Institute collection (see microarrays.curie.fr/publications/recherche_translationnelle/plateforme_genomique/), NCI-60 (CellMiner tools: see discover.nci.nih.gov/cellminer), Cancer Cell Lines Encyclopedia (CCLE; see Worldwide Website: broadinstitute.org/ccle/home), Gene Expression Across Normal and Tumor Tissue database (GENT; see medical-genome.kribb.re.kr/GENT/), the TCGA portal (see cancergenome.nih.gov), and the Gene Expression Omnibus database (GEO; see Worldwide Website: ncbi.nlm.nih.gov/geo). All these data are publicly accessible.

Statistics

All data analysis and processing were performed with GraphPad Prism 6 software.

Pearson's correlation analysis was used to assess the association between two variables. P values for sister SCEs were calculated by Mann-Whitney tests. CDA mRNA levels in normal and cancerous tissues were compared in two-tailed unpaired t-tests. Differences in the induction of CDA expression by 5-Aza-dC, as assessed by RT-qPCR, were evaluated in two-tailed paired t-tests. Survival curves were compared in paired t-tests for HeLa-shCDA versus HeLa-Ctrl cells treated with aminoflavone and HCC-1954 and IGROV-1 cells with and without 5-Aza-dC pretreatment. Unpaired t-tests were used for the other cell lines. Differences were considered statistically significant if P<0.05.

Results

Figure 4:
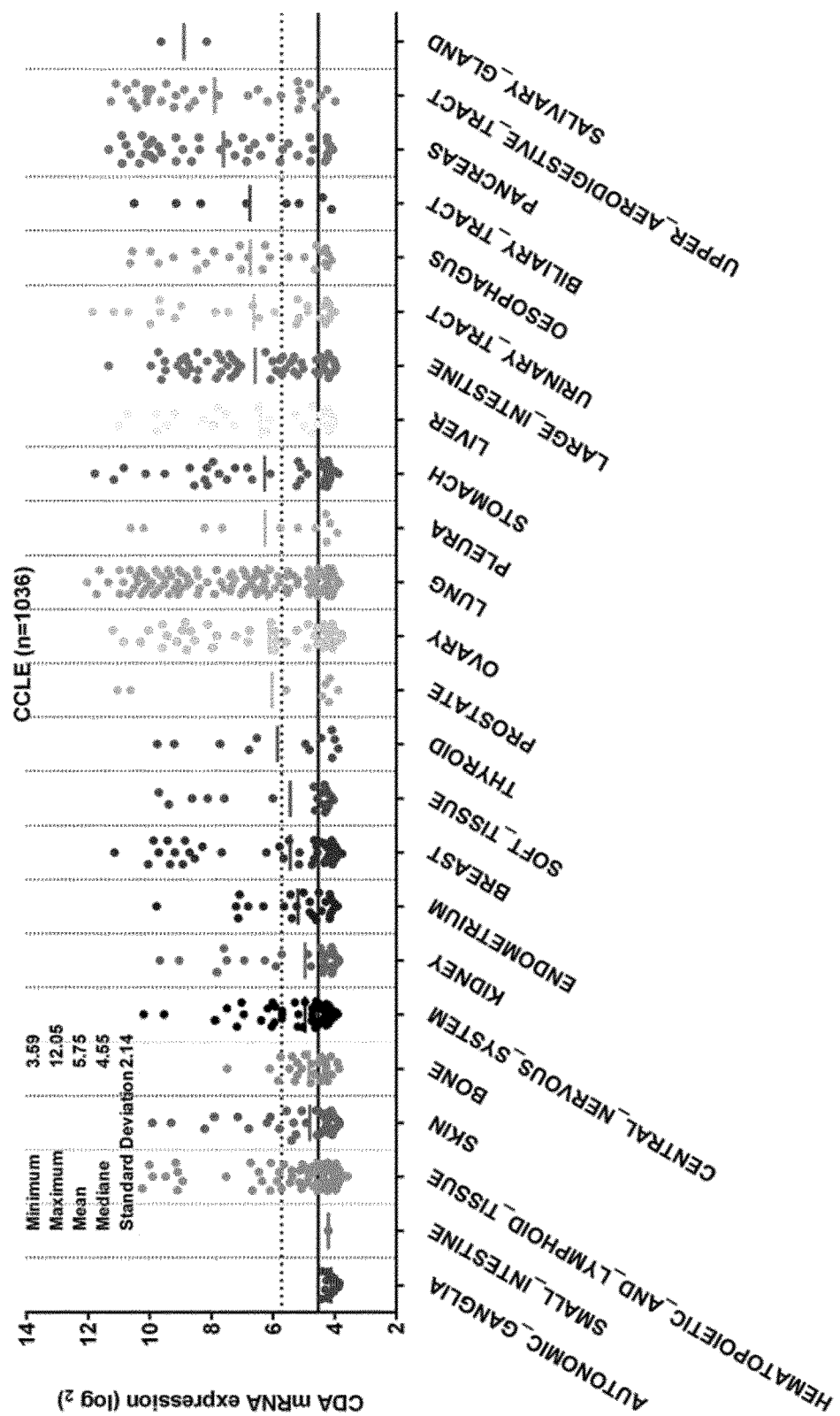
FIG. 4: CDA expression levels in cancer cell lines and tissues. A, Expression data set for CDA mRNA extracted from the Broad-Novartis cancer cell lines encyclopedia (CCLE). The data are presented as log 2 intensity for 1036 cell lines derived from 24 cancers. The horizontal bars represent the mean CDA expression for each cancer type. The mean and median for all cell lines are indicated by continuous and dashed lines, respectively. B-C CDA mRNA levels in various tumor tissues and in normal tissues. The data were extracted from the TCGA database (generated by RNA sequencing) (left panel) and the GENT database (generated with the Affymetrix Human Genome U133Plus2 array) (right panel). D, IHC validation of anti-CDA-primary antibody (ab82347) binding for BS cells not expressing CDA (BS-Ctrl) or constitutively expressing exogenous CDA (BS-CDA). The scale bar represents 50 µm. E, Data set for CDA mRNA levels during cervical cancer progression, extracted from a gene expression analysis available under accession number GSE63514 from the Gene Expression Omnibus (GEO) database. P values were calculated in unpaired t-tests and were considered statistically significant if <0.05.

CDA Expression is Downregulated in a Large Panel of Cancer Cell Lines and Tissues The inventors first analyzed in silico CDA expression in various tumor cell lines studied by microarray analysis. They found that CDA was expressed weakly or not at all in 25 of 34 (73%) breast cancer cell lines from the Curie Institute and 44 of 60 (73%) cancer cell lines derived from nine different organs and tissues from the NCI (FIG. 1A, left and right panels). Similarly, about 60% (700) of the 1036 cancer cell lines from 24 different cancer tissues from the CCLE (Broad-Novartis Cancer Cell Line Encyclopedia) database did not express CDA (FIG. 4A). These results were validated by qPCR and western blotting on a set of 26 representative cancer cell lines from the Curie Institute and the NCI cancer cell line collections (19 breast cancer cell lines, 4 lung cancer cell lines, and 3 ovarian cancer cell lines) (FIG. 1B).

The inventors then investigated whether the absence of detectable CDA expression observed in the majority of cancer cell lines also applied to primary tumor tissues, by performing qPCR to analyze CDA mRNA levels in human primary breast tumors xenografted into nude mice (patient-derived xenografts, PDXs). This approach made it possible to avoid the contamination of primary tumor tissues with normal cells from the stroma (usually up to 30%). It was found that 56 of the 66 (~84%) human primary breast tumors studied had no significant CDA expression (FIG. 1C). CDA protein levels was also analyzed in six types of primary cancer tissues (50 per type) by immunohistochemistry (IHC) with an anti-CDA antibody validated by IHC on isogenic Bloom syndrome-derived cells not expressing CDA (BS-Ctrl) or expressing exogenous CDA (BS-CDA) (19) (see the materials and methods section and the FIG. 4D). CDA expression was stratified into two groups on the basis of staining intensity scores: CDA low (scores of 0 and 1) and CDA high (scores of 2 and 3) (FIG. 1D). About 50% (endometrium) to 88% (breast triple-negative, ovary and colon) of cancer tissues displayed very low levels of CDA expression.

The inventors then compared CDA mRNA levels between healthy and cancerous tissues of different origins, by replotting the CDA mRNA data downloaded from Gene Expression Omnibus (GEO) found in different genomic data sources (Nextbio, Oncomine). Tumor tissues are often contaminated with normal tissues that might express CDA, leading to inappropriate interpretations of CDA expression in some tumor tissues. Nevertheless, CDA expression levels were significantly lower in several tumors than in healthy tissues (FIG. 1E, FIG. 4B, C). These results (summarized in Table 1) reveal that CDA is overexpressed in some tumor tissues, such as those of pancreas, stomach, thyroid and bladder cancers, as previously reported (17, 23), but under-expressed in other tumor tissues, such as those of liver, cervix, colon and esophagus cancers. We confirmed these results by qPCR on a small in-house cohort of colon tissues. We found that CDA expression levels were significantly lower (P=0.0128) in tumor tissues (n=10) than in healthy tissues (n=5) (FIG. 1F).

Finally, analysis of a recently published gene expression dataset used to determine the molecular mechanism of cervical cancer progression (24) revealed that CDA expression decreased considerably with cervical cancer progression (FIG. 4E). This result is consistent with the data presented in FIG. 1E, showing lower levels of CDA expression in cervical cancer tissues than in non-cancerous tissues. Overall, these results suggest that CDA expression tends to be lost during carcinogenesis, at least in some tissues, such as the cervix.

CDA is Downregulated by DNA Methylation

Figure 5:
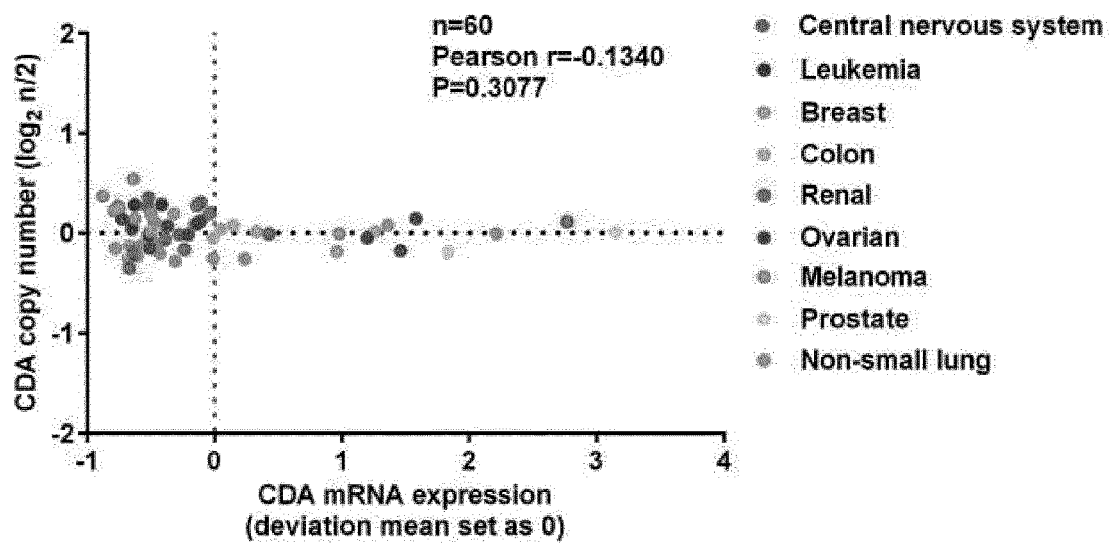
FIG. 5: Experiments related to studies on the silencing of CDA gene expression. A, Scatter plots of the correlation (Pearson's correlation) between DNA copy number and mean centered CDA transcript intensity correlation for the cell lines from the NCI60 (upper panel) and CCLE (lower panel) collections. Dots indicate the tissues from which the cell lines originate. B-C, CDA expression, at the mRNA and protein levels, in non-malignant breast cells (left panel) and in melanoma cells (right panel). TBP and GAPDH were used for RT-qPCR data normalization; hsp90 and GAPDH were used as loading controls for western blotting. D, Cell viability, as assessed in MTT assays on breast cancer cell lines (MDA-MB-231, HCC-1954, MCF-7, BT-20) and an ovarian cell cancer line (IGROV-1) after 96 h of treatment with 5-Aza-dC. Error bars represent the mean±SD of 3 independent experiments for IGROV-1 and 2 experiments for the other cell lines. Survival curves for cell lines with low levels of CDA expression are shown in black and survival curves for cell lines with high levels of CDA expression are shown in gray. In bold, the two cell lines used to test the functionality of the CDA protein in gemcitabine treatment (FIG. 2C). The dashed lines indicate the 5-Aza-dC concentrations used in this study. E, Schematic representation of the CDA gene, highlighting the various CpG sites used for the calculation of Pearson's correlation coefficient. F, Scatter plots showing a non-significant correlation between mRNA seq data for CDA expression and CDA methylation in 10 different cancer samples from The Cancer Genome Atlas (TCGA; (see cancergenome.nih.gov). The CpG probe is indicated for each cancer. The data are publically available and were retrieved from CBioPortal data base for cancer genomics (see cbioportal.org) (29,30) and (see firebrowse.org). Mean CDA expression is indicated by the dashed vertical lines and mean methylation is indicated by the dashed horizontal lines. All P values <0.05 were considered statistically significant.
Figure 5:
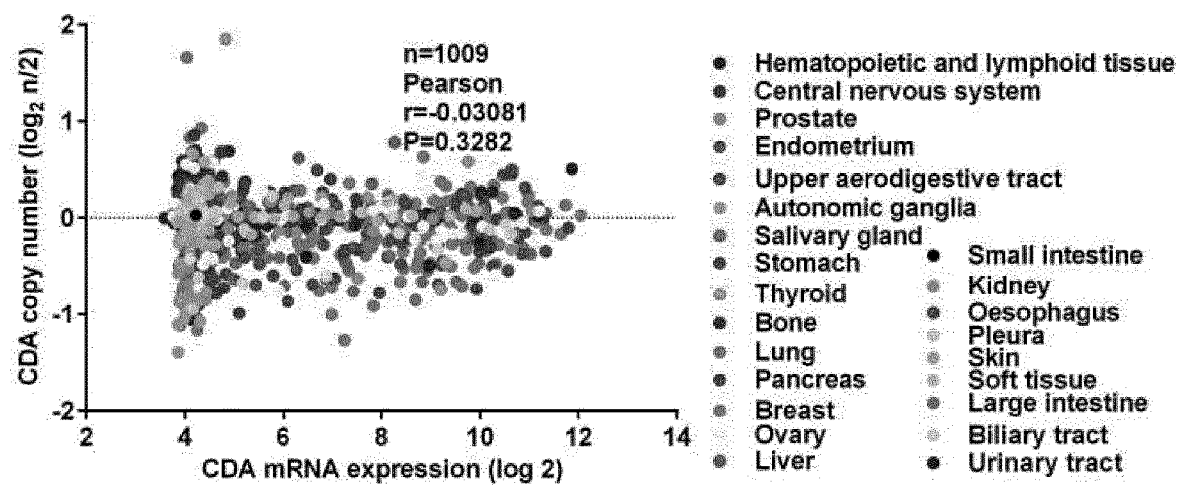

The inventors investigated the mechanism underlying the downregulation of the CDA gene in tumor cells, by first analyzing CDA copy number in the DNA of the CCLE and NCI60 cell lines. No significant correlation was found between CDA mRNA levels and CDA gene copy number (FIG. 5A). The downregulation of CDA levels cannot therefore be attributed to genetic deletions in tumor cells.

Sequencing analysis were then carried out to determine whether CDA (promoter and exons) was mutated in 11 breast cancer cell lines that did not express CDA, through comparison with two breast cancer cell lines expressing high levels of CDA (HCC-1143 and MDA-MB-231, see FIG. 1B) and breast cell lines derived from healthy tissues with strong or weak CDA expression (MCF-12A and 184B5, respectively, FIG. 5B). No genetic mutation likely to lead to CDA inactivation was identified (Table 2A). However, several SNPs were found that had previously been identified and listed in the Single Nucleotide Polymorphism Database (dbSNP) (13, 25-27). These results are consistent with the CDA gene sequencing results for the NCI-60 cell lines (Table 2B) and demonstrate that CDA is not inactivated through genetic alterations in cancer cells.

Figure 2:
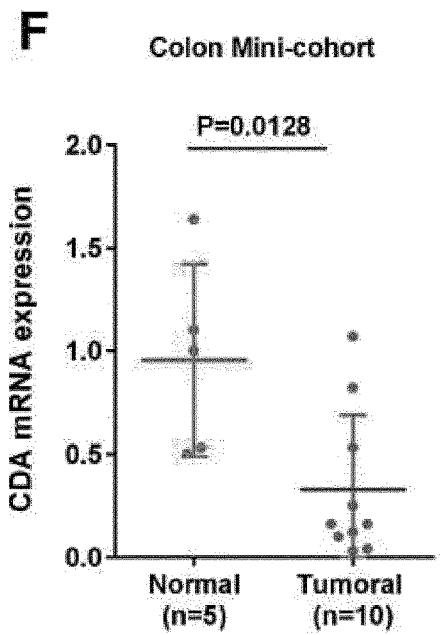
FIG. 2: Silencing of CDA gene expression by DNA methylation. A, Mean-centered CDA transcript intensity data for the NCI60 panel of cell lines obtained with the NCI-Cell Miner analysis tool (upper left panel), and mean CDA gene methylation levels in the data for the NCI60 panel of cell lines extracted from GEO under accession number GSE66872 (lower left panel), and representation of the correlation between CDA transcript intensity and CDA promoter methylation for the cg04087271 and cg00784581 probes (Pearson correlation) (right panel). B, RT-qPCR analysis of the induction of CDA expression relative to GAPDH in cells initially with and without CDA expression, after 96 hours of treatment with 2.5 µM 5-Aza-dC. Error bars represent means±SD for at least 3 independent experiments. The P values were calculated in paired t-test. All P values <0.05 were considered statistically significant. C, Left panels: RT-qPCR analysis (upper panel) and western blot analysis (lower panels) of the induction of CDA expression in HCC-1954 and IGROV-1 cell lines left untreated (white bars) or treated with 1 µM 5-Aza-dC for 96 h (black bars). Survival curves of the HCC-1954 (n=3; middle panel) and IGROV-1 (n=5; right panel) cell lines left untreated (control) or subjected to pretreatment for 96 h with 1 µM 5-Aza-dC (5-Aza-dC), and then treated with various doses of gemcitabine for a further 72 hours. Cell viability was assessed in the MTT assay. Error bars represent means±SD for 3 or 5 experiments. The P values were calculated in paired t-tests. P values <0.05 were considered statistically significant. D, Scatter plots showing the Pearson correlation between mRNA seq data for CDA expression and CDA methylation for 12 different cancer samples from The Cancer Genome Atlas (TCGA; (see cancergenome.nih.gov). The data are publicly available and were retrieved from the CBioPortal database for cancer genomics (see cbioportal.org) (31,32) and (see firebrowse.org). Mean CDA expression is indicated by dashed vertical lines and mean methylation level is indicated by dashed horizontal lines. All P values <0.05 were considered statistically significant.
Figure 2:
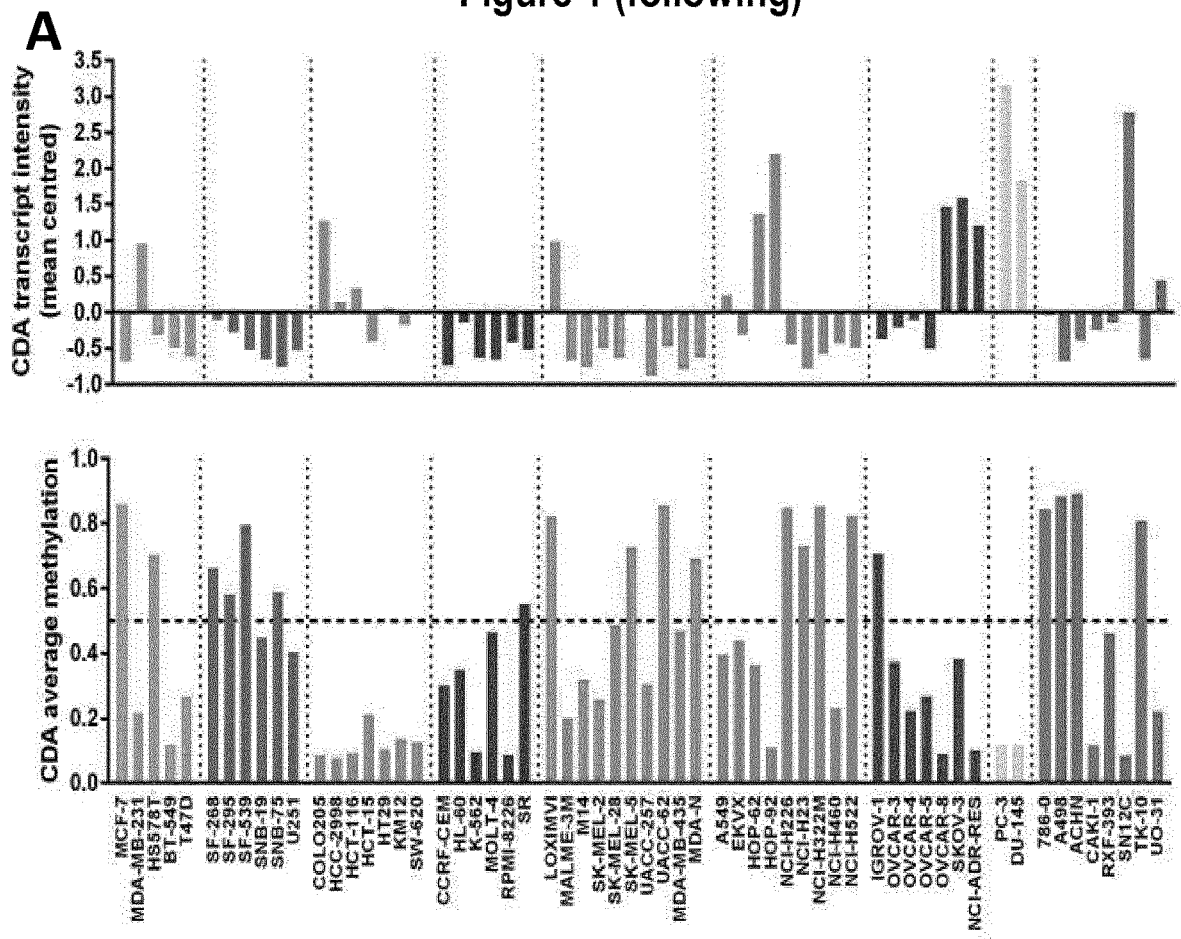

The inventors then explored the possible role of epigenetic regulation of CDA gene expression. The CpG methylation sites were mapped in the CDA gene (FIG. 5E). The levels of methylation of the CDA promoter were then analyzed, using the dataset for the methylation of NCI60 cell lines (22). Pearson's correlation coefficients were calculated for the relationships between methylation at the various CpG methylation sites and CDA expression. A highly significant negative correlation was found between CDA transcript and gene methylation levels (Pearson r=−0.4184, P=0.009) (FIG. 2A). High levels of CDA methylation were found in 42% of the CDA-deficient cell lines (19 of 45), such as MCF-7, and IGROV-1, and no methylation was detected in cell lines overexpressing CDA, such as MDA-MB-231 and HOP-92, except for the LOXIMVI melanoma cell line.

For the validation of these methylation data, a set of cancer cell lines derived from breast, lung, ovarian and melanoma tumors not expressing CDA (FIG. 1B and FIG. 5C) was treated with the DNA methyltransferase activity inhibitor 5-Aza-2'-deoxycytidine (5-Aza-dC), resulting in DNA demethylation (28). 5-Aza-dC was found to induce a strong increase (up to 1000-fold induction) in CDA mRNA levels (FIG. 2b) without major toxicity (FIG. 5D) in the 7 CDA-deficient cell lines analyzed. By contrast, it had little or no effect on CDA transcript levels in the MDA-MB-231, HOP-92, HCC-1143 and HCC-1937 control cell lines, which have constitutively high levels of CDA (~two-fold induction).

The selection of CDA overexpression in response to prolonged drug exposure is responsible for resistance to gemcitabine (16, 29). Furthermore, the ectopic expression of CDA in CDA-deficient cancer cells leads to a significant increase in resistance to gemcitabine (16, 30). The inventors thus evaluated the functionality of the CDA protein produced after 5-Aza-dC treatment, by breast and ovarian cancer cells, HCC-1954 and IGROV-1, respectively. The cells were left untreated or were subjected to pretreatment with 5-Aza-dC for 96 hours and then to treatment with various concentrations of gemcitabine over a period of 72 hours. The induction of CDA protein production by 5-Aza-dC led to a significant increase in gemcitabine resistance (FIG. 2C). Thus, the treatment of CDA-deficient cells with 5-Aza-dC strongly induced the production of a functional CDA protein.

The inventors then analyzed in silico CDA promoter methylation levels (FIG. 5E) on TCGA samples for 22 different tissue cancers, using the CBioPortal for cancer genomics (see Worldwide Website: cbioportal.org/) (31,32). A highly significant negative correlation was found between CDA transcript levels and CDA promoter methylation (FIG. 2D). Methylation of the cg04087271 methylation site was correlated with CDA deficiency in both tumor tissues and NCI60 cell lines, whereas methylation of the cg24502330 site was not, probably because this site was found to be methylated in only two tumor tissues, bladder and prostate, which were either absent (bladder) or did not present CDA deficiency (prostate) in the NCI60 panel of cell lines. However, in both cancer cell lines and tumor tissues, CDA promoter methylation levels were significantly higher in samples with low CDA transcript levels (FIG. 2D) than in those with high CDA transcript levels. This correlation was not significant in some other cancer types, but a subpopulation of these cancers with low CDA expression and high CDA promoter methylation levels was nevertheless identified (FIG. 5F). Thus, the loss of CDA expression in cancer cells is broadly driven by DNA methylation and DNA demethylation restores the expression of a functional CDA protein.

Figure 3:
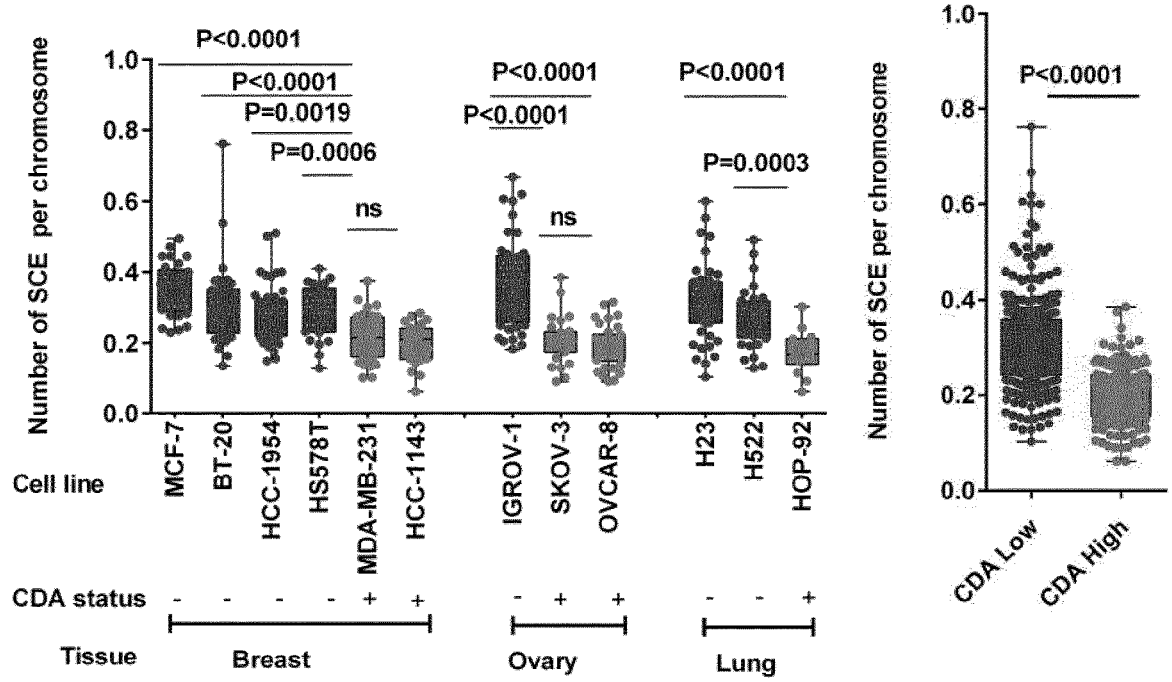
FIG. 3: Drug sensitivity of CDA-deficient cells. A, SCE frequency in CDA-deficient and CDA-proficient cells (left panel) and representation of SCE frequency in cells classified on the basis of their CDA expression status, low or high (right panel). P values were calculated in Mann-Whitney tests for at least 3 independent experiments. P<0.05 was considered statistically significant B, Scatterplot showing a significant negative correlation between aminoflavone cytotoxicity and CDA expression (Pearson correlation) in the NCI60 panel of cell lines. The dots indicate the origin of the cancer tissue. C, Isogenic HeLa cell lines (HeLa control cells in gray and CDA-depleted HeLa cells in black) were treated for 72 hours with the indicated concentrations of aminoflavone, and the percentage of cells surviving is shown. D, Breast (MCF-7, MDA-MB-468 and MDA-MB-231) and ovarian (SKOV-3, OVCAR-8 and IGROV-1) cancer cell lines were treated for 72 hours with the indicated concentrations of aminoflavone. Survival curves of cell lines with low levels of CDA expression are represented in black and the survival curves of cell lines with high levels of CDA expression are shown in gray. For C and D, cell viability was assessed in MTT assays. The error bars represent means±SD for three independent experiments. P values <0.05 were considered statistically significant.
Figure 3:
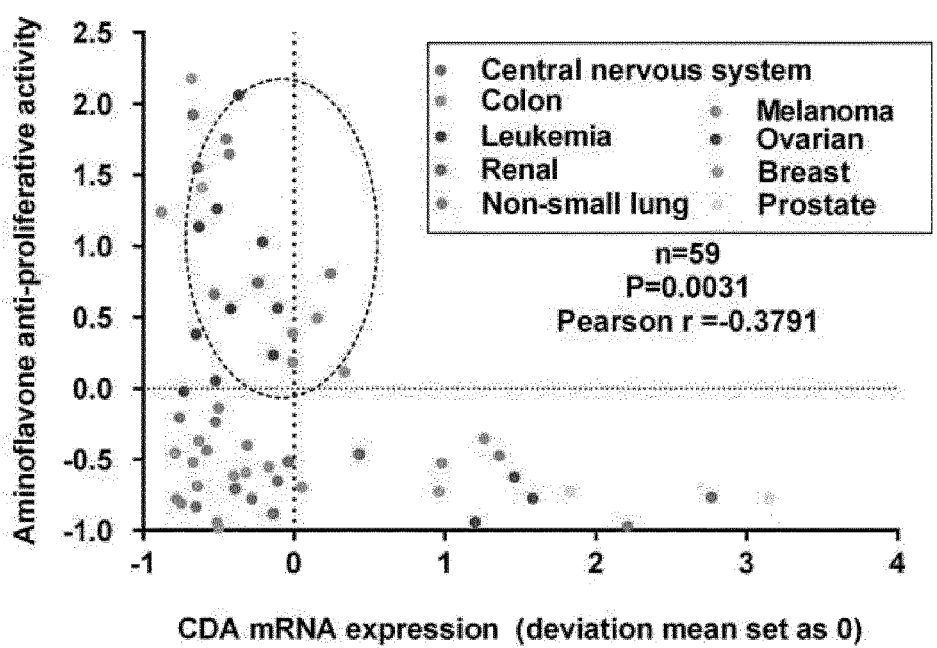

Loss of CDA Expression in Tumor Cells Defines a New Tumor Subgroup that Could be Specifically Targeted by Chemotherapy The inventors previously reported that CDA deficiency in BS cells or CDA depletion in HeLa cells leads to an increase in sister chromatid exchange (SCE) frequency (19). Whether constitutive CDA deficiency in tumor cells was also associated with an increase in SCE frequency was investigated by analyzing basal SCE levels in several cancer cell lines derived from breast, lung and ovary tumors. SCE frequency was significantly higher in the cancer cell lines not expressing CDA than in those expressing CDA (FIG. 3A).

Thus, tumors from the same classically defined groups may display differences in CDA expression status resulting in contrasting cellular properties, such as SCE levels (e.g. CDA-proficient HCC-1143 cells and CDA-deficient BT-20 cells are both classified as triple-negative breast cancer cells). The inventors thus propose the use of CDA expression status in tumor cells to define two new subgroups: CDA-deficient tumors and CDA-proficient tumors. These new subgroups may differ in their sensitivity to antitumor therapies. The targeting of CDA-deficient tumor cells might therefore open up new possibilities for cancer therapy.

The CellMiner web tool (33) can be used to assess the correlation between gene expression and drug sensitivity/resistance. The inventors searched for drugs with antiproliferative activity significantly correlated with CDA expression levels. 277 such drugs were identified, 94 of which were more toxic to CDA-deficient cells and 183 of which were more active against CDA-proficient cells (Tables 3 and 4). Our hypothesis that some drugs that do not affect CDA-proficient cells can specifically target CDA-deficient cells was tested by focusing on an aminoflavone (AF) derivative (AFP464; NSC 710464) for which a highly significant negative correlation (Pearson r=−0.379, P=0.0031) with CDA deficiency had been found and which has been selected for testing in clinical trials (Tables 3 and 4) (34-37). Twenty CDA-deficient cell lines of the 43 tested (46.5%), including MCF-7 and IGROV-1, were sensitive to AF, whereas 13 of the 16 (81.25%) CDA-proficient cell lines were resistant to this drug (FIG. 3B).

Figure 6:
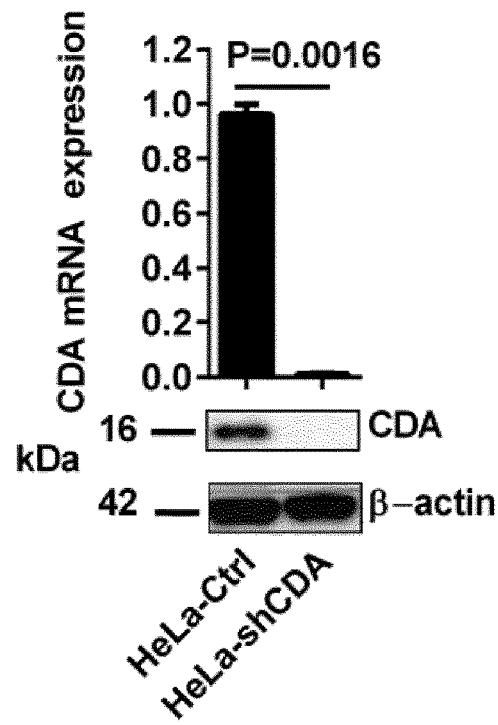
FIG. 6: Depletion of CDA expression by short hairpin RNA in HeLa cells. CDA mRNA levels relative to GAPDH (upper panel) and protein levels (lower panels) were analyzed in HeLa-Ctrl cells and in HeLa-shCDA cells, by RT-qPCR and western blotting, respectively (n=3). β-actin was used as a loading control for western blotting. The cell lines have been described elsewhere (19).

The causality of the relationship between CDA down-regulation and AF anti-proliferative activity was evaluated by shRNA-mediated CDA depletion in HeLa cells (FIG. 6). CDA depletion was found to increase sensitivity to AF treatment significantly (FIG. 3C). The inventors then assessed the cytotoxicity of AF in six breast and ovary cancer cell lines, three of which were CDA-deficient (MCF-7, MDA-MB-468 and IGROV-1), the other three being CDA-proficient (MDA-MB-231, OVCAR-8 and SKOV-3). The CDA-deficient cell lines were highly sensitive to AF treatment, whereas the CDA-proficient cell lines were resistant (FIG. 3D, left and right panels).

These results, demonstrating that CDA expression status can be used as a predictor of sensitivity to AF, are supported by published data validating the antitumor activity of AF in studies of mouse xenograft models in vivo with the MDA-MB-468 and MCF-7 tumor cell lines, which are deficient for CDA (38-40). Conversely, AF has been shown to be inactive in the CDA-proficient MDA-MB-231 xenograft model (40). CDA deficiency is thus a potential new sensitive biomarker or target for anticancer therapies.

Discussion

These results demonstrate that CDA expression is lost in a large proportion of cancer cells and tumor tissues, and CDA-deficient tumors were identified as a new subgroup of cancers. The loss of CDA expression is mostly due to DNA methylation and the treatment of CDA-deficient cells with 5-Aza-dC was sufficient to restore the expression of a functional CDA. This is the first study, to our knowledge, to reveal the extent of CDA inactivation and its epigenetic control in cancer.

DNA methylation may be the predominant mechanism of CDA silencing, but it is clearly not the only one, as some CDA-deficient cell lines present no CDA gene methylation.

CDA has already been shown to play a crucial role in the response of cancer cells to widely used nucleoside analogs, such as cytosine arabinoside and gemcitabine, and the dose-limiting toxicity of these drugs (6, 41-44). Our results suggest that IHC assessments of CDA levels could be used to determine the CDA status of tumors, with potential implications for treatment.

Oxidized and epigenetically modified cytidine nucleosides specifically target tumors overexpressing CDA (17, 18). It was found that 5-Aza-dC treatment strongly induced the expression of a functional CDA in CDA-deficient tumor cells, with little or no effect on CDA expression in CDA-proficient cells. These findings suggest that DNA-demethylating agents could be assessed as a possible treatment for CDA-deficient tumors, to induce CDA overexpression and then sensitize these tumors to treatment with oxidized and epigenetically modified cytidine nucleosides.

Finally, these results suggest that the targeting of CDA deficiency might offer new possibilities for treatment. In silico screening with the NCI CellMiner analysis tool identified aminoflavone as a proof-of-principle candidate for the targeting of CDA-deficient tumor cells. AF was found to be specifically effective in CDA-deficient tumor cells, while having no effect on CDA-proficient cells. Thus, the subgroup of tumors not expressing CDA could be specifically targeted by such treatment, and CDA expression status could be used as a new marker to guide anticancer therapy. Molecules not yet shown to be active against this tumor subgroup could be discovered through the systematic screening of CDA-proficient and -deficient cells.

In conclusion, these results constitute a proof-of-concept that CDA deficiency is a new predictive marker of susceptibility to antitumor drugs that could be used as a new target for anticancer therapies, thus opening up new possibilities for the treatment of cancers.

Example 2

Materials and Methods
Cell Culture and Treatments 5 cancer cell lines were used in this study (cf. table 5): 3 breast cancer cell lines from the Translational Research Department of the Curie Institute (MCF-7, MDA-MB-468 and MDA-MB-231) and two cervical cancer cell lines (HeLa-Ctrl and HeLa-shCDA).

All cells were routinely checked for the absence of mycoplasma and were maintained in the recommended media (cf. table 5).

Cell viability was carried out with 3-(4,5-dimethyl-2-thiazolyl)-2,5 diphenyl-2H-tetrazolium bromide (MTT-Life Technologies) in 96-well microplates. The cell viability was assessed after dasatinib (Sigma Aldrich) treatment during 72 h by plating MCF-7, MDA-MB-468 and MDA-MB-231 cells at densities of 3000 cells/well, and HeLa-Ctrl and HeLa-shCDA at 1500 cells.

Results

The CellMiner web tool (33) can be used to assess the correlation between gene expression and drug sensitivity/resistance. The inventors searched for drugs with antiproliferative activity significantly correlated with CDA expression levels. They identified 277 such drugs, 94 of which were more toxic to CDA-deficient cells (cf. table 4) and 183 of which were more active against CDA-proficient cells (cf. table 3). Among them, dasatinib, widely used in anti-cancer therapy, presented a highly significant positive correlation with CDA proficiency.

Figure 7:
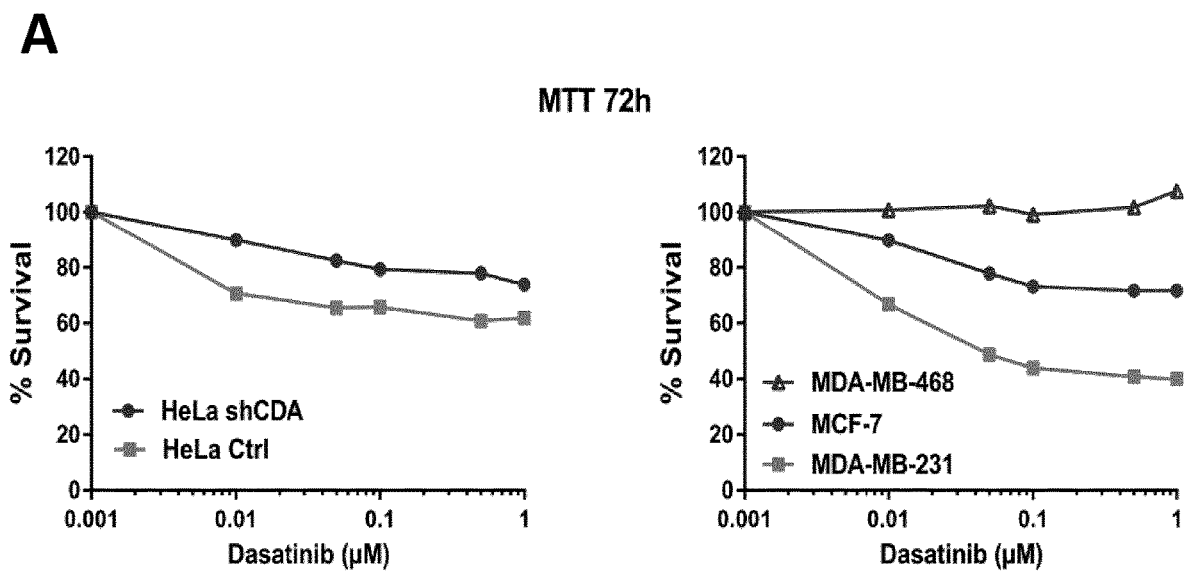
FIG. 7: Dasatinib sensitivity of CDA-Proficient cells. A, Isogenic HeLa cell lines (HeLa control cells and CDA-depleted HeLa cells) (left panel) or breast cancer cell lines MCF-7, MDA-MB-468 and MDA-MB-231 (right panel) were treated for 72 hours with the indicated concentrations of Dasatinib. The percentage of cells surviving is shown. Survival curves of cell lines with low levels of CDA expression are represented and the survival curves of cell lines with high levels of CDA expression are shown. Cell viability was assessed using MTT assays. B, Images of HeLa control cells and CDA-depleted HeLa cells 24 h after treatment with 0.5 or 1 µM of Dasatinib or DMSO treatment, showing a strong effect (round cells, blocked in mitosis) on HeLa control cells (expressing CDA), and no effect on CDA-depleted HeLa cells.

The causality of the relationship between CDA proficiency and dasatinib anti-proliferative activity was evaluated by shRNA-mediated CDA depletion in HeLa cells (cf. upper left panel of FIG. 7). It was found that CDA-expressing HeLa cells were more sensitive to dasatinib treatment than CDA-depleted HeLa cells (cf. upper left and lower panels of FIG. 7). The cytotoxicity of dasatinib was then assessed in three breast cancer cell lines, two of which were CDA-deficient (MCF-7, MDA-MB-468), the other one being CDA-proficient (MDA-MB-231). The CDA-deficient cell lines were resistant to dasatinib treatment, whereas the CDA-proficient cell line was sensitive (cf. upper right panel of FIG. 7).

Discussion

These results suggest that the targeting of CDA proficiency might offer new possibilities for treatment. Dasatinib was found to be specifically effective in CDA-proficient tumor cells, and that this drug has no effect on CDA-deficient cells. As reported in example 1,5-Aza-dC treatment strongly induced the expression of a functional CDA in CDA-deficient tumor cells, with little or no effect on CDA expression in CDA-proficient cells. These findings suggest that DNA-demethylating agents could be assessed as a possible treatment for CDA-deficient tumors, to induce CDA overexpression and then sensitize these tumors to treatment with dasatinib.

Example 3

Figure 8:
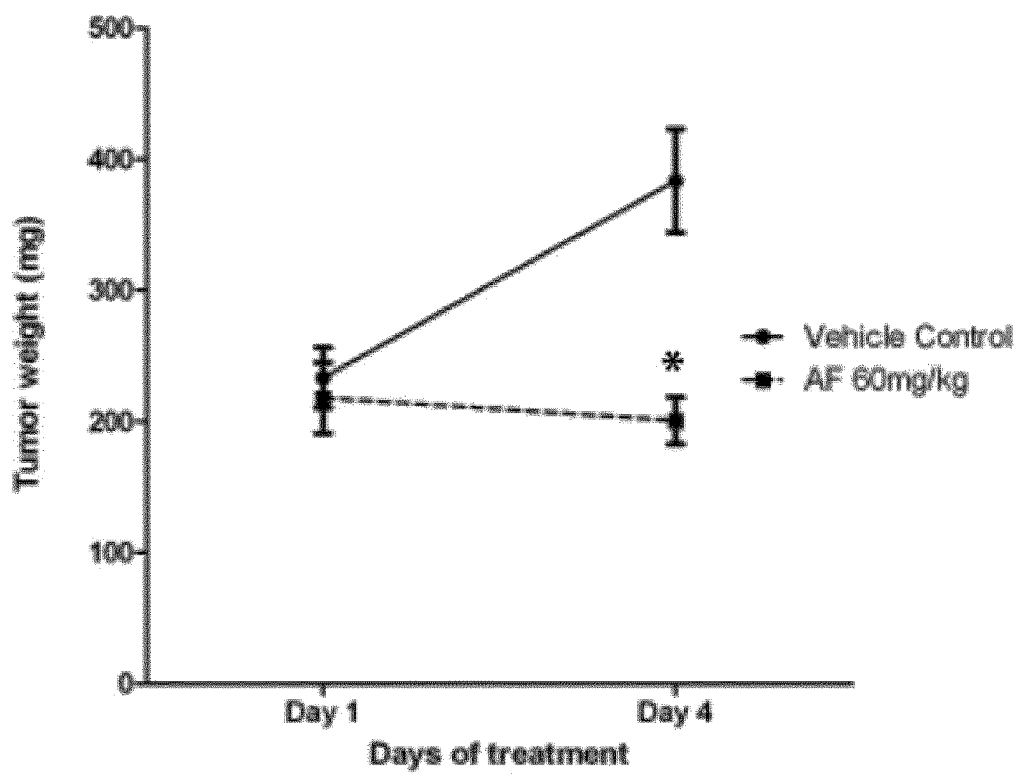
FIG. 8 (corresponding to FIG. 6A of Terzuol et al., Cancer Res., 2010, 70:6837-48): In vivo antitumor activity of aminoflavone against MCF7 xenograft. MCF-7 were implanted into nude mice (n=5/group) and allowed to grow up to ~200 mg, when treatment with AF (60 mg/kg daily×4 days i.p.) was started. Tumor weight was measured as described in Materials and Methods, (Mann-Whitney test; *, p<0.01).
Figure 9:
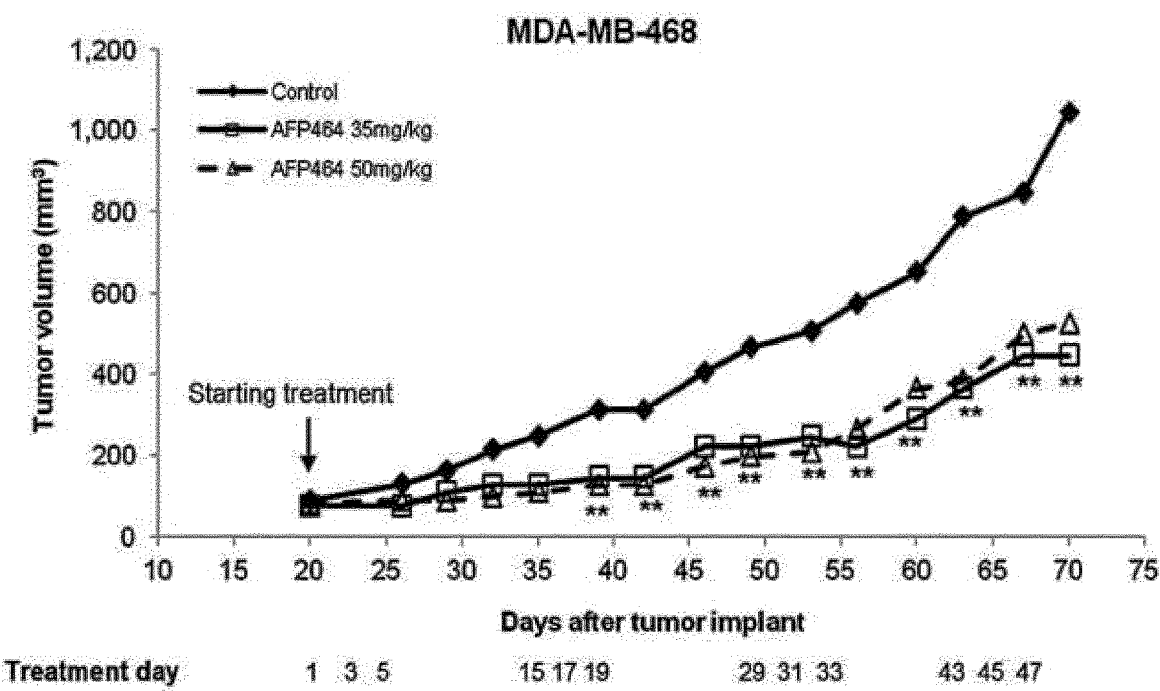
FIG. 9 (corresponding to FIG. 4A-B of Stark et al., PloS One, 2013, 8:e74525): In vivo antitumor activity of aminoflavone against MDA-MB-468 and MDA-MB-231 xenograft. A, Tumor growth in the control and drug treatment groups. Data are expressed as the median tumor volume of 10-14 tumors. *Kruskal-Wallis test, the median tumor volume in the combined treatment group was significantly different from those in the control and AFP464-only treatment groups in the MDA-MB-231 xenograft model, P<0.05. **Kruskal-Wallis test, the median tumor volume for each AFP464 treatment group was significantly different from that of the control group in the MDA-MB-468 xenograft model, P<0.01. B, Western blot of ERα protein expression in the tumor tissues that were collected from the control and vorinostat/AFP464-treated mice. MDA-MB-231 and MDA-MB-231/wtERα cell lines were used as the ERα-negative and -positive controls, respectively. Lanes 1 and 2 were whole cell lysates from MDA-MB-231 and MDA-MB-231/wtERα cell lines, respectively; lanes 3-5 are MDA-MB-231 xenograft tumor tissue lysates obtained from mice treated with the vehicle solution (control), vorinostat 50 mg/kg, or a combination of vorinostat (50 mg/kg) and AFP464 (35 mg/kg), respectively.

The results presented in this example constitute a new analysis of in-vivo experiments already presented in Terzuol et al. (Cancer Res., 2010, 70: 6837-48) and Stark et al. (PloS One, 2013, 8:e74525). In particular, the FIG. 8 is FIG. 6A of Terzuol et al. and FIG. 9 is FIG. 4A-B of Stark et al.

Materials and Methods

MCF7 Xenograft (Directly From Terzuol et al.)

Studies were conducted in an AAALAC-accredited facility with an approved animal protocol. MCF-7 ($1\times10^7$) were injected subcutaneously (s.c.) into the flank of female athymic nude (NCr/nu) mice (Animal Production Area, NCI-Frederick). Beta-estradiol cypionate (3 mg/kg) was administered intramuscularly every 7 days. Tumor size was determined by collecting length and width measurements and calculating the tumor weight (mg) as [tumor length× (tumor width)2]/2, where the tumor length is the longest dimension (mm) and the tumor width is the narrowest dimension (mm). AF (saline/0.05% Tween 80) was dosed i.p. Five mice per group were treated daily for 4 days with AF (60 mg/kg) or vehicle control. When mice were sacrificed (day 4), tumors from each animal were harvested and used to analyze mRNA and protein expression, as described previously.

MDA-MB-468 and MDA-MB-231 Xenograft (Directly From Stark et al.)

To determine the combined antitumor effect of vorinostat and AFP464 in vivo, the antitumor activity of vorinostat and AFP464, each given alone or in combination, was evaluated using a mouse xenograft model of basal B subtype (or mesenchymal-like TNBC) MDA-MB-231 cells. In addition, the antitumor activity of AFP464 alone was assessed using a mouse xenograft model of basal A subtype (or basal-like TNBC) MDA-MB-468 cells, which has shown in vitro sensitivity to AFP464 and served as a positive experimental control. The animal study was carried out in strict accordance with the recommendations in the National Institutes of Health Guide for the Care and Use of Laboratory Animals. The protocol was approved by the Wayne State University Institutional Animal Care and Use Committee (protocol #A03-10-08).

Female athymic BALB/c mice (5-6 weeks of age) were obtained from NCI Frederick Animal Production Program (Charles River Laboratories, Frederick, Md.) and housed under specific-pathogen-free conditions with water and food provided ad libitum. The mice were acclimated for 1 week prior to tumor cell implantation. MDA-MB-231 or MDA-MB-468 tumor fragments (30-50 mg) were implanted subcutaneously by trocar in the right and left flank area of each mouse. When established tumors were palpable (i.e., ~10 or 20 days after implantation of MDA-MB-231 or MDA-MB-468 cells, respectively), the mice were randomly assigned to experimental and control groups, and the treatments were initiated.

For the MDA-MB-231 xenograft model, the mice were randomized into 6 groups (7 mice per group). In the combined treatment group, the mice were pretreated with vorinostat (suspended in methylcellulose/0.1% Tween 80 solution, 50 mg/kg) by oral gavage (p.o.) daily for 3 days (i.e., on treatment days −3 to −1 and days 12 to 14) before being treated with AFP464 (dissolved in 5% glucose olution, 35 mg/kg) via tail vein injection (i.v.) on treatment days 1, 3, and 5 of a 14-day cycle for a total of 2 cycles. Accordingly, in the AFP464-only treatment group, the mice were given the vehicle (methylcellulose/0.1% Tween 80 solution) orally for 3 days before being treated with AFP464 at a dose of 35 or 70 mg/kg i.v. on treatment days 1, 3, and 5 of a 14-day cycle for a total of 2 cycles. In the vorinostat-only treatment group, the mice were treated with vorinostat (50 mg/kg) p.o. on days −3 to −1 and days 12 to 14 and given the vehicle (5% glucose olution) at the same time as AFP464 administration in the combined treatment group. In the vehicle control group, the mice were given the vehicle (methylcellulose/0.1% Tween 80 solution or 5% glucose solution) on a schedule matching that of the combined treatment group.

For the MDA-MB-468 xenograft model, the mice were randomly assigned to 3 groups (7 mice per group). For the treatment groups, the mice were treated with AFP464 alone i.v. at a dose of 35 or 50 mg/kg, on days 1, 3, and 5 of a 14-day cycle for a total of 4 cycles. In the control group, the mice were treated with 5% glucose solution i.v. on a schedule matching that of the treatment groups.

Tumor size was measured two or three times per week with a digital caliper. The tumor volume was calculated as 0.5×length×width2. Tumor growth inhibition at an indicated time point was expressed as (1−VT/VC)×100%, where VT and VC are the median tumor volume in the treatment and control groups, respectively. Overall drug tolerance for each treatment was evaluated by body weight changes and general health of the mice throughout the experiments. Body weight was measured daily for the duration of the study. The maximum tolerated dose (MTD) was defined as the dose inducing a maximum loss of body weight of less than 15% and/or no more than 10% treatment-related deaths [23]. When the control group reached humane tumor burden limits (median tumor volume >1000 mm3), all mice were euthanized by cervical dislocation, and tumors were surgically removed. Half of the tumor was snap-frozen and used for subsequent western blot analysis of ERα, and the other half was fixed in 10% formalin and embedded in paraffin. Sections (4 μm thick) of tumors were cut and fixed on slides and used for subsequent immunohistochemical staining for ERα and AhR.

Results

Terzuol et al. implanted MCF-7 cells subcutaneously in female athymic nude mice. When tumors reached approximately 200 mg, mice (n=5/group) were randomized to receive either vehicle control or AF (60 mg/kg, ip) daily for four days. As shown in FIG. 8, aminoflavone (AF) exerts a cytostatic effect on tumor growth (p<0.01), relative to vehicle-treated mice.

Starck et al. shown that aminoflavone (AFP464) exerts in vivo antitumor activity in an MDA-MB-468 xenograft model, as evidenced by statistically significantly delayed tumor growth in mice treated with 35 or 50 mg/kg AFP464 compared to mice treated with vehicle control (FIG. 9A). Both dose levels were well tolerated and produced equivalent antitumor activity. After one and two cycles of AFP464 treatment, the median tumor growth was inhibited by 57% and 54%, respectively, compared to the control, P<0.01.

In contrast, AFP464 alone did not show antitumor activity (0% inhibition) at a dose of either 35 or 70 mg/kg in the xenograft model using mesenchymal-like TNBC MDA-MB-231 cells (FIG. 9B). AFP464 was well tolerated at a dose of 35 mg/kg, but 70 mg/kg induced up to 15% body weight loss and the death of 1 of 7 mice during the course of treatment.

As demonstrated by the inventors, MCF-7 and MDA-MB-468 cells do not express detectable CDA, whereas MDA-MB-231 cells express high levels of CDA (cf. FIGS. 1A and 1B).

These in vivo data are thus consistent with the in vitro data that demonstrated that aminoflavone specifically targets CDA-deficient cancer cells.

Example 4

Figure 10:
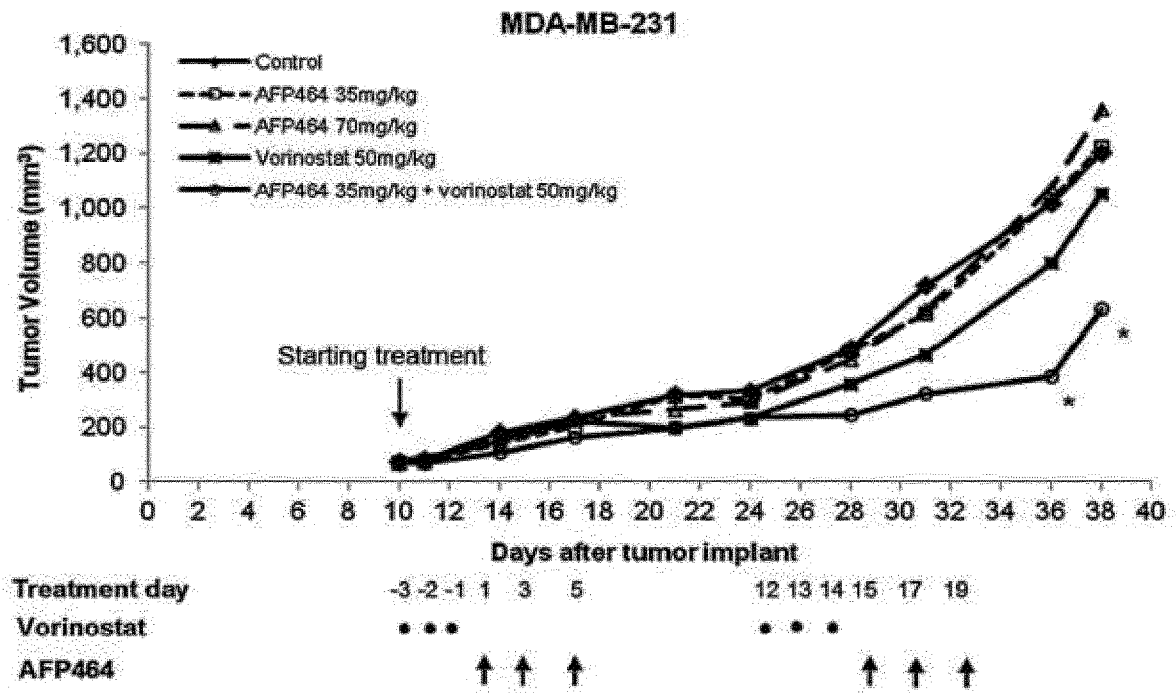
FIG. 10 (corresponding to FIG. 8B of Schwarz et al., J Clin Invest, 2014, 124(12): 5490-5502): In vivo antitumor activity of dasatinib against MCF7 xenograft. MCF-7 cells were injected s.c. into athymic ovariectomized mice supplemented with short-term 14-day release 17β-estradiol pellets. Mice bearing tumors ≥150 mm$^3$ were randomized to vehicle, dasatinib (15 mg/kg/d, p.o.), BKM120 (30 mg/kg/d, p.o.) and fulvestrant (5 mg/wk, s.c.), or BKM120, fulvestrant, and dasatinib for 7 weeks. Data are presented as log$_2$ of mean tumor volume (*P<0.0001 vs. vehicle, #P<0.01 vs. BKM and Fulv or dasatinib).
Figure 10:
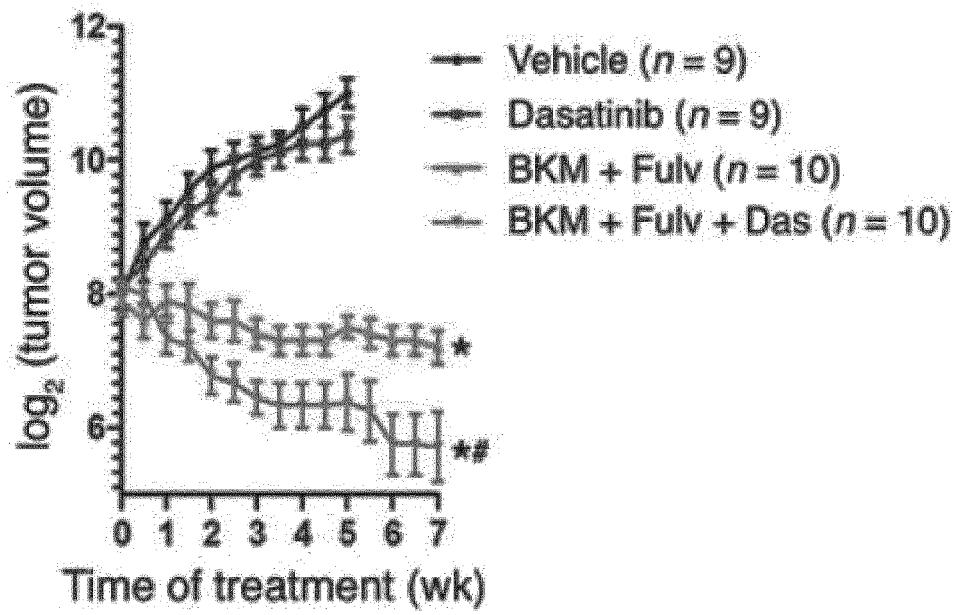
Figure 11:
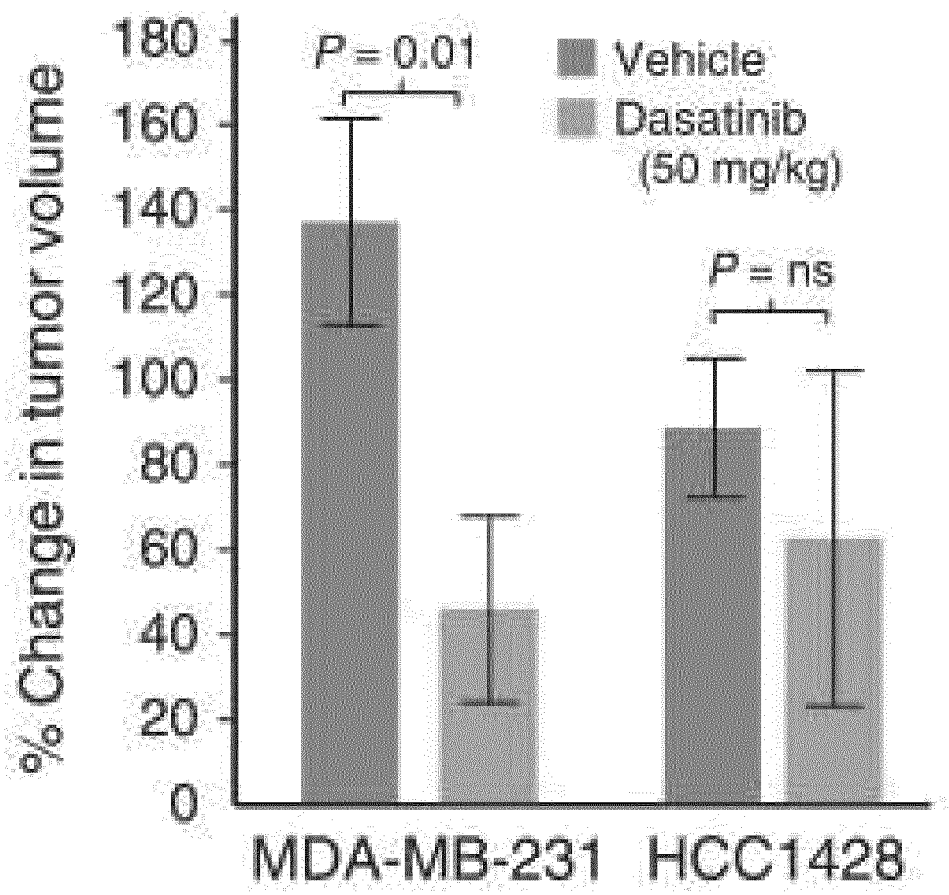
FIG. 11 (corresponding to FIG. 5F of Martins et al., Cancer Discovery, 2015, 5(2): 154-67): In vivo antitumor activity of dasatinib against MDA-MB-231 and HCC1428 xenograft. Percent change in tumor volume of human cell lines xenografted into mice and treated daily with the indicated concentration of dasatinib via oral gavage. A minimum of 5 mice were used in each group. n.s.=not significant.

The results presented in this example constitute a new analysis of in-vivo experiments already presented in Schwarz et al. (J Clin Invest., 2014, 124(12): 5490-5502) and Martins et al. (Cancer discovery, 2015, 5(2); 154-67). In particular, the FIG. 10 is FIG. 8B of Schwarz et al. and FIG. 11 is FIG. 5F of Martins et al.

Materials and Methods

MCF7 Xenograft (Directly From Schwarz et al.)

Female ovariectomized athymic mice were implanted s.c. with a 14-day-release 17β-estradiol pellet (0.17 mg) and $10^7$ MCF-7 parental cells or stably transfected with $LYN^{WT}$ or $LYN^{E159K}$. After 4 weeks, mice bearing tumors ≥150 mm$^3$ were randomly assigned to treatment with vehicle (80 mM sodium citrate buffer, pH 3), dasatinib (15 mg/kg/d, per os [p.o.]), BKM120 (30 mg/kg/d, p.o.) and fulvestrant (5 mg/wk, s.c.), or BKM120, fulvestrant, and dasatinib. Tumor diameters were measured using calipers twice per week, and volume in mm$^3$ was calculated with the formula: volume=width$^2$×length/2. Tumors were harvested and snap frozen in liquid $N_2$ or fixed in 10% formalin prior to paraffin embedding for IHC.

MDA-MB-231 and HCC1428 Xenograft (Directly From Martins et al.)

Animal work was conducted in accordance with protocols approved by the Institutional Care and Use Committee for animal research at the University of California, San Francisco. Nude mice (BALB/c nude/nude) were subcutaneously injected with 1.5×106 MDAMB231 cells or 6×106 HCC1428 cells mixed 1:1 with Basement Membrane Matrix (BD Biosciences). Initial tumor dimensions were monitored three times weekly and the treatment was initiated when tumor volume reached about 80 mm3. Once animals reached indicated tumor volume, they were randomly placed into control or treatment groups. Animals were treated with 50 mg/kg crushed Dasatinb (Sprycel) tablets from the UCSF pharmacy dissolved in water daily for 14 days via oral gavage. Tumor volume was calculated daily from two diameter measurements using calipers, one along the anterior-posterior axis and the other along the lateral-medial axis. Percent change for tumor growth is based on volumes calculated from size on day 1 of treatment compared to day 15.

Results

Schwarz et al. established MCF-7 xenografts in ovariectomized athymic mice. Treatment with BKM120 and fulvestrant or BKM120, fulvestrant, and dasatinib inhibited growth of established tumors compared with vehicle. On the opposite, treatment with dasatinib alone did not inhibit the growth of established tumors compared with vehicle (P<0.0001; FIG. 10).

Martins et al. generated xenografts of MDAMB231 and HCC1428 in nude mice and treated them daily with dasatinib or vehicle administered orally for 15 days. Tumor volume was significantly reduced in MDAMB231 xenografts (p=0.01) but not in the HCC1428 derived tumors (cf. FIG. 11).

As shown above by the inventors, MCF-7 and HCC1428 cells do not express detectable CDA, whereas MDA-MB-231 cells express high levels of CDA (cf. FIGS. 1A and 1B).

These in vivo data are thus consistent with the in vitro data that demonstrated that dasatinib specifically targets CDA-proficient cancer cells.

Example 5

Materials and Methods:

ON-TARGET plus non-targeting control (siCTRL, #D-001810-10-05) and ESR1-targeting (#L-003401-00-0005) siRNAs pools were purchased from Dharamcon.

The estrogen positive cell line MCF-7 was reverse transfected with siCtrl or siESR1 using Lipofectamin® RNAiMax reagent (Invitrogen) according to the manufacturer conditions. After 96 h, transfected cells were treated with increasing doses of Dasatinib for additional 72 h, as indicated in the corresponding figure.

The cells were plated at 1200 cells/well density in a 96 multiwall plate. The cells were released in fresh medium 24 h following transfection.

The primer sequences used for ESR1 amplification are reported in (Calgaro A M et al., 2010 J Natl Cancer Inst; 102:1637-1652) ESR1 Forward: 5'-CCGGCTCCGCAAATGCTAC-3' (SEQ ID NO: 15) and Reverse 5'-AAGGTTGGCAGCTCTCATGTC-3' (SEQ ID NO: 16).

Results

Figure 12:
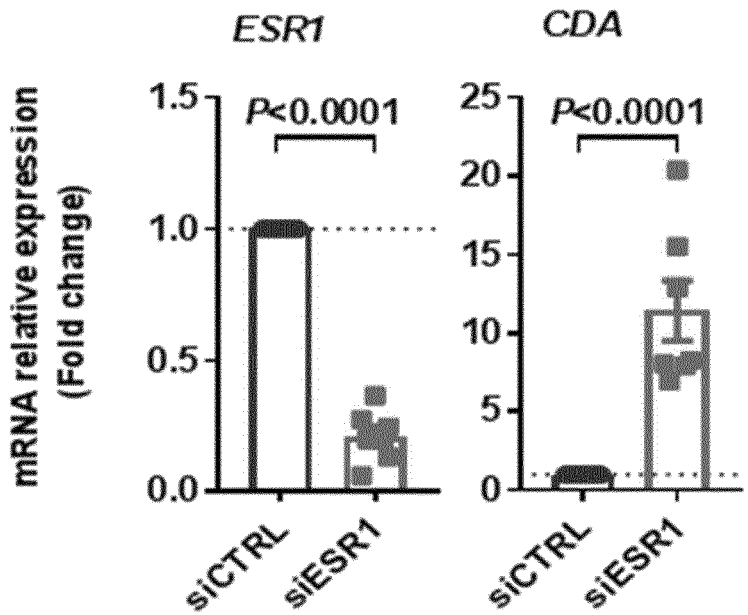
FIG. 12: A, qRT-PCR analysis of the downregulation of ESR1 expression in MCF-7 cells transiently transfected with the indicated siRNAs (left panel) and qRT-PCR analysis of the induction of CDA expression relative to GAPDH and TBP in MCF-7 cells transiently transfected with the indicated siRNAs (right panel) (n=7±SEM). B, Survival curves using MTT assay of estrogen receptor positive MCF-7 cells transiently transfected with indicated siRNAs and treated with Dasatinib for 72 h at the indicated concentrations (n=4±SEM). P values <0.05 are considered statically significant with t-test.
Figure 12:
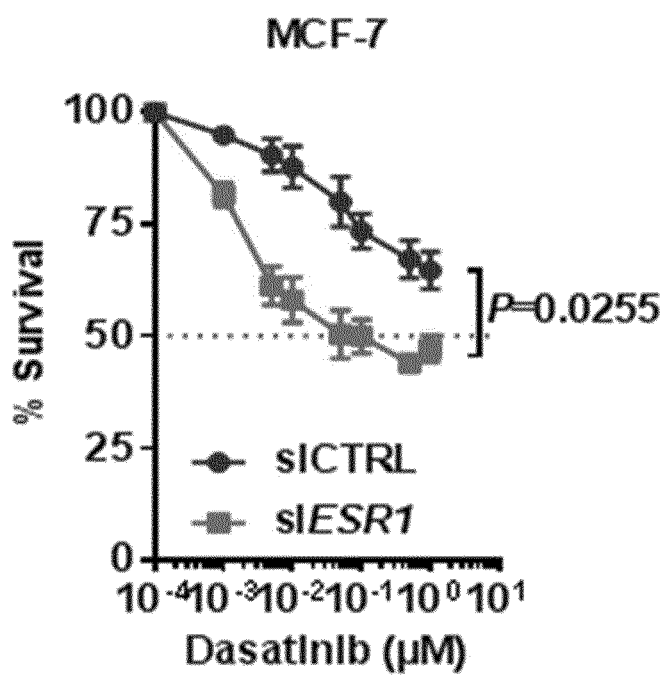

The inventors observed that most of the breast cancer cells expressing estrogen receptor (ERα), do not express CDA. To determine whether a link could exist between CDA and ERα expression, the gene coding for ERα, the ESR1 gene, was downregulated using specific siRNAs, and CDA expression level was analyzed. As shown in FIG. 12A (left panels), ESR1 silencing in MCF-7 cell lines strongly induces CDA expression.

As described above in FIG. 7, inventors found that CDA-proficient cancer cells were sensitive to dasatinib, whereas cells that do not express CDA or expressing low levels of CDA were resistant to dasatinib. To determine whether induction of CDA expression resulting from ESR1 downregulation could sensitize cells to dasatinib, MCF-7 control cells that express ESR1 but not CDA, and MCF-7 cells in which siRNA-mediated silencing of ESR1 led to induction of CDA expression (FIG. 12A), were treated with dasatinib for 72 h. As shown in FIG. 12B, ESR1 silencing in MCF-7 cells, induces CDA expression (FIG. 12A) and significantly enhanced sensitivity to dasatinib.

In conclusion, the present results suggest that (1) CDA expression is regulated, directly or indirectly, by ERα, and (2) induction of CDA by silencing ESR1 sensitizes breast cancer cells to dasatinib.

TABLE 1

Comparison of CDA mRNA expression data between cancerous and non-cancerous tissues, from the Gene Expression across Normal and Tumor Tissue database (GENT) and in TCGA samples.

| Tissue* | GENT (U133Plus2) | | P value (t-test) | TCGA (RNAseq) | | P value (t-test) |
|---|---|---|---|---|---|---|
| | Normal | Cancer | | Normal | Cancer | |
| Bladder# | 14 | 39 | 0.6645 | 18 | 182 | 0.8818 |
| Blood | 847 | 7786 | ***0.0002 | nd | nd | nd |
| Brain | 667 | 838 | ***0.0044 | nd | nd | nd |
| Breast | 267 | 2662 | ***<0.0001 | 106 | 994 | 0.4873 |
| Cervix# | 12 | 113 | 0.9908 | nd | nd | nd |
| Colon | 287 | 1994 | ***<0.0001 | 21 | 406 | ***0.0193 |
| Endometrium | 75 | 72 | ***0.0324 | nd | nd | nd |
| Head_neck | 14 | 202 | 0.132 | 42 | 303 | 0.4245 |
| Kidney Chromophobe | nd | nd | nd | 25 | 66 | **0.0004 |
| Kidney | 130 | 573 | **0.0148 | nd | nd | nd |
| Liver | 50 | 194 | ***<0.0001 | 49 | 134 | ***<0.0001 |
| Lung | 336 | 547 | **<0.0001 | nd | nd | nd |
| Lung Adenocarcinoma | nd | nd | nd | 58 | 470 | **0.0004 |
| Lung Squamous Cell Carcinoma | nd | nd | nd | 50 | 483 | 0.1913 |
| Ovary | 51 | 902 | 0.2868 | nd | nd | nd |
| Pancreas | 62 | 174 | **<0.001 | nd | nd | nd |
| Prostate | 51 | 314 | ***0.0005 | 45 | 195 | 0.3982 |
| Renal Clear Cell Carcinoma | nd | nd | nd | 71 | 480 | 0.269 |
| Renal Papillary Cell Carcinoma | nd | nd | nd | 30 | 141 | ***<0.0001 |
| Skin | 141 | 302 | ***<0.0001 | nd | nd | nd |
| Stomach | 57 | 311 | **<0.0001 | nd | nd | nd |
| Thyroid | 25 | 62 | 0.5812 | 58 | 494 | **<0.0001 |
| Uterus | 12 | 155 | ***0.0062 | 28 | 489 | 0.9383 |
| Vulva# | 14 | 21 | 0.8587 | nd | nd | nd |

*Are excluded cancer tissues without normal tissue counterparts and/or with less than 10 samples
Data to be interpreted with caution (limited number of samples < 20 for one of the two conditions)
**Upregulated
***Downregulated
nd: Not determined

TABLE 2A

Single-nucleotide polymorphisms identified by direct sequencing of the CDA gene (promoter, 5'UTR, exons and 3'UTR) from cancerous and non-cancerous breast cell lines.

| dbSNPs | | rs532545 | rs603412 | rs12726436 | rs602950 | rs3215400 | rs2072671 | | |
|---|---|---|---|---|---|---|---|---|---|
| Genomic position | | PROMOTER | | | | 5'UTR | EXON1 | EXON2 | EXON3 |
| and nucleotide change | | −451 C > T | −205 C > G | −182 G > A | −92 A > G | −33 delC | 79 A > C | | |
| SNP type | | ○ | ○ | ○ | ○ | ○ | ● | | |

| Cell lines | CDA expression | | | | | | | | |
|---|---|---|---|---|---|---|---|---|---|
| MDA-MB-468 | Low | | | | | — | | | |
| MDA-MB-361 | Low | | | | | —C/CC | AA AC/CC | | |
| HCC-1954 | Low | CC CT/CC | CC CG/CC | | AA AG/AA | —/CC | AA AC/CC | | |
| HCC-1187 | Low | | | | | — —/CC | | | |
| HCC-38 | Low | | CC GG/CC | GG AA/GG | | — —/CC | | | |
| MCF-7 | Low | | CC CG/CC | GG GA/GG | | — —/CC | | | |
| BT-474 | Low | | CC CG/CC | GG GA/GG | | — —C/CC | | | |
| BT-20 | Low | CC CT/CC | CC GG/CC | | AA GG/AA | — —/CC | AA CC/AA | | |
| HS578T | Low | CC CT/CC | CC CG/CC | | AA AG/AA | — —C/CC | AA AC/CC | | |
| SKBR3 | Low | | | | | — —/CC | | | |
| MDA-MB-231 | High | CC CT/CC | CC CG/CC | | AA AG/AA | — —C/CC | AA AG/CC | | |
| HCC-1143 | High | | | | | | | | |
| MCF-12A* | High | CC CT/CC | CC CG/CC | | AA AG/AA | — —C/CC | AA AC/CC | | |
| 184B5* | Weak | | | | | | | | |

| | | dbSNPs | rs1048977 | Chr1 20945219 | rs533655628 | rs398089164 |
|---|---|---|---|---|---|---|
| | | Genomic position and nucleotide change | EXON4 435 C > T | 599⁸ C > A | 3'UTR 637 C > A | 637-638 InC |
| | | SNP type | ○ | ○ | ○ | ○ |

| | Cell lines | CDA expression | | | | |
|---|---|---|---|---|---|---|
| | MDA-MB-468 | Low | CC TT/CC | | | CC CC/CC |
| | MDA-MB-361 | Low | CC CT/CC | CC CA/CC | CC CA/CC | CC —/CC |
| | HCC-1954 | Low | CC CT/CC | CC CA/CC | CC CA/CC | CC —/CC |
| | HCC-1187 | Low | CC TT/CC | | | CC CC/CC |
| | HCC-36 | Low | | CC CA/CC | CC CA/CC | |
| | MCF-7 | Low | CC TT/CC | | | CC CC/CC |
| | BT-474 | Low | CC CT/CC | | | CC —/CC |
| | BT-20 | Low | | | | |
| | HS578T | Low | CC CT/CC | | | CC —/CC |
| | SKBR3 | Low | CC TT/CC | | | CC CC/CC |
| | MDA-MB-231 | High | CC CT/CC | CC CA/CC | CC CA/CC | CC CA/CG |
| | HCC-1143 | High | | CC CA/CC | CC CA/CC | |
| | MCF-12A* | High | | | | |

TABLE 2A-continued

Single-nucleotide polymorphisms identified by direct sequencing of the CDA gene
(promoter, 5'UTR, exons and 3'UTR) from cancerous and non-cancerous breast cell lines.

| | | | | |
|---|---|---|---|---|
| 184B5* | Weak | CC | | CC |
| | | CT/CC | | —/CC |

*Non tumoral cells
According to western blotting analysis in FIG. 1b (Lower panel)
§Newly identified polymorphism
NM_001785 was used as a reference sequence
SNP: Single Nucleotide Polymorphism
● Missense
○ Silent

TABLE 2B

Single-nucleotide polymorphisms identified by exome sequencing of the CDA gene from the NCI60 panel cell lines.

| Cell line name dbSNPs | Tissue of origin | CDA | rs3215400 | rs2072671 | rs12059454 | rs61735378 | rs78249360 |
|---|---|---|---|---|---|---|---|
| | | Position | 5'UTR | Exon 1 | Intron (1-2) | Exon2 | Exon2 |
| | | Nucleotide change position # | −33 delC | 79 A > C | G > A | 208 G > A | 210 T > C |
| | | SNP type | ○ | ● | ○ | ○ | ○ |
| BR:MCF7 | Breast | Low | X | | | | |
| BR:MDA_MD_MB_231 | | High | | X | | | |
| BR:HS578T | | Low | X | X | | | |
| BR:BT_549 | | Low | | | | | |
| BR:T47D | | Low | | | | | |
| CNS:SF_268 | Central | Low | X | | | | |
| CNS:SF_295 | nervous | Low | | X | | | |
| CNS:SF_539 | system | Low | X | | X | | |
| CNS:SNB_19 | | Low | X | | | | X |
| CNS:SNB_75 | | Low | X | | | | |
| CNS:U251 | | Low | X | | | | X |
| CO:COLO205 | Colon | High | X | | | | |
| CO:HCC_2998 | | High | X | X | | | |
| CO:HCT_116 | | High | X | | | | |
| CO:HCT_15 | | Low | X | X | | | |
| CO:HT29 | | High | X | X | | | |
| CO:KM12 | | Low | | | | | |
| CO:SW_620 | | Low | | X | | | |
| LE:CCRF_CEM | Leukemia | Low | X | X | | | |
| LE:HL_60 | | Low | | | | | |
| LE:K_562 | | Low | X | X | | | |
| LE:MOLT_4 | | Low | X | | | | |
| LE:RPM_8226 | | Low | X | X | | X | |
| LE:SR | | Low | | | | | |
| ME:LOXMVI | Melanoma | High | | X | | | |
| ME:MALME_3M | | Low | | | | | |
| ME:M14 | | Low | X | X | | | |
| ME:SK_MEL_2 | | Low | | | | | |
| ME:SK_MEL_28 | | Low | X | | | | |
| ME:SK_MEL_5 | | High | | | | | |
| ME:UACC_257 | | Low | | | | | |
| ME:UACC_62 | | Low | X | X | | | |
| ME:MDA_MB_435 | | Low | | X | | | |
| ME:MDA_N | | Low | X | X | | | |
| LC:A549 | Non-Small | High | X | X | | | |
| LC:EKVX | Cell Lung | Low | | | | | |
| LC:HOP_62 | | High | X | | | | |
| LC:HOP_92 | | High | | | | | |
| LC:NCI_H226 | | Low | | X | | | |
| LC:NCI_H23 | | Low | X | | | | |
| LC:NCI_H322M | | Low | | | | | |
| LC:NCI_H460 | | Low | X | X | | | |
| LC:NCI_H522 | | Low | X | X | | | |
| OV:IGROV1 | Ovarian | Low | | | | | |
| OV:OVCAR_3 | | Low | | | | | |
| OV:OVCAR_4 | | Low | X | X | | | |
| OV:OVCAR_5 | | Low | X | X | | | |
| OV:OVCAR_8 | | High | | | | | |
| OV:SK_OV_3 | | High | X | X | | | |
| OV:NCI_ADR_RE | | High | X | | | | |
| PR:PC_3 | Prostate | High | X | | | | |
| PR:DU_145 | | High | | | | | |

TABLE 2B-continued

Single-nucleotide polymorphisms identified by exome sequencing of the CDA gene from the NCI60 panel cell lines.

| Cell line | Tissue | CDA | | | |
|---|---|---|---|---|---|
| RE:786_0 | Renal | Low | X | | |
| RE:A498 | | Low | | | |
| RE:ACHN | | Low | | | |
| RE:CAKI_1 | | Low | | | |
| RE:RXF_393 | | Low | X | X | |
| RE:SN12C | | High | X | X | |
| RE:TK_10 | | Low | | X | |
| RE:UO_31 | | High | | X | |

| Cell line name | Tissue of origin | CDA dbSNPs | rs149818257*2 | rs1048977 | chr1.20945075_C_T |
|---|---|---|---|---|---|
| Position | | | Intron (2-3) | Exon3 Exon4 | 3'UTR |
| Nucelotide change position # | | | C > T | 435 C > T | C > T |
| SNP type | | | ○ | ○ | ○ |
| BR:MCF7 | Breast | Low | | X | |
| BR:MDA_MD_MB_231 | | High | | | |
| BR:HS578T | | Low | | X | |
| BR:BT_549 | | Low | | | |
| BR:T47D | | Low | | | |
| CNS:SF_268 | Central | Low | | | |
| CNS:SF_295 | nervous | Low | | X | |
| CNS:SF_539 | system | Low | | | |
| CNS:SNB_19 | | Low | | X | |
| CNS:SNB_75 | | Low | | X | |
| CNS:U251 | | Low | | X | |
| CO:COLO205 | Colon | High | | X | |
| CO:HCC_2998 | | High | | | |
| CO:HCT_116 | | High | | X | |
| CO:HCT_15 | | Low | | | |
| CO:HT29 | | High | | | |
| CO:KM12 | | Low | | | |
| CO:SW_620 | | Low | | X | |
| LE:CCRF_CEM | Leu- | Low | | | |
| LE:HL_60 | kemia | Low | | | |
| LE:K_562 | | Low | | X | |
| LE:MOLT_4 | | Low | | X | |
| LE:RPM_8226 | | Low | | X | |
| LE:SR | | Low | | | |
| ME:LOXMVI | Mel- | High | | X | |
| ME:MALME_3M | anoma | Low | | X | |
| ME:M14 | | Low | | | |
| ME:SK_MEL_2 | | Low | | | X |
| ME:SK_MEL_28 | | Low | X | | |
| ME:SK_MEL_5 | | High | | | |
| ME:UACC_257 | | Low | | | |
| ME:UACC_62 | | Low | | | |
| ME:MDA_MB_435 | | Low | | | |
| ME:MDA_N | | Low | | | |
| LC:A549 | Non- | High | | X | |
| LC:EKVX | Small | Low | | X | |
| LC:HOP_62 | Cell | High | | X | |
| LC:HOP_92 | Lung | High | | | |
| LC:NCI_H226 | | Low | | | |
| LC:NCI_H23 | | Low | | X | |
| LC:NCI_H322M | | Low | | | |
| LC:NCI_H460 | | Low | | | |
| LC:NCI_H522 | | Low | | X | |
| OV:IGROV1 | Ovarian | Low | | | |
| OV:OVCAR_3 | | Low | | | |
| OV:OVCAR_4 | | Low | | X | |
| OV:OVCAR_5 | | Low | | X | |
| OV:OVCAR_8 | | High | | X | |
| OV:SK_OV_3 | | High | | X | |
| OV:NCI_ADR_RE | | High | | X | |
| PR:PC_3 | Prostate | High | | X | |
| PR:DU_145 | | High | | | |
| RE:786_0 | Renal | Low | | X | |
| RE:A498 | | Low | | | |
| RE:ACHN | | Low | | | |

TABLE 2B-continued

Single-nucleotide polymorphisms identified by exome sequencing of the CDA gene from the NCI60 panel cell lines.

| | | |
|---|---|---|
| RE:CAKI_1 | Low | |
| RE:RXF_393 | Low | |
| RE:SN12C | High | X |
| RE:TK_10 | Low | |
| RE:UO_31 | High | X |

CDA expression status was determined according to the NCI60 transcriptomic data

Deltected polymorphisms are in boxes with a large X

TABLE 3

Pearson positive correlation between the levels of CDA transcripts in cell lines from the NCI60 panel and the cytotoxicity of the compounds from the chemical library of the NCI. Each compound is represented by its National Service Center (NSC) identification number and optionally by its name and/or CAS number. The NSC is an identifier for substances submitted to the National Cancer Institute (NCI, USA) for testing and evaluation.

| Correlation coefficient | NSC number | Name | FDA Status |
|---|---|---|---|
| 0.559 | 630982 | triethyl 6a-amino-2,5-dimethyl-1,6-bis(phenylcarbamoylamino)pyrrolo[2,3-b]pyrrole-3,3a,4-tricarboxylate | — |
| 0.533 | 624721 | Benzenecarboximidamide,N,N-diphenyl- | — |
| 0.528 | 625558 | 8-[3-(6-hydroxyhexyl)thiiran-2-yl]octanoic acid | — |
| 0.528 | 625567 | methyl (4R)-3a-hydroxy-1,3,4-trimethyl-2,6-dioxo-3,4-dihydrofuro[3,4-b]pyrrole-6a-carboxylate | — |
| 0.524 | 625564 | trimethyl 2-[(E)-4-methoxy-4-oxobut-2-enoyl]-7-azabicyclo[2.2.1]heptane-1,3,4-tricarboxylate | — |
| 0.517 | 348900 | 4-[[1-(4-chlorobenzoyl)-3-methyl-5-oxo-4H-pyrazol-4-yl]diazenyl]-N-pyrimidin-2-ylbenzenesulfonamide | — |
| 0.515 | 625568 | 3a-hydroxy-6a-(hydroxymethyl)-1,3,4-trimethyl-3,4-dihydrofuro[3,4-b]pyrrole-2,6-dione | — |
| 0.511 | 707021 | 2,5-bis[(2,4,6-trimethylphenyl)sulfonyl]-1,6-dioxa-2,5-diazacycloundecane | — |
| 0.51 | 106486 | laurusin | — |
| 0.502 | 646371 | 7-amino-3-methyl-1H-quinoxalin-2-one|CAS: 69904-08-1 | — |
| 0.493 | 736160 | 3-(3-chloro-4-fluorophenyl)-6-(4-methoxyphenyl)-7H-[1,2,4]triazolo[3,4-b][1,3,4]thiadiazine | — |
| 0.491 | 643547 | (2Z)-2-[(3R,4S,6R,10S)-4,10-dihydroxy-3-[(3E,5Z)-6-(hydroxymethyl)-10-methylundeca-1,3,5,9-tetraen-2-yl]-6-(3-hydroxypropyl)-10-methylspiro[4.5]decan-7-ylidene]propanal | — |
| 0.483 | 618642 | 6-tert-butyl-4-[2-(chloromethoxy)-1,1,1,3,3,3-hexafluoropropan-2-yl]-1,1-bis(trifluoromethyl)spiro[2-benzofuran-3,10'-anthracene]-9'-one | — |
| 0.481 | 726198 | (3aS,5aR,6aS,10aS,10cS)-4-Methoxy-7,7,10a,10c-tetramethyl-2,3a,4,5a,6,6a,7,8,9,10,10a,10c-dodecahydro-3H-5-oxa-acephe nanthrylene | — |
| 0.481 | 670036 | 7-[3,4-dihydroxy-5-(hydroxymethyl)oxolan-2-yl]-1H-thieno[3,4-d]pyrimidine-4-thione | — |
| 0.476 | 646382 | (2Z)-N-(2-cyanophenyl)-2-[(4-nitrophenyl)hydrazinylidene]-2-(2,4,6-trioxo-1,3-diazinan-5-yl)acetamide | — |
| 0.475 | 732192 | dipterocaprol (hydroxydammarenone-11) | — |
| 0.469 | 293061 | 3,5-dibromo-N-(2-chloro-4-isothiocyanatophenyl)-2-hydroxybenzamide | — |
| 0.468 | 631942 | (6r,10s,11r)-26.xi.-hydroxy-13.xi.-oxaspiroirid-16-enal | — |
| 0.465 | 631581 | N-(3,4-dimethoxyphenyl)-3-phenyl-7-(trifluoromethyl)quinoxalin-2-amine | — |
| 0.464 | 662566 | ethyl 5-(4-chlorophenyl)-1H-pyrrole-2-carboxylate | — |
| 0.461 | 624351 | 1-naphthalen-1-yl-N-[2-(naphthalen-1-ylmethylideneamino)ethyl]methanimine | — |
| 0.458 | 650563 | (3Z)-2-amino-4-(3,4-dihydroxyphenyl)buta-1,3-diene-1,1,3-tricarbonitrile | — |
| 0.455 | 621868 | 3,5,6-trimethyl-2H-indazole-7-carboxylic acid | — |
| 0.453 | 622727 | (2E)-5-ethyl-2-(2-oxopropylidene)-1H-1,5-benzodiazepin-4-one | — |
| 0.452 | 741402 | (2E)-2-[(4,5-dimethoxy-2-methyl-3,6-dioxocyclohexa-1,4-dien-1-yl)methylidene]decanoic acid | — |
| 0.45 | 726272 | 3-[(4-chlorophenoxy)methyl]-6-(4-fluoro-3-phenoxyphenyl)-[1,2,4]triazolo[3,4-b][1,3,4]thiadiazole | — |

TABLE 3-continued

Pearson positive correlation between the levels of CDA transcripts in cell lines from the NCI60 panel and the cytotoxicity of the compounds from the chemical library of the NCI. Each compound is represented by its National Service Center (NSC) identification number and optionally by its name and/or CAS number. The NSC is an identifier for substances submitted to the National Cancer Institute (NCI, USA) for testing and evaluation.

| Correlation coefficient | NSC number | Name | FDA Status |
|---|---|---|---|
| 0.45 | 624352 | 5,9-Methano-4aH-benzocyclohepten-4a-ol, decahydro-10-methylene-9a-(methylsulfonyl)- | — |
| 0.446 | 621867 | Lestaurtinib | Clinical trial |
| 0.444 | 624350 | 2-(1-Hydroxy-2-isopropyl-5-methylcyclohexyl)acetamide | — |
| 0.444 | 619830 | 5-benzyl-5-methyl-2-sulfanylideneimidazolidin-4-one | — |
| 0.444 | 624208 | 2-(ethoxymethyl)-5-hydroxy-8,8-dimethyl-9,10-dihydropyrano[2,3-h]chromen-4-one | — |
| 0.443 | 259272 | sodium; [5-(6-aminopurin-9-yl)-3,4-dihydroxyoxolan-2-yl]methyl hydrogen phosphate | — |
| 0.441 | 622811 | 3,4,5-trihydroxy-6-[5-hydroxy-2-(4-hydroxyphenyl)-4-oxochromen-7-yl]oxyoxane-2-carboxylic acid | — |
| 0.437 | 699026 | [(1S,2R)-2,3-diacetyloxy-1-[(4S,5S)-5-(1,3-dithian-2-yl)-2,2-dimethyl-1,3-dioxolan-4-yl]propyl] acetate | — |
| 0.437 | 629740 | N-[3-[4-[3-(naphthalene-1-carbonylamino)propyl]piperazin-1-yl]propyl]naphthalene-1-carboxamide | — |
| 0.435 | 628637 | — | — |
| 0.433 | 626103 | 3-(2,3-dihydro-1H-indol-2-yl)-2,7-dimethyl-1H-indole | — |
| 0.431 | 655035 | N-[4-[(5-acetamido-1,3,4-thiadiazol-2-yl)sulfonyl]phenyl]acetamide | — |
| 0.43 | 618646 | 2-[2,6-ditert-butyl-4,4-bis(trifluoromethyl)-1,2-dihydro-3,1-benzoxazin-8-yl]-1,1,1,3,3,3-hexafluoropropan-2-ol | — |
| 0.43 | 624722 | (Z)-1-phenyl-1-(piperidin-1-yl)methanimine hydrochloride (CAS No. 41890-13-5) | — |
| 0.429 | 624404 | 2-[4-[bis(2-hydroxy-3-oxo-5-propan-2-ylcyclohepta-1,4,6-trien-1-yl)methyl]phenoxy]acetic acid | — |
| 0.429 | 39367 | 9-pentofuranosyl-6-(prop-2-en-1-ylsulfanyl)-9h-purine | — |
| 0.427 | 727100 | 2-[[5-[4-(1,3-benzoxazol-2-yl)phenyl]furan-2-yl]methylidene]propanedinitrile | — |
| 0.427 | 621864 | 9-acetyl-9a-methoxy-1,2-dihydrocarbazol-3-one | — |
| 0.426 | 719415 | 5-[(2,4-dichlorophenyl)methyl]-2-hydroxybenzo[b]carbazole-6,11-dione | — |
| 0.426 | 627019 | N-[2-[bis[2-[(1,5,7-trimethyl-2,4-dioxo-3-azabicyclo[3.3.1]nonane-7-carbonyl)amino]ethyl]amino]ethyl]-1,5,7-trimethyl-2,4-dioxo-3-azabicyclo[3.3.1]nonane-7-carboxamide | — |
| 0.426 | 618100 | (1R,4R)-1,4-bis(4-methoxyphenyl)-1,3a,4,6a-tetrahydrofuro[3,4-c]furan-3,6-dione | — |
| 0.419 | 622155 | 8,15-diisocyano-11(20)-amphilectene | — |
| 0.416 | 624769 | 5-(2-bromo-5-methoxyphenyl)pentanoic acid | — |
| 0.416 | 652812 | (3aS)-2-methyl-3-phenyl-3,3a,4,5-tetrahydrobenzo[g]indazole | — |
| 0.416 | 635393 | 4-(3-methyl-4H-1,4-benzothiazin-2-yl)-2,4-dioxo-N-phenylbutanamide | — |
| 0.416 | 619981 | [(5E,9E)-11-chloro-2-(hydroxymethyl)-6,10-dimethylundeca-1,5,9-trien-4-yl] acetate | — |
| 0.416 | 653003 | 10-methoxy-2,2-dimethyl-6-(2-phenylethyl)-3,4-dihydropyrano[3,2-g]chromen-8-one | — |
| 0.415 | 652195 | (4Z)-5-methyl-4-[(4-nitrophenyl)methylidene]-2-(2-phenylacetyl)pyrazol-3-one | — |
| 0.414 | 623773 | ethyl 2-[4-chloro-3-(trifluoromethyl)anilino]-2-oxoacetate | — |
| 0.414 | 619214 | dimethyl(1S)-6,7,8-trimethoxy-1-(3,4,5-trimethoxyphenyl)-1,2-dihydronaphthalene-2,3-dicarboxylate | — |
| 0.413 | 650998 | [4,5-diacetyloxy-6-(6-methyl-2-methylsulfanyl-4,7-dioxo-1H-pteridin-8-yl)oxan-3-yl]acetate | — |
| 0.412 | 653276 | (1-methoxycarbonylindol-2-yl)methyl-triphenylphosphanium; bromide | — |
| 0.412 | 651768 | N-[1,4-dioxo-3-(pentan-3-ylamino)naphthalen-2-yl]acetamide | — |
| 0.411 | 642738 | ethyl(1br)-6-oxo-1a,2,5,5a,6,6a-hexahydro-1bh-2,5-methanoindeno[1,2-b]oxirene-1b-carboxylate | — |
| 0.41 | 632479 | 1-(3,4-dimethoxyphenyl)-5,6-dimethoxy-2-(4-nitrophenyl)-3-[(4-nitrophenyl)methyl]indane | — |
| 0.41 | 208916 | (Z)-N-[1-hydroxy-3-(methylsulfanylmethylsulfanyl)propan-2-yl]-2-methyl-3-(6-methyl-2,4-dioxo-1H-pyrimidin-5-yl)prop-2-enamide | — |
| 0.41 | 209870 | Antibiotic A-31438 | — |
| 0.41 | 669992 | 4-benzyl-2-thiophen-2-yl-4,5-dihydro-1,3-oxazole | — |

TABLE 3-continued

Pearson positive correlation between the levels of CDA transcripts in cell lines from the NCI60 panel and the cytotoxicity of the compounds from the chemical library of the NCI. Each compound is represented by its National Service Center (NSC) identification number and optionally by its name and/or CAS number. The NSC is an identifier for substances submitted to the National Cancer Institute (NCI, USA) for testing and evaluation.

| Correlation coefficient | NSC number | Name | FDA Status |
|---|---|---|---|
| 0.409 | 624114 | pyreno[1,2-b]pyran-9-one | — |
| 0.408 | 366140 | Pyrazoloacridine | Clinical trial |
| 0.408 | 667869 | 1-diphenylboranyloxy-N,N-dimethyl-1-phenylpropan-2-amine | — |
| 0.407 | 341960 | psoralin, b-diethylamino-5-ethoxy- | — |
| 0.406 | 207111 | 3(2h)-isothiazolone,(z)-2-butenedioate(2:1) | — |
| 0.405 | 632621 | (9-methoxy-5,11-dimethyl-6H-pyrido[4,3-b]carbazol-2-ium-2-yl)methyl propanoate; iodide | — |
| 0.405 | 642418 | — | — |
| 0.402 | 624760 | (6-Chloro-8-methoxy-4,5-dihydro-3H-naphtho[1,8-bc]furan-2-yl)(phenyl)methanone | — |
| 0.402 | 628876 | 3-methyl-6,7-dihydro-1H-pyrrolo[2,3-d]pyrimidine-2,4,5-trione | — |
| 0.399 | 640351 | N-[2-nitro-4-(trifluoromethyl)phenyl]-2-oxo-2-(5-oxo-2-sulfanylideneimidazolidin-4-yl)acetamide | — |
| 0.398 | 201239 | (E)-3-(2,4-dioxo-1H-pyrimidin-5-yl)prop-2-enoic acid | — |
| 0.395 | 308881 | — | — |
| 0.394 | 13204 | 7-chloro-1,2,4-benzotriazin-3-amine | — |
| 0.394 | 163059 | (E)-3-(6-methyl-2,4-dioxo-1H-pyrimidin-5-yl)prop-2-enoic acid | — |
| 0.394 | 664570 | (6aS,13aS)-6a,8-dimethyl-7,8,13,13a-tetrahydro-5H-quinolino[4,3-b][1]benzazepin-6-one | — |
| 0.393 | 640547 | 3,4-dichloro-N-[[4-methyl-5-[(E)-3-(2-nitrophenyl)prop-2-enoyl]-1,3-thiazol-2-yl]carbamothioyl]benzamide | — |
| 0.392 | 641178 | 2-[(4-fluorophenyl)methylidene]indene-1,3-dione | — |
| 0.39 | 629413 | diethyl 7-(1-adamantyl)-9-oxo-2,4-diphenyl-3-oxa-7-azabicyclo[3.3.1]nonane-1,5-dicarboxylate | — |
| 0.387 | 702692 | 1-(2,3-dichloro-4,6-disulfamoylphenyl)-3-(3,4-dichlorophenyl)urea | — |
| 0.386 | 633552 | dimethyl 1',3'-dibenzyl-7,7-dimethyl-5-methylsulfanylspiro[8,8a-dihydro-4aH-thiochromene-4,2'-imidazolidine]-2,3-dicarboxylate | — |
| 0.385 | 627257 | 5-[[5-morpholin-4-yl-1-(4-nitrophenyl)triazol-4-yl]methyl]-2,3,4,5-tetraphenylcyclopent-2-en-1-one | — |
| 0.384 | 621866 | 2-(4-methoxyphenyl)-6,7-dimethyl-4-oxochromene-8-carboxylic acid | — |
| 0.384 | 625021 | 2-[3-[bis(2-hydroxyethyl)amino]-N-(2-hydroxyethyl)anilino]ethanol | — |
| 0.383 | 696563 | [[4-[(2,4-diaminopteridin-6-yl)methyl-methylamino]benzoyl]amino]methanesulfonic acid | — |
| 0.382 | 120958 | Furfuryladenosine | — |
| 0.382 | 312887 | Fludarabine | FDA approved |
| 0.382 | 740345 | 3-3'-(1h-pyrazole-3,5-diyl)bis(1-methyl-1h-indole) | — |
| 0.378 | 650825 | — | — |
| 0.378 | 624761 | (8-Methoxy-4,5-dihydro-3H-naphtho[1,8-bc]furan-2-yl)(phenyl)methanone | — |
| 0.376 | 626114 | 2-methyl-3-(7-methyl-2,3-dihydro-1H-indol-2-yl)-1H-indole | — |
| 0.376 | 679103 | 1,3,5-tris(azidomethyl)-2,4,6-trimethylbenzene | — |
| 0.375 | 635691 | 3-[(2E,5E)-2-[[3-(2-carboxyethyl)-5-[(E)-[(3E)-3-ethylidene-4-methyl-5-oxopyrrolidin-2-ylidene]methyl]-4-methyl-1H-pyrrol-2-yl]methylidene]-5-[(4-ethyl-3-methyl-5-oxopyrrol-2-yl)methylidene]-4-methylpyrrol-3-yl]propanoic acid | — |
| 0.375 | 719412 | 2-hydroxy-5-[(2-methoxyphenyl)methyl]benzo[b]carbazole-6,11-dione | — |
| 0.374 | 280594 | Triciribine phosphate | Clinical trial |
| 0.374 | 680857 | 3-ethyl-4-hydroxy-1H-1,2,4-triazol-5-one | — |
| 0.372 | 625565 | [(1S,5Z,10R)-10-(hydroxymethyl)cyclodec-5-en-3,7-diyn-1-yl]methanol | — |
| 0.372 | 133115 | 3-deazacytidine | — |
| 0.37 | 625566 | 8-methyl-2-phenyl-5-(1-trimethylsilyloxyethyl)-5,8-dihydro-[1,2,4]triazolo[1,2-a]pyridazine-1,3-dione | — |
| 0.369 | 740383 | [4-oxido-1-oxo-3,7-bis(trifluoromethyl)quinoxalin-1-ium-2-yl]-thiophen-2-ylmethanone | — |
| 0.369 | 759877 | Dasatinib | FDA approved |

TABLE 3-continued

Pearson positive correlation between the levels of CDA transcripts in cell lines from the NCI60 panel and the cytotoxicity of the compounds from the chemical library of the NCI. Each compound is represented by its National Service Center (NSC) identification number and optionally by its name and/or CAS number. The NSC is an identifier for substances submitted to the National Cancer Institute (NCI, USA) for testing and evaluation.

| Correlation coefficient | NSC number | Name | FDA Status |
|---|---|---|---|
| 0.369 | 626107 | 5-chloro-1-oxido-2-phenylindol-1-ium-3-one | — |
| 0.367 | 726197 | (5aR,10aS,10cR)-7,7,10a,10c-Tetramethyl-2,5a,6,6a,7,8,9,10,10a,10c-decahydro-4H-5-oxa-acephenanthrylene-3-carboxylic acid methyl ester | — |
| 0.366 | 102811 | formycin a | — |
| 0.366 | 669455 | 7-(4-nitrophenyl)-3-oxidotriazolo[4,5-g][2,1,3]benzoxadiazol-3-ium | — |
| 0.365 | 655430 | methyl 2-[5-bromo-2-[2-[(2-methylpropan-2-yl)oxycarbonylamino]ethyl]-1,3-thiazol-4-yl]-1,3-thiazole-4-carboxylate | — |
| 0.364 | 709311 | decipidone | — |
| 0.364 | 13119 | DL-Tryptophan | — |
| 0.364 | 720202 | N-(2,4-difluorophenyl)-N-(2-hydroxy-3-phenoxypropyl)-4-methylbenzenesulfonamide | — |
| 0.363 | 686965 | (5E)-5-ethylidene-2,3a,4,5a,10b,10c-hexahydro-1H-indeno[5,4-b][1]benzofuran-3-one | — |
| 0.362 | 734407 | 2,6-bis(benzylamino)-4-(4-oxocyclohexa-2,5-dien-1-ylidene)-1H-pyridine-3,5-dicarbonitrile | — |
| 0.362 | 631940 | (2Z)-2-[(3S,4R,5S,6R,10S)-3-[(3E,5E)-6,10-dimethylundeca-1,3,5,9-tetraen-2-yl]-4,10-dihydroxy-6-(3-hydroxypropyl)-10-methylspiro[4.5]decan-7-ylidene]propanal | — |
| 0.361 | 696469 | methyl 2-(1,1,3,3,7,7,9,9-octamethyl-2,8-dioxo-5,10-dithia-11-azadispiro[3.1.3^{6}.2^{4}]undecan-11-yl)acetate | — |
| 0.361 | 622492 | 6-hydroxysandoricin | — |
| 0.361 | 692227 | 2-amino-3-[[2-carboxy-2-(prop-2-ynylamino)ethyl]disulfanyl]propanoic acid | — |
| 0.361 | 335142 | 5,11-dimethyl-6H-pyrido[4,3-b]carbazole-1-carboxamide; hydrochloride | — |
| 0.361 | 693144 | 2,3-dimethoxy-5,6-dihydroisoquinolino[2,1-b]isoquinolin-8-one | — |
| 0.36 | 655928 | 3-benzylsulfanyl-4,7,7-trimethylbicyclo[4.1.0]heptan-4-ol | — |
| 0.36 | 726512 | phloeodictine A 1 | — |
| 0.359 | 640552 | N,N'-bis[5-[(E)-3-[4-[(E)-3-(2-amino-4-methyl-1,3-thiazol-5-yl)-3-oxoprop-1-enyl]phenyl]prop-2-enoyl]-4-methyl-1,3-thiazol-2-yl]decanediamide | — |
| 0.358 | 185060 | 1-[[(Z)-(5-oxopyridin-2-ylidene)methyl]amino]-3-phenylthiourea | — |
| 0.356 | 667527 | [3,4,5-triacetyloxy-6-(3-cyano-4-naphthalen-1-yl-2-sulfanylidene-5,6,7,8-tetrahydroquinolin-1-yl)oxan-2-yl]methyl acetate | — |
| 0.356 | 627506 | 6-(1H-indol-3-yl)-9-methyl-5,6,6a,7,8,10a-hexahydroindeno[2,1-b]indole | — |
| 0.356 | 667538 | [3,4,5-triacetyloxy-6-(5-cyano-3,4-dimethyl-2-phenyl-6-sulfanylidenepyridin-1-yl)oxan-2-yl]methyl acetate | — |
| 0.356 | 89822 | 5-amino-3-[4-hydroxy-5-(hydroxymethyl)oxolan-2-yl]-2H-triazolo[4,5-d]pyrimidin-7-one | — |
| 0.355 | 255523 | n6-benzyladenosine-5'-phosphate | — |
| 0.354 | 705998 | 2-amino-N'-(4-chlorophenyl)benzenecarboximidamide | — |
| 0.354 | 220471 | (E)-3-(2,4-dioxo-1H-pyrimidin-5-yl)-N,N-dimethylprop-2-enamide | — |
| 0.354 | 632243 | 2-[2-(4-chloro-2-methylanilino)-4-oxo-1,3-thiazol-5-yl]-N-(2,3-dimethylphenyl)acetamide | — |
| 0.353 | 656256 | [3,4,5-triacetyloxy-6-[4-(4-chlorophenyl)-5-cyano-2-methylsulfanyl-6-oxopyrimidin-1-yl]oxan-2-yl]methyl acetate | — |
| 0.352 | 718731 | 2-[(3,5-ditert-butyl-4-hydroxyphenyl)methyl]indene-1,3-dione | — |
| 0.351 | 758896 | fluvastatin | — |
| 0.35 | 671819 | 4-(furan-2-yl)-6-(4-methoxyphenyl)-2-sulfanylidene-1-[3,4,5-trihydroxy-6-(hydroxymethyl)oxan-2-yl]pyridine-3-carbonitrile | — |
| 0.35 | 722326 | 4-(1,3-benzodioxol-5-yl)-2-[(2E)-2-benzylidenehydrazinyl]-1-methyl-6-oxopyrimidine-5-carbonitrile | — |
| 0.349 | 67580 | 5,6,7,8-tetramethoxy-2-(3,4,5-trimethoxyphenyl)chromen-4-one | — |
| 0.349 | 726247 | 3-(3,4-dihydroxyphenyl)-4-(3,4,5-trihydroxyphenyl)-2H-furan-5-one | — |

TABLE 3-continued

Pearson positive correlation between the levels of CDA transcripts in cell lines from the NCI60 panel and the cytotoxicity of the compounds from the chemical library of the NCI. Each compound is represented by its National Service Center (NSC) identification number and optionally by its name and/or CAS number. The NSC is an identifier for substances submitted to the National Cancer Institute (NCI, USA) for testing and evaluation.

| Correlation coefficient | NSC number | Name | FDA Status |
|---|---|---|---|
| 0.349 | 650366 | N-[3-[(1,1-dioxo-1,2-benzothiazol-3-yl)amino]-2,2-dimethylpropyl]-2-(1,3-dioxoisoindol-2-yl)acetamide | — |
| 0.348 | 730188 | N-(3-chloro-4-fluorophenyl)-4-(3-chlorophenyl)-6-methyl-2-sulfanylidene-3,4-dihydro-1H-pyrimidine-5-carboxamide | — |
| 0.347 | 622921 | 6-(1-benzofuran-2-yl)-4-(4-methylpiperidin-1-yl)-2-oxopyran-3-carbonitrile | — |
| 0.346 | 704868 | (5Z)-2-butylsulfanyl-5-[[4-(dimethylamino)phenyl]methylidene]-1H-imidazol-4-one | — |
| 0.345 | 633781 | Lovastatin | — |
| 0.345 | 401077 | 2-(1,3-dioxoisoindol-2-yl)-3-(1H-indol-3-yl)propanoic acid | — |
| 0.345 | 694051 | — | — |
| 0.345 | 623959 | 1-methyl-3,4-dihydro-2H-pyrido[3,4-b]indole-3-carboxylic acid | — |
| 0.344 | 124463 | Fludarabine | FDA approved |
| 0.342 | 699246 | 1-(2-phenoxyethyl)-5-(3-methylphenylamino)uracil | — |
| 0.342 | 728413 | 4-fluoro-N-[4-[(E)-3-(4-hydroxyphenyl)prop-2-enoyl]phenyl]-3-methoxybenzenesulfonamide | — |
| 0.342 | 617595 | isoxazolyl-prodrug of distamycin (stallimycin) | — |
| 0.341 | 672446 | benzyl 4-oxo-4-[[2-oxo-2-propan-2-yloxy-1-[(2,2,5,5-tetramethylcyclopentanecarbonyl)amino]ethyl]amino]-3-(phenylmethoxycarbonylamino)butanoate | — |
| 0.34 | 680666 | N-[4-chloro-5-(2-chloroethyl)-6-methylpyrimidin-2-yl]-1H-benzimidazol-2-amine | — |
| 0.34 | 705333 | (4Z)-2-tert-butyl-5,7-dimethoxy-4-(phenylsulfanylmethylidene)-1H-isoquinolin-3-one | — |
| 0.34 | 630450 | (1R,2S,3R)-3-(5-hydroxypent-1-en-2-yl)-1,2-dimethylcyclopentan-1-ol | — |
| 0.34 | 678362 | methyl 5-methyl-2-[(E)-(4-methyl-3-oxo-1H-inden-2-ylidene)methyl]benzoate | — |
| 0.339 | 640340 | N'-[(E,3Z)-1-[2-(3,4-dichloroanilino)-4-methyl-1,3-thiazol-5-yl]-3-(3-methoxy-4-oxocyclohexa-2,5-dien-1-ylidene)prop-1-enyl]benzohydrazide | — |
| 0.339 | 654622 | 5-azido-2-methyl-6-phenylpyridazin-3-one | — |
| 0.339 | 655345 | N-[(5E)-5-[(2,4-dimethoxyphenyl)methylidene]-4-oxo-2-phenylimino-1,3-thiazolidin-3-yl]-2-phenylacetamide | — |
| 0.338 | 671341 | 1-(2,4-dichloroanilino)-3-(2,4-dichlorophenyl)iminourea | — |
| 0.338 | 731358 | 7-benzylsulfanyl-5-(furan-2-yl)-2,4-bis(sulfanylidene)-1H-pyrido[2,3-d]pyrimidine-6-carbonitrile | — |
| 0.338 | 667079 | 2-[(4-amino-5-phenyl-6,7,8,9-tetrahydropyrimido[4,5-b]quinolin-2-yl)sulfanyl]-1-phenylethanone | — |
| 0.337 | 634049 | — | — |
| 0.337 | 709588 | 7-(diethylamino)-3-(3-phenyl-1H-1,2,4-triazol-5-yl)chromen-2-one | — |
| 0.336 | 638462 | methyl (2E,4E,6E,8E)-9-(4-ethynyl-1,3,5-trimethylpyrrol-2-yl)-3,7-dimethylnona-2,4,6,8-tetraenoate | — |
| 0.335 | 752330 | 2-(hydroxymethyl)-5-[6-(2-propan-2-ylidenehydrazinyl)purin-9-yl]oxolane-3,4-diol | — |
| 0.335 | 683605 | (1E)-2-anilino-N-[(5-carbamoyl-1H-imidazol-4-yl)amino]-2-oxoethanimidoyl cyanide | — |

TABLE 4

Pearson negative correlation between the levels of CDA transcripts in cell lines from the NCI60 panel and the cytotoxicity of the compounds from the chemical library of the NCI. Each compound is represented by its National Service Center (NSC) identification number and optionally by its name and/or CAS number.

| Correlation coefficient | NSC number | Name | FDA Status |
|---|---|---|---|
| −0.335 | 701102 | 6-chloro-3-(6-chloroimidazo[1,2-a]pyridin-2-yl)chromen-2-one | — |
| −0.335 | 733164 | 5-hydroxyamino camptothecin | — |
| −0.335 | 702327 | 2-[(2E,6E,10E,14E,18Z,22E,26E)-19-(hydroxymethyl)-3,7,11,15,23,27,31-heptamethyldotriaconta-2,6,10,14,18,22,26,30-octaenyl]benzene-1,4-diol | — |

TABLE 4-continued

Pearson negative correlation between the levels of CDA transcripts in cell lines from the NCI60 panel and the cytotoxicity of the compounds from the chemical library of the NCI. Each compound is represented by its National Service Center (NSC) identification number and optionally by its name and/or CAS number.

| Correlation coefficient | NSC number | Name | FDA Status |
|---|---|---|---|
| −0.335 | 702337 | 3-(2-methoxyphenyl)-2-(3,4,5-trimethoxyphenyl)-1,3-thiazolidin-4-one | — |
| −0.336 | 746035 | 2-[4-[5-[2,6-dimethoxy-4-[5-(3,4,5-trimethoxyphenyl)-4,5-dihydro-1,2-oxazol-3-yl]phenoxy]pentoxy]-3-methoxyphenyl]-2,3-dihydro-1H-quinazolin-4-one | — |
| −0.337 | 378731 | Cephalostatin 5 | — |
| −0.337 | 602849 | 2,9-Bis(chloromethyl)-1,10-phenanthroline | — |
| −0.338 | 400770 | [4-(4-hydroxyphenyl)phenyl]-phenylmethanone | — |
| −0.339 | 697665 | 2-(4-chlorophenyl)-6-fluoro-5-(4-methylpiperazin-1-yl)-1H-benzimidazole | — |
| −0.34 | 703776 | 3-[2-[2-(4-chlorophenyl)-4-oxo-1,3-thiazinan-2-yl]-1-phenylethyl]sulfanylpropanoic acid | — |
| −0.34 | 31460 | — | — |
| −0.341 | 681229 | [(1R)-1-[[(2S)-2-amino-3-naphthalen-1-ylpropanoyl]amino]-3-methylbutyl]boronic acid; hydrochloride | — |
| −0.342 | 718660 | 4-[3-chloro-2-oxo-4-[(E)-2-phenylethenyl]azetidin-1-yl]-1,5-dimethyl-2-phenylpyrazol-3-one | — |
| −0.342 | 142055 | 1-butyl-5-methyl-6H-pyrido[4,3-b]carbazole | — |
| −0.343 | 688846 | — | — |
| −0.343 | 13300 | N-(7-chloroquinolin-4-yl)-N',N'-diethyl-2-(4-methoxyphenyl)butane-1,4-diamine | — |
| −0.343 | 341651 | senecioylchaparrin, 6-alpha-(b815099k220) | — |
| −0.344 | 746513 | 2-(2-chlorophenyl)-3-[5-(1,2,4-triazol-4-ylmethyl)-1,3,4-oxadiazol-2-yl]-1,3-thiazolidin-4-one | — |
| −0.344 | 629734 | N,N'-bis(naphthalen-1-ylmethyl)dodecane-1,12-diamine | — |
| −0.346 | 648424 | 1,2,3,6-tetramethoxynaphtho[2,1-f][1,3]benzodioxole | — |
| −0.347 | 712708 | N-[1-(2,3-dihydro-1,4-benzodioxin-6-yl)ethyl]-3,4,5-trimethoxyaniline | — |
| −0.348 | 737155 | borrelidin 3,11-bis-o-formyl ester | — |
| −0.349 | 638497 | (z) 4-acetoxy-3',4',5'-trimethoxystilbene | — |
| −0.351 | 124147 | harringtonin | — |
| −0.352 | 641233 | N-(3-chloro-1,4-dioxonaphthalen-2-yl)-4-naphthalen-2-yl-2,4-dioxo-3-(3-oxo-1H-2-benzofuran-1-yl)butanamide | — |
| −0.352 | 716172 | (5Z)-5-[(4-methylsulfanylphenyl)methylidene]-2-phenyl-3-(5-propylsulfanyl-1H-indol-2-yl)imidazol-4-one | — |
| −0.353 | 639515 | (2E)-2-(1,3-benzodioxol-5-ylmethylidene)-5-[(dimethylamino)methyl]cyclopentan-1-one; hydrochloride | — |
| −0.354 | 703315 | 3-chloroindolo[2,1-b]quinazoline-6,12-dione | — |
| −0.354 | 106648 | bis(2-methoxy-5-nitrophenyl)iodanium; bromide | — |
| −0.355 | 138780 | insariotoxin | — |
| −0.355 | 636097 | 3-N,5-N-bis(2-methoxyphenyl)-2,6-dimethyl-4-(2H-pyran-3-yl)-1,4-dihydropyridine-3,5-dicarboxamide | — |
| −0.355 | 294858 | — | — |
| −0.356 | 700202 | 2-(furan-2-yl)-1-methyl-3,5-dithiophen-2-ylpyrrole | — |
| −0.358 | 681242 | [(1R)-3-methyl-1-(3-phenylpropanoylamino)butyl]boronic acid | — |
| −0.359 | 733345 | tetramethyl (1R,5S,6S,9S)-3-(4-chlorobenzoyl)oxy-7-(2-chlorophenyl)-5-hydroxybicyclo[3.3.1]non-2-ene-2,4,6,9-tetracarboxylate | — |
| −0.36 | 681231 | N-(4-MORPHOLINE)CARBONYL-B-(1-NAPHTHYL)-L-ALANINE-L-LEUCINE BORONIC ACID | — |
| −0.36 | 269756 | baccharinol | — |
| −0.363 | 681684 | 3,17-dihydroxy-13-methyl-2-(2,2,2-trifluoroethoxy)-8,9,11,12,14,15,16,17-octahydro-7H-cyclopenta[a]phenanthren-6-one | — |
| −0.363 | 673320 | N,N-diethylethanamine; 6-[2-(4-hydroxy-3-nitrophenyl)ethylamino]-1H-benzimidazole-4,7-dione | — |
| −0.363 | 693365 | — | — |
| −0.364 | 175493 | — | — |
| −0.366 | 670406 | spiro[1,3-dihydroindene-2,2'-3,6,7,8-tetrahydro-1H-cyclopenta[g]naphthalene]-5'-one | — |
| −0.367 | 174518 | 2-N,6-N-dimethyl-4,4-dioxo-2-N,6-N-diphenyl-1,4,3,5-oxathiadiazine-2,6-diamine | — |
| −0.368 | 658388 | 2-[4-(dimethylamino)butyl]-9-methyl-3,4-dihydropyrido[3,4-b]indol-1-one; hydrochloride | — |
| −0.368 | 752702 | (3Z)-3-[(4-hydroxy-3,5-dimethoxyphenyl)methylidene]-1H-indol-2-one | — |

TABLE 4-continued

Pearson negative correlation between the levels of CDA transcripts in cell lines from the NCI60 panel and the cytotoxicity of the compounds from the chemical library of the NCI. Each compound is represented by its National Service Center (NSC) identification number and optionally by its name and/or CAS number.

| Correlation coefficient | NSC number | Name | FDA Status |
|---|---|---|---|
| −0.369 | 5366 | Noscapine | — |
| −0.369 | 378732 | Cephalostatin 6 | — |
| −0.371 | 711866 | (5Z)-5-[(4-hydroxy-3-methoxyphenyl)methylidene]-2-phenyl-3-(6-phenyl sulfanyl-1H-benzimidazol-2-yl)imidazol-4-one | — |
| −0.372 | 705591 | (2E,5E)-2,5-bis[(4-hydroxy-3,5-dimethoxyphenyl)methylidene]cyclopentan-1-one | — |
| −0.375 | 650738 | 9-butyl-10-oxido-1,2,3,4,5,6,7,8-octahydroacridin-10-ium | — |
| −0.377 | 715806 | (3E,6E)-3-[(4-chlorophenyl)methylidene]-6-[(5-phenylmethoxypyridin-2-yl)methylidene]piperazine-2,5-dione | — |
| −0.377 | 730294 | (3E)-5-methoxy-3-(pyridin-4-ylmethylidene)-1H-indol-2-one | — |
| −0.379 | 710464 | AFP464; Aminoflavone | Clinical trial |
| −0.382 | 629621 | 4-N-[10-[(2-amino-6-chloropyrimidin-4-yl)amino]decyl]-6-chloropyrimidine-2,4-diamine | — |
| −0.384 | 652675 | — | — |
| −0.386 | 748266 | [5-amino-3-(2-methoxyphenyl)imidazol-4-yl]-(3,4,5-trimethoxyphenyl)methanone | — |
| −0.389 | 730214 | AC1LMEUE-N-(2-methoxyphenyl)-5-methyl-4-oxo-3-(2-phenoxyethyl)thieno[2,3-d]pyrimidine-6-carboxamide | — |
| −0.389 | 710272 | 4-[4-(4-pyridin-4-ylphenoxy)phenyl]pyridine | — |
| −0.392 | 677240 | (1E,4E)-1,5-bis(2,4-dimethoxyphenyl)penta-1,4-dien-3-one | — |
| −0.394 | 681237 | [(1R)-3-methyl-1-[[(2S)-2-(methylamino)-3-naphthalen-1-ylpropanoyl]amino]butyl]boronic acid; hydrochloride | — |
| −0.394 | 640534 | (E)-1-(2-chlorophenyl)-3-naphthalen-1-ylprop-2-en-1-one | — |
| −0.396 | 327993 | roridin a, 8-hydroxy-9b,10b-epoxy- | — |
| −0.396 | 751502 | — | — |
| −0.401 | 721070 | — | — |
| −0.405 | 711891 | (5Z)-3-[4-benzoyl-2-[(4Z)-5-oxo-4-[(3-phenoxyphenyl)methylidene]-2-phenylimidazol-1-yl]phenyl]-5-[(3-phenoxyphenyl)methylidene]-2-phenylimidazol-4-one | — |
| −0.407 | 661114 | physalin O | — |
| −0.413 | 668393 | 6-[2-(3,5-dibromo-4-hydroxyphenyl)ethylamino]quinoline-5,8-dione | — |
| −0.413 | 328166 | 8B-hydroxy-9B,10B-epoxyverrucarin A | — |
| −0.416 | 668382 | trihydroxy-azatoxin | — |
| −0.42 | 703558 | N-[3-[[[(6aS)-2-methoxy-11-oxo-6a,7,8,9-tetrahydropyrrolo[2,1-c][1,4]benzodiazepin-3-yl]oxy]propyl]-1H-indole-2-carboxamide | — |
| −0.421 | 681234 | Boronic acid, S- | — |
| −0.422 | 35676 | purpurogallin | — |
| −0.426 | 670159 | (1R,4R)-4,11,11-trimethyl-8-methylidene-5-nitro-4-nitrosobicyclo[7.2.0]undecane | — |
| −0.436 | 378727 | Cephalostatin 4 | — |
| −0.439 | 657593 | 4-[2-[2-[(5Z)-5-(1,3-benzodioxol-5-ylmethylidene)-4H-1,3-thiazol-2-yl]hydrazinyl]-1,3-thiazol-4-yl]benzene-1,2-diol | — |
| −0.452 | 638492 | (z) 3,3',4,5-tetramethoxystilbene | — |
| −0.454 | 622918 | 2-nitro-N-(1-phenyl-9H-pyrido[3,4-b]indol-6-yl)benzamide | — |
| −0.472 | 376251 | ethyl N-[(7S)-3-hydroxy-1,2-dimethoxy-10-methylsulfanyl-9-oxo-6,7-dihydro-5H-benzo[a]heptalen-7-yl]carbamate | — |
| −0.506 | 729165 | N'-octyl-4-[4-(N'-octylcarbamimidoyl)phenyl]piperazin-1-yl]benzenecarboximidamide; hydrochloride | — |
| −0.565 | 264880 | Dihydro-5-azacytidine | — |
| −0.585 | 746886 | 7,8-dichloro-1'-ethyl-9-methyl-1-oxospiro[2,4-dihydropyrido[3,4-b]indole-3,4'-piperidine]-4-carbonitrile | — |

TABLE 5

Cell-lines of the study and their culture media

| Cell lines | Tissue of origin | HER2 | ER | PR | P53 | Media |
|---|---|---|---|---|---|---|
| MCF-12A | Normal breast | Negative | Negative | Negative | Wild type | DMED/F 12 + 5% Horse serum + 20 ng/ml EGF + |
| 184B5 | | Negative | Negative | Negative | | |

TABLE 5-continued

Cell-lines of the study and their culture media

| Cell lines | Tissue of origin | HER2 | ER | PR | P53 | Media |
|---|---|---|---|---|---|---|
| BT-474 | Breast carcinoma adenocarcinoma | Positive | Positive | Positive | Mutant | 100 ng/ml cholera toxin + 0.01 mg/ml insulin + 500 ng/ml hydrocodisone RPMI-1640 + 1% glutamine + 1.5 g/l sodium bicarbonate + 1% Penicillin/streptomycin + 10% FBS |
| SKBR3 | | Positive | Negative | Negative | Mutant | McCoy's 5a MM + Penicillin/streptomycin + 10% FBS |
| BT-20 | | Negative | Negative | Negative | Mutant | MEM(Eagle) + 1% glutamax + 1% Penicillin/streptomycin + 10% FBS + 1.5 g/L sodium bicarbonate + 0.1 mM non-essential aa + 1 mM sodium pyruvate |
| MDA-MB-436 | | Negative | Negative | Negative | Mutant | L15 + 1% glutamine + 1% Penicillin/streptomycin + 10% FBS without $CO_2$ |
| MDA-MB-361 | | Positive | Positive | Positive | Mutant/WT | DMEM + 1% glutamine + 1% Penicillin/streptomycin + 10% FBS |
| MCF-7 | | Negative | Positive | Positive | Wild type | |
| HS578T | | Negative | Negative | Negative | Mutant | |
| MDA-MB-231 | | Negative | Negative | Negative | Mutant | |
| HCC-38 | | Negative | Negative | Negative | Mutant | RPMI-1640 + 1% glutamax + 1% Penicillin/streptomycin + 10% FBS + 1.5 g/L sodium bicarbonate + 10 mM HEPES + 1mM sodium pyruvate |
| HCC-70 | | Negative | Negative | Negative | | |
| HCC-1937 | | Negative | Negative | Negative | Mutant | |
| HCC-1143 | | Negative | Negative | Negative | Mutant/WT | |
| BT-549 | | Negative | Negative | Negative | Mutant | |
| HCC-1187 | | Negative | Negative | Negative | Mutant/WT | |
| MDA-MB-468 | | Negative | Negative | Negative | Mutant | RPMI-1640 + 1% glutamine + 1% Penicillin/streptomycin + 10% FBS |
| T47D | | Negative | Positive | Positive | Mutant | |
| HCC-1954 | | Positive | Negative | Negative | Mutant | |
| HCC-1428 | | Positive | Negative | Negative | | |
| ZR-75-1 | | Negative | Positive | Negative | Wild type | |
| HOP-92 | Lung | | | | Mutant | |
| HOP-62 | | | | | Mutant | |
| H522 | | | | | Mutant | |
| H23 | | | | | Mutant | |
| IGROV-1 | Ovary | | | | Mutant | |
| SKOV-3 | | | | | ? | |
| OVCAR-8 | | | | | Mutant | |
| A2058 | Melanoma | | | | | MEM(Eagle) + 1% glutamine + 1% Penicillin/streptomycin + 10% FBS |

HER2: Tyrosine Kinase-Type Cell Surface Receptor,
ER: Estrogen Receptor 1,
PR: Progesterone receptor,
P53 : Tumor protein 53

TABLE 6

Primers for amplification (RT-PCR) and nucleotide sequencing

| Region | Primer | Sequence (5'-3') | Tm (° C.) | Amplicon size (bp) | Reference |
|---|---|---|---|---|---|
| Promoter and exon 1 | F1 | AAC GGG ATG ACT TAT TGA GGT (SEQ ID NO: 1) | 60 | 1,800 | This study |
| | R1 | CAT CTT CCT CTG ACC CAC CA (SEQ ID NO: 2) | 62 | | |
| Exon 2 | F2 | ATT GCC CTG TCC TTC TCC C (SEQ ID NO: 3) | 60 | 407 | |

TABLE 6-continued

Primers for amplification (RT-PCR) and nucleotide sequencing

| Region | Primer | Sequence (5'-3') | Tm (° C.) | Amplicon size (bp) | Reference |
|---|---|---|---|---|---|
|  | R2 | TAT CCT CAG CAC TCA TCC CA (SEQ ID NO: 4) | 60 |  |  |
| Exon 3 | F3 | CCA AAT CAG GAA CAG ACC GA (SEQ ID NO: 5) | 60 | 379 |  |
|  | R3 | CAC AAA GCA GAC ACT CAC TC (SEQ ID NO: 6) | 60 |  |  |
| Exon 4 | F4 | AGC ATT CTT TCG TTT CCT CCT (SEQ ID NO: 7) | 60 | 1,054 |  |
|  | R4 | ATC TCC ACA CCC TCC TCA C (SEQ ID NO: 8) | 60 |  |  |

In bold primers used for sequencing

TABLE 7

Primers for RT-qPCR analysis

| | | | | | |
|---|---|---|---|---|---|
| CDA | F | CCC TAC AGT CAC TTT CCT G (SEQ ID NO: 9) | 60 | 91 | Chabosseau et al., Nat Comms 2011 |
|  | R | CGG GTA GCA GGC ATT TTC TA (SEQ ID NO: 10) | 60 | | |
| GAPDH | F | GAA ATC CCA TCA CCA TCT TCC AGG (SEQ ID NO: 11) | 60 | 120 | West et al., J Biol Chem 2004 |
|  | R | GAG CCC CAG CCT TCT CCA TG (SEQ ID NO: 12) | 60 | | |
| TBP | F | TGC ACA GGA GCC AAG AGT GAA (SEQ ID NO: 13) | 60 | 132 | Pasmant et al., Mol Med 2011 |
|  | R | CAC ATC ACA GCT CCC CAC CA (SEQ ID NO: 14) | 60 | | |

TABLE 8

Primary and secondary antibodies for Western-blot

| | Target | Reference | Dilution | Buffer |
|---|---|---|---|---|
| Primary antibody | CDA | Anti-CDA (ab56053)-Abcam | 1/500 | Milk (5%) in PBS-Tween 0.05% |
|  | hsp90 | Anti-Hsp90 alpha (ab2928)-Abcam | 1/10,000 | |
|  | b-Actin | Anti-Actin-beta, (SAB5500001)-Sigma | 1/10,000 | |
|  | GAPDH | GAPDH Antibody (6C5), SC-32233-Santa Cruz | 1/10,000 | |
| Secondary antibody | Goat anti-rabbit IgG | Goat anti rabbit HRP SC-2054-Santa Cruz | 1/5,000 | |
|  | Goat anti-mouse IgG | Goat anti mouse HRP SC-2055-Santa Cruz | 1/5,000 | |

TABLE 9

Primary antibody for Immunohistochemistry

| | Target | Reference | Dilution | Buffer |
|---|---|---|---|---|
| Primary antibody | CDA | Anti-CDA (ab82347)-Abcam | 1/300 | 5% NGS PBS-Tween |

REFERENCES

1. Chen Z, Shi T, Zhang L, Zhu P, Deng M, Huang C, et al. Mammalian drug efflux transporters of the ATP binding cassette (ABC) family in multidrug resistance: A review of the past decade. Cancer Lett. 2016; 370:153-64.
2. Amor-Guéret M. Bloom syndrome, genomic instability and cancer: the SOS-like hypothesis. Cancer Lett. 2006; 236:1-12.
3. Chabosseau P, Buhagiar-Labarchède G, Onclercq-Delic R, Lambert S, Debatisse M, Brison O, et al. Pyrimidine pool imbalance induced by BLM helicase deficiency contributes to genetic instability in Bloom syndrome. Nat Commun. 2011; 2:368.
4. Demontis S, Terao M, Brivio M, Zanotta S, Bruschi M, Garattini E. Isolation and characterization of the gene coding for human cytidine deaminase. Biochim Biophys Acta. 1998; 1443:323-33.
5. Cacciamani T, Vita A, Cristalli G, Vincenzetti S, Natalini P, Ruggieri S, et al. Purification of human cytidine deaminase: molecular and enzymatic characterization and inhibition by synthetic pyrimidine analogs. Arch Biochem Biophys. 1991; 290:285-92.
6. Neff T, Blau C A. Forced expression of cytidine deaminase confers resistance to cytosine arabinoside and gemcitabine. Exp Hematol. 1996; 24:1340-6.
7. Weizman N, Krelin Y, Shabtay-Orbach A, Amit M, Binenbaum Y, Wong R J, et al. Macrophages mediate gemcitabine resistance of pancreatic adenocarcinoma by upregulating cytidine deaminase. Oncogene. 2014; 33:3812-9.
8. Ciccolini J, Dahan L, André N, Evrard A, Duluc M, Blesius A, et al. Cytidine deaminase residual activity in serum is a predictive marker of early severe toxicities in adults after gemcitabine-based chemotherapies. J Clin Oncol Off J Am Soc Clin Oncol. 2010; 28:160-5.
9. Sugiyama E, Kaniwa N, Kim S-R, Kikura-Hanajiri R, Hasegawa R, Maekawa K, et al. Pharmacokinetics of gemcitabine in Japanese cancer patients: the impact of a cytidine deaminase polymorphism. J Clin Oncol Off J Am Soc Clin Oncol. 2007; 25:32-42.
10. Yue L, Saikawa Y, Ota K, Tanaka M, Nishimura R, Uehara T, et al. A functional single-nucleotide polymorphism in the human cytidine deaminase gene contributing to ara-C sensitivity. Pharmacogenetics. 2003; 13:29-38.
11. Farrell J J, Bae K, Wong J, Guha C, Dicker A P, Elsaleh H. Cytidine deaminase single-nucleotide polymorphism is predictive of toxicity from gemcitabine in patients with pancreatic cancer: RTOG 9704. Pharmacogenomics J. 2012; 12:395-403.
12. Monzo M, Brunet S, Urbano-Ispizua A, Navarro A, Perea G, Esteve J, et al. Genomic polymorphisms provide prognostic information in intermediate-risk acute myeloblastic leukemia. Blood. 2006; 107:4871-9.
13. Fitzgerald S M, Goyal R K, Osborne W R A, Roy J D, Wilson J W, Ferrell R E. Identification of functional single nucleotide polymorphism haplotypes in the cytidine deaminase promoter. Hum Genet. 2006; 119:276-83.
14. Okazaki T, Javle M, Tanaka M, Abbruzzese J L, Li D. Single nucleotide polymorphisms of gemcitabine metabolic genes and pancreatic cancer survival and drug toxicity. Clin Cancer Res Off J Am Assoc Cancer Res. 2010; 16:320-9.
15. Mahlknecht U, Dransfeld C-L, Bulut N, Kramer M, Thiede C, Ehninger G, et al. SNP analyses in cytarabine metabolizing enzymes in AML patients and their impact on treatment response and patient survival: identification of CDA SNP C-451T as an independent prognostic parameter for survival. Leukemia. 2009; 23:1929-32.
16. Ye F-G, Song C-G, Cao Z-G, Xia C, Chen D-N, Chen L, et al. Cytidine Deaminase Axis Modulated by miR-484 Differentially Regulates Cell Proliferation and Chemoresistance in Breast Cancer. Cancer Res. 2015; 75:1504-15.
17. Zauri M, Berridge G, Thézénas M-L, Pugh K M, Goldin R, Kessler B M, et al. CDA directs metabolism of epigenetic nucleosides revealing a therapeutic window in cancer. Nature. 2015; 524:114-8.
18. Helleday T. Poisoning Cancer Cells with Oxidized Nucleosides. N Engl J Med. 2015; 373:1570-1.
19. Gemble S, Ahuja A, Buhagiar-Labarchède G, Onclercq-Delic R, Dairou J, Biard D S F, et al. Pyrimidine Pool Disequilibrium Induced by a Cytidine Deaminase Deficiency Inhibits PARP-1 Activity, Leading to the Under Replication of DNA. PLoS Genet. 2015; 11:e1005384.
20. Baldeyron C, Brisson A, Tesson B, Némati F, Koundrioukoff S, Saliba E, et al. TIPIN depletion leads to apoptosis in breast cancer cells. Mol Oncol. 2015; 9:1580-98.
21. Marangoni E, Vincent-Salomon A, Auger N, Degeorges A, Assayag F, Cremoux P de, et al. A New Model of Patient Tumor-Derived Breast Cancer Xenografts for Preclinical Assays. Clin Cancer Res. 2007; 13:3989-98.
22. Nogales V, Reinhold W C, Varma S, Martinez-Cardus A, Moutinho C, Moran S, et al. Epigenetic inactivation of the putative DNA/RNA helicase SLFN11 in human cancer confers resistance to platinum drugs. Oncotarget. 2015;
23. Shin G, Kang T-W, Yang S, Baek S-J, Jeong Y-S, Kim S-Y. GENT: gene expression database of normal and tumor tissues. Cancer Inform. 2011; 10:149-57.
24. den Boon J A, Pyeon D, Wang S S, Horswill M, Schiffman M, Sherman M, et al. Molecular transitions from papillomavirus infection to cervical precancer and cancer: Role of stromal estrogen receptor signaling. Proc Natl Acad Sci USA. 2015; 112:E3255-3264.
25. Gilbert J A, Salavaggione O E, Ji Y, Pelleymounter L L, Eckloff B W, Wieben E D, et al. Gemcitabine pharmacogenomics: cytidine deaminase and deoxycytidylate deaminase gene resequencing and functional genomics. Clin Cancer Res Off J Am Assoc Cancer Res. 2006; 12:1794-803.
26. Abraham A, Varatharajan S, Abbas S, Zhang W, Shaji R V, Ahmed R, et al. Cytidine deaminase genetic variants influence RNA expression and cytarabine cytotoxicity in acute myeloid leukemia. Pharmacogenomics. 2012; 13:269-82.
27. Sugiyama E, Kaniwa N, Kim S-R, Kikura-Hanajiri R, Hasegawa R, Maekawa K, et al. Pharmacokinetics of gemcitabine in Japanese cancer patients: the impact of a cytidine deaminase polymorphism. J Clin Oncol Off J Am Soc Clin Oncol. 2007; 25:32-42.
28. Christman J K. 5-Azacytidine and 5-aza-2'-deoxycytidine as inhibitors of DNA methylation: mechanistic studies and their implications for cancer therapy. Oncogene. 2002; 21:5483-95.
29. Samulitis B K, Pond K W, Pond E, Cress A E, Patel H, Wisner L, et al. Gemcitabine resistant pancreatic cancer cell lines acquire an invasive phenotype with collateral hypersensitivity to histone deacetylase inhibitors. Cancer Biol Ther. 2015; 16:43-51.
30. Yoshida T, Endo Y, Obata T, Kosugi Y, Sakamoto K, Sasaki T. Influence of cytidine deaminase on antitumor activity of 2'-deoxycytidine analogs in vitro and in vivo. Drug Metab Dispos Biol Fate Chem. 2010; 38:1814-9.
31. Cerami E, Gao J, Dogrusoz U, Gross B E, Sumer S O, Aksoy B A, et al. The cBio cancer genomics portal: an open platform for exploring multidimensional cancer genomics data. Cancer Discov. 2012; 2:401-4.
32. Gao J, Aksoy B A, Dogrusoz U, Dresdner G, Gross B, Sumer S O, et al. Integrative analysis of complex cancer genomics and clinical profiles using the cBioPortal. Sci Signal. 2013; 6:pl1.
33. Reinhold W C, Sunshine M, Varma S, Doroshow J H, Pommier Y. Using CellMiner 1.6 for Systems Pharmacology and Genomic Analysis of the NCI-60. Clin Cancer Res Off J Am Assoc Cancer Res. 2015; 21:3841-52.
34. Meng L, Shankavaram U, Chen C, Agama K, Fu H, Gonzalez F J, et al. Activation of aminoflavone (NSC 686288) by a sulfotransferase is required for the antiproliferative effect of the drug and for induction of histone gamma-H2AX. Cancer Res. 2006; 66:9656-64.

35. Meng L, Kohlhagen G, Liao Z, Antony S, Sausville E, Pommier Y. DNA-protein cross-links and replication-dependent histone H2AX phosphorylation induced by aminoflavone (NSC 686288), a novel anticancer agent active against human breast cancer cells. Cancer Res. 2005; 65:5337-43.
36. Meng L-H, Kohn K W, Pommier Y. Dose-response transition from cell cycle arrest to apoptosis with selective degradation of Mdm2 and p21WAF1/CIP1 in response to the novel anticancer agent, aminoflavone (NSC 686,288). Oncogene. 2007; 26:4806-16.
37. McLean L, Soto U, Agama K, Francis J, Jimenez R, Pommier Y, et al. Aminoflavone induces oxidative DNA damage and reactive oxidative species-mediated apoptosis in breast cancer cells. Int J Cancer J Int Cancer. 2008; 122:1665-74.
38. Loaiza-Perez A I, Kenney S, Boswell J, Hollingshead M, Alley M C, Hose C, et al. Aryl hydrocarbon receptor activation of an antitumor aminoflavone: basis of selective toxicity for MCF-7 breast tumor cells. Mol Cancer Ther. 2004; 3:715-25.
39. Terzuoli E, Puppo M, Rapisarda A, Uranchimeg B, Cao L, Burger A M, et al. Aminoflavone, a ligand of the aryl hydrocarbon receptor, inhibits HIF-1alpha expression in an AhR-independent fashion. Cancer Res. 2010; 70:6837-48.
40. Stark K, Burger A, Wu J, Shelton P, Polin L, Li J. Reactivation of estrogen receptor a by vorinostat sensitizes mesenchymal-like triple-negative breast cancer to aminoflavone, a ligand of the aryl hydrocarbon receptor. PloS One. 2013; 8:e74525.
41. Bhatla D, Gerbing R B, Alonzo T A, Conner H, Ross J A, Meshinchi S, et al. Cytidine deaminase genotype and toxicity of cytosine arabinoside therapy in children with acute myeloid leukemia. Br J Haematol. 2009; 144:388-94.
42. Mahfouz R Z, Jankowska A, Ebrahem Q, Gu X, Visconte V, Tabarroki A, et al. Increased CDA expression/activity in males contributes to decreased cytidine analog half-life and likely contributes to worse outcomes with 5-azacytidine or decitabine therapy. Clin Cancer Res Off J Am Assoc Cancer Res. 2013; 19:938-48.
43. Benhura M A. Metabolism of cytosine arabinoside in Tetrahymena pyriformis. Comp Biochem Physiol B. 1985; 80:821-5.
44. Serdjebi C, Milano G, Ciccolini J. Role of cytidine deaminase in toxicity and efficacy of nucleosidic analogs. Expert Opin Drug Metab Toxicol. 2015; 11:665-72.

---

The invention claimed is:

1. A method for selecting and treating a patient affected with a tumor with an antitumor compound, the method comprising:
   (a) measuring the expression level of Cytidine Deaminase (CDA) in a cancer sample from said patient,
   (b) comparing the CDA expression level of the cancer sample to a reference expression level, wherein a CDA expression level of the cancer sample lower than the reference expression level is predictive of the efficacy of a treatment with aminoflavone, and/or wherein a CDA expression level of the cancer sample higher than the reference expression level is predictive of the efficacy of a treatment with dasatinib,
   (c) selecting patients with CDA expression level of their cancer sample lower than the reference expression level as suitable for a treatment with aminoflavone and/or selecting patients with CDA expression level of their cancer sample higher than the reference expression level for a treatment with dasatinib, and (d) administering aminoflavone to a patient in which CDA expression level is lower than a reference expression level or administering dasatinib to a patient in which CDA expression level is higher than a reference expression level.

2. The method according to claim 1, said method comprising administering aminoflavone to a patient in which CDA expression level is lower than a reference expression level.

3. The method according to claim 1, said method comprising administering dasatinib to a patient in which CDA expression level is higher than a reference expression level.

4. The method according to claim 1, wherein said cancer in which CDA expression level is lower than a reference expression level has a CDA expression level at least two times less than the reference expression level, at least four times less than the reference expression level or said cancer does not express CDA.

5. The method according to claim 1, wherein said cancer in which CDA expression level is higher than a reference expression level has a CDA expression level at least two times more than the reference expression level, at least four times more than the reference expression level, or at least ten times more than the reference expression level.

6. The method according to claim 1, wherein the reference expression level is the expression level of CDA in a normal sample or a normal sample from the same tissue or a tissue counterpart.

7. The method according to claim 6, wherein said normal sample is a sample from the same patient.

8. The method according to claim 6, wherein the reference expression level is the average of the expression level of CDA in normal samples from several patients.

9. The method according to claim 1, wherein the reference expression level is the expression level of CDA in a non-cancerous cell-line or the average of the CDA expression level of several non-cancerous cell-lines from the same tissue as the cancer sample.

10. The method according to claim 2, wherein the reference expression level is the average of the CDA expression levels of cancer samples from several patients of the same tissue.

11. The method according to claim 1, wherein the expression level of CDA is determined by measuring the quantity of CDA protein or CDA mRNA.

12. The method according to claim 1, wherein said cancer is a solid or a hematopoietic tumor.

13. The method according to claim 1, wherein the cancer is selected from the group consisting of prostate cancer, lung cancer, breast cancer, gastric cancer, kidney cancer, ovarian cancer, hepatocellular cancer, osteosarcoma, melanoma, hypopharynx cancer, esophageal cancer, endometrial cancer, cervical cancer, pancreatic cancer, liver cancer, colon or colorectal cancer, neuroendocrine tumors, a malignant tumor of the muscle, adrenal cancer, thyroid cancer, uterine cancer, skin cancer, bladder cancer, head and neck cancer, lymphoma, and leukemia.

14. The method according to claim 1, wherein the patient is an animal or a human.

15. The method according to claim 14, wherein the patient is a new-born, a child or an adult.

* * * * *

UNITED STATES PATENT AND TRADEMARK OFFICE
CERTIFICATE OF CORRECTION

PATENT NO. : 11,209,421 B2
APPLICATION NO. : 16/086624
DATED : December 28, 2021
INVENTOR(S) : Mounira Amor-Gueret and Hamza Mameri It is certified that error appears in the above-identified patent and that said Letters Patent is hereby corrected as shown below:

In the Specification

Column 64,
Line 5, "receptor a" should read --receptor α--.

Signed and Sealed this
Twenty-eighth Day of June, 2022

Katherine Kelly Vidal
*Director of the United States Patent and Trademark Office*

SEQUENCE LISTING

```
<160> NUMBER OF SEQ ID NOS: 16

<210> SEQ ID NO 1
<211> LENGTH: 21
<212> TYPE: DNA
<213> ORGANISM: Artificial Sequence
<220> FEATURE:
<223> OTHER INFORMATION: Primer F1 of the promoter and exon 1

<400> SEQUENCE: 1
aacgggatga cttattgagg t                                                    21

<210> SEQ ID NO 2
<211> LENGTH: 20
<212> TYPE: DNA
<213> ORGANISM: Artificial Sequence
<220> FEATURE:
<223> OTHER INFORMATION: Primer R1 of the promoter and exon 1

<400> SEQUENCE: 2
catcttcctc tgacccacca                                                      20

<210> SEQ ID NO 3
<211> LENGTH: 19
<212> TYPE: DNA
<213> ORGANISM: Artificial Sequence
<220> FEATURE:
<223> OTHER INFORMATION: Primer F2 of the exon 2

<400> SEQUENCE: 3
attgccctgt ccttctccc                                                       19

<210> SEQ ID NO 4
<211> LENGTH: 20
<212> TYPE: DNA
<213> ORGANISM: Artificial Sequence
<220> FEATURE:
<223> OTHER INFORMATION: Primer R2 of the exon 2

<400> SEQUENCE: 4
```
tatcctcagc actcatccca                                               20

<210> SEQ ID NO 5
<211> LENGTH: 20
<212> TYPE: DNA
<213> ORGANISM: Artificial Sequence
<220> FEATURE:
<223> OTHER INFORMATION: Primer F3 of the exon 3

<400> SEQUENCE: 5
ccaaatcagg aacagaccga                                               20

<210> SEQ ID NO 6
<211> LENGTH: 20
<212> TYPE: DNA
<213> ORGANISM: Artificial Sequence
<220> FEATURE:
<223> OTHER INFORMATION: Primer R3 of the exon 3

<400> SEQUENCE: 6
cacaaagcag acactcactc                                               20

<210> SEQ ID NO 7
<211> LENGTH: 21
<212> TYPE: DNA
<213> ORGANISM: Artificial Sequence
<220> FEATURE:
<223> OTHER INFORMATION: Primer F4 of the exon 4

<400> SEQUENCE: 7
agcattcttt cgtttcctcc t                                             21

<210> SEQ ID NO 8
<211> LENGTH: 19
<212> TYPE: DNA
<213> ORGANISM: Artificial Sequence
<220> FEATURE:
<223> OTHER INFORMATION: Primer R4 of the exon 4

<400> SEQUENCE: 8
atctccacac cctcctcac                                                19

<210> SEQ ID NO 9
<211> LENGTH: 19
<212> TYPE: DNA
<213> ORGANISM: Artificial Sequence
<220> FEATURE:
<223> OTHER INFORMATION: Primer F of CDA

<400> SEQUENCE: 9
ccctacagtc actttcctg                                                19

<210> SEQ ID NO 10
<211> LENGTH: 20
<212> TYPE: DNA
<213> ORGANISM: Artificial Sequence
<220> FEATURE:
<223> OTHER INFORMATION: Primer R of CDA

<400> SEQUENCE: 10
cgggtagcag gcattttcta                                               20

<210> SEQ ID NO 11
<211> LENGTH: 24
<212> TYPE: DNA
<213> ORGANISM: Artificial Sequence

```
<220> FEATURE:
<223> OTHER INFORMATION: Primer F of GAPDH

<400> SEQUENCE: 11
gaaatcccat caccatcttc cagg                                          24

<210> SEQ ID NO 12
<211> LENGTH: 20
<212> TYPE: DNA
<213> ORGANISM: Artificial Sequence
<220> FEATURE:
<223> OTHER INFORMATION: Primer R of GAPDH

<400> SEQUENCE: 12
gagccccagc cttctccatg                                               20

<210> SEQ ID NO 13
<211> LENGTH: 21
<212> TYPE: DNA
<213> ORGANISM: Artificial Sequence
<220> FEATURE:
<223> OTHER INFORMATION: Primer F of TBP

<400> SEQUENCE: 13
tgcacaggag ccaagagtga a                                             21

<210> SEQ ID NO 14
<211> LENGTH: 20
<212> TYPE: DNA
<213> ORGANISM: Artificial Sequence
<220> FEATURE:
<223> OTHER INFORMATION: Primer R of TBP

<400> SEQUENCE: 14
cacatcacag ctccccacca                                               20

<210> SEQ ID NO 15
<211> LENGTH: 19
<212> TYPE: DNA
<213> ORGANISM: Artificial Sequence
<220> FEATURE:
<223> OTHER INFORMATION: Primer ESR1 Forward

<400> SEQUENCE: 15
ccggctccgc aaatgctac                                                19

<210> SEQ ID NO 16
<211> LENGTH: 21
<212> TYPE: DNA
<213> ORGANISM: Artificial Sequence
<220> FEATURE:
<223> OTHER INFORMATION: Primer ESR1 Reverse

<400> SEQUENCE: 16
aaggttggca gctctcatgt c                                             21
```